(12) United States Patent
Klee et al.

(10) Patent No.: US 10,588,830 B2
(45) Date of Patent: Mar. 17, 2020

(54) DENTAL COMPOSITION

(71) Applicant: DENTSPLY SIRONA Inc., York, PA (US)

(72) Inventors: Joachim E. Klee, Radolfzell (DE); Florian Szillat, Constance (DE); Maximilian Maier, Constance (DE); Helmut Ritter, Wuppertal (DE); Jacques Lalevee, Mulhouse (FR); Jean Pierre Fouassier, Hippolyte (FR); Fabrice Morlet-Savary, Pfastatt (FR); Celine Dietlin, Mulhouse (FR); Mariem Bouzrati-Zerelli, Mulhouse (FR); Christoph P Fik, Schonenberg a.d. Thur (CH)

(73) Assignee: DENTSPLY SIRONA INC., York, PA (US)

( * ) Notice: Subject to any disclaimer, the term of this patent is extended or adjusted under 35 U.S.C. 154(b) by 76 days.

(21) Appl. No.: 15/766,382

(22) PCT Filed: Oct. 7, 2016

(86) PCT No.: PCT/EP2016/074049
§ 371 (c)(1),
(2) Date: Apr. 6, 2018

(87) PCT Pub. No.: WO2017/060459
PCT Pub. Date: Apr. 13, 2017

(65) Prior Publication Data
US 2018/0303722 A1    Oct. 25, 2018

(30) Foreign Application Priority Data

Oct. 8, 2015   (EP) ..................... 15188969

(51) Int. Cl.
*A61K 6/00*      (2020.01)
*A61K 6/08*      (2006.01)
*A61K 6/083*     (2006.01)

(52) U.S. Cl.
CPC .......... *A61K 6/0052* (2013.01); *A61K 6/0017* (2013.01); *A61K 6/0023* (2013.01); *A61K 6/0073* (2013.01); *A61K 6/0097* (2013.01); *A61K 6/083* (2013.01)

(58) Field of Classification Search
CPC .. A61K 6/0052; A61K 6/0017; A61K 6/0097; A61K 6/0073; A61K 6/083; A61K 6/0023
See application file for complete search history.

(56) References Cited

U.S. PATENT DOCUMENTS

| 4,437,959 | A   |   | 3/1984  | Hayase |
| 9,532,930 | B2  | * | 1/2017  | Burtscher ............ A61K 6/0835 |
| 2008/0076847 | A1 |  | 3/2008  | Moszner |
| 2015/0080490 | A1 |  | 3/2015  | Burtscher |
| 2018/0289592 | A1 | * | 10/2018 | Klee .................. A61K 6/0017 |

FOREIGN PATENT DOCUMENTS

WO    2015144579 A1    10/2015

OTHER PUBLICATIONS

International Search Report dated Dec. 7, 2016.
Mohamad El-Roz et al: "A search for new radical sources in photoinitiating systems", Current Trends in Polymer Science, Research Trends, In, vol. 15, Jan. 1, 2011 (Jan. 1, 2011), pp. 1-13, XP008179332, ISSN: 0972-446X cited in the application p. 2, compound Si1, Si2, Si3, Si7, Si8, and Si9.

* cited by examiner

*Primary Examiner* — Sanza L. McClendon
(74) *Attorney, Agent, or Firm* — Dentsply Sirona Inc.

(57) ABSTRACT

The present invention relates to a dental composition comprising a specific polymerization initiator system comprising a compound having an acylsilyl- or acylgermanyl-group. The present invention also relates the use of the compound having an acylsilyl- or acylgermanyl group for the preparation of a dental composition.

11 Claims, 14 Drawing Sheets

DENTAL COMPOSITION

FIELD OF THE INVENTION

The present invention relates to a dental composition comprising a specific polymerization initiator system comprising a compound having a silyl or germanyl group. The present invention also relates the use of the compound having a silyl or germanyl group for the preparation of a dental composition.

BACKGROUND OF THE INVENTION

The restoration of teeth commonly involves a light curable dental composition containing free-radically polymerizable resins. Light curing of a dental composition involves a photoinitiator system generating free radicals upon exposure to visible light. Free radicals may be typically produced by either of two pathways:
(1) the photoinitiator compound undergoes excitation by energy absorption with subsequent decomposition of the compound into one or more radicals (Norrish type I), or
(2) the photoinitiator compound undergoes excitation and the excited photoinitiator compound interacts with a second compound by either energy transfer or a redox reaction to form free radicals from any of the compounds (Norrish type II).

In order for a photoinitiator to be useful for use in a dental composition, the quantum yields indicating the conversion of light radiation to radical formation needs to be high since absorption or shielding of light by further components of the dental composition limit the amount of energy available for absorption by the photoinitiators. Accordingly, only about 70 percent conversion of the polymerizable groups may be expected in a polymerization of a typical dental composition, whereby the mechanical strength of the polymerized dental composition is less than optimal and unreacted monomers may leach out of the polymerized dental composition. The leaching monomers may have detrimental effects. In order to alleviate this problem, multifunctional monomers are frequently used which are more likely to be included in the polymer network.

In addition, photoinitiators are required to have a high acid resistance, solubility, thermal stability, and storage stability when incorporated into a dental composition.

Finally, given that dental compositions usually contain (meth)acrylate or (meth)acrylamide monomers, free radical photocuring may be inhibited by the presence of oxygen. Oxygen inhibition is due to the rapid reaction of propagating radicals with oxygen molecules to yield peroxyl radicals which are not as reactive towards carbon-carbon unsaturated double bonds and therefore do not initiate or participate in any photopolymerization reaction. Oxygen inhibition may lead to premature chain termination and, therefore, incomplete photocuring. Nevertheless, a certain degree of oxygen inhibition on the top surface of the adhesive layer is required for the bonding to the adjacent restorative.

Accordingly, the polymerization initiator system has a critical influence on the quality of the dental material. Conventionally, camphor quinone optionally in combination with a tertiary amine, or 2,4,6-trimethylbenzoylphenyl phosphinate (Irgacure® TPO) are frequently used as photoinitiator system. However, the presence of amines in acrylate-containing compositions can cause yellowing in the resulting photocured composition, create undesirable odors, and soften the cured composition because of chain transfer reactions and therefore, often require the use of stabilizers. Moreover, the use of aromatic amines gives rise to toxicological concerns.

Furthermore, it is desirable that the light activating the photoinitiator system has a long wavelength in order to avoid damage of soft tissue during polymerization of the dental composition in the patient's mouth. Accordingly, the photoinitiator system is required to contain a chromophoric group efficiently absorbing light of the desired wavelength in a range of from 400 to 800 nm. However, an increase of the absorption coefficient of the photoinitiator system increases the coloration of the photoinitiator system and thereby the coloration of the dental composition before light curing. Accordingly, it is necessary that the chromophoric groups are efficiently destroyed during polymerization so that the coloration of the initiator system disappears in the polymerized dental composition, the so-called "photobleaching". A destruction of the chromophoric groups during polymerization may also be useful in increasing the depth of cure of the dental composition since activating light is not shielded from unpolymerized layers of the dental composition by the photoinitiator system present in polymerized layers covering the unpolymerized layers.

EP 0 076 102 A1 discloses a photopolymerizable composition comprising an epoxy compound, a curing catalyst including at least one aluminium compound having at least one organic radical directly bonded to the aluminum atom, at least one α-ketosilyl compound and at least one photosensitizer selected from the group consisting of benzophenone compounds and thioxanthone compounds. The photopolymerizable composition may be used in the field of electrical equipment, e.g. for producing an insulating material, or as a photoresist material.

EP 1 905 415 A1 discloses dental compositions comprising a polymerizable binder and a photoinitiator containing an acylgermanium compound.

EP 2 103 297 A1 discloses compositions, among others dental compositions, which comprise at least a polymerizable binder and a polymerization initiator comprising at least an acylgermanium compound. The acylgermanium compound comprises 2 to 100 acylgermanium moieties, which are linked via a bond or a branched or linear aliphatic, aromatic or aliphatic-aromatic hydrocarbon residue having a valency corresponding to the number of acylgermanium moieties. As a reference example, a dental composition is disclosed comprising a polymerization initiator system consisting of benzoyltrimethylgermane, and the polymerizable compounds UDMA and triethyleneglycoldimethacrylate.

US 2015/0080490 A1 discloses a polymerizable dental composition comprising a photoinitiator mixture which contains at least one diacylgermanium compound such as bis-(4-methoxybenzoyl)diethylgermanium, at least one α-diketon such as camphor quinone, and an accelerator.

WO 2015/144579 A1 discloses a polymerizable dental composition comprising a photoinitiator mixture that contains an α-diketone photoinitiator compound having a light absorption maximum in the range from 300 to 500 nm such as camphor quinone, and a coinitiator in the form of a hydride of silicium or germanium.

El-Roz M. et al., Current Trends in Polymer Science, 2011, vol. 15, pages 1 to 13 discloses free radical photopolymerisation of an epoxy acrylate monomer in the presence of a photoinitiator system consisting of isopropylthioxanthone as photoinitiator in combination with acylsilane compounds, among others methyl(trimethylsilyl)methanone and methyl(triphenylsilyl)methanone. This document does not disclose dental compositions.

SUMMARY OF THE INVENTION

It is the problem of the present invention to provide an improved dental composition comprising one or more compounds having a polymerizable double bond, which composition provides
improved polymerization efficiency including a high conversion and good curing rate which may be adapted to provide a suitable working time of the composition,
improved depth of cure, and
absence of coloration problems.

Moreover, it is the problem of the present invention to provide a use of a specific compound for the preparation of a dental composition.

The present invention provides a dental composition comprising
(a) one or more compounds having at least one polymerizable double bond;
(b) a polymerization initiator system comprising
(b1) a compound of the following formula (I):

wherein
X is a group of the following formula (II):

wherein
M is Si or Ge;
R$^1$ represents a substituted or unsubstituted hydrocarbyl or hydrocarbylcarbonyl group;
R$^2$ represents a substituted or unsubstituted hydrocarbyl or hydrocarbylcarbonyl group;
R$^3$ represents a substituted or unsubstituted hydrocarbyl group; and
R (i) has the same meaning as X, whereby the compound of formula (I) may be symmetrical or unsymmetrical; or
(ii) is a group of the following formula (III):

wherein
Y represents a single bond, an oxygen atom or a group NR', wherein R' represents a substituted or unsubstituted hydrocarbyl group;
R$^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group.

Furthermore, the present invention provides the use of a compound of the following formula (I):

wherein
X is a group of the following formula (II):

wherein
M is Si or Ge;
R$^1$ represents a substituted or unsubstituted hydrocarbyl or hydrocarbylcarbonyl group;
R$^2$ represents a substituted or unsubstituted hydrocarbyl or hydrocarbylcarbonyl group;
R$^3$ represents a substituted or unsubstituted hydrocarbyl group; and
R (i) has the same meaning as X, whereby the compound of formula (I) may be symmetrical or unsymmetrical; or
(ii) is a group of the following formula (III):

wherein
Y represents a single bond, an oxygen atom or a group NR', wherein R' represents a substituted or unsubstituted hydrocarbyl group;
R$^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group,
for the preparation of a dental composition.

The present invention is based on the recognition that a dental composition according to the present invention comprising (b1) a compound of the following formula (I) provides improved polymerization efficiency and high curing speed, and does not give rise to coloration problems of a dental composition. Accordingly, a relatively large amount of the dental composition can be photocured with reduced exposure to radiation. Due to the high efficiency of the polymerization initiator system (b), the presence of oxygen, or oxygen inhibition, is not a serious detriment during photocuring of a dental composition according to the present invention.

Figure 1A:
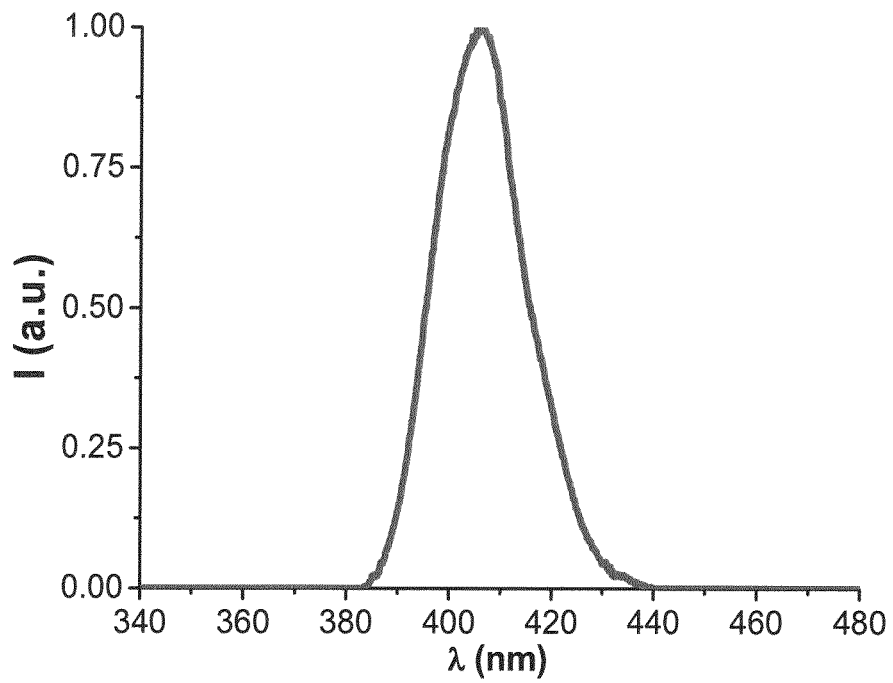
FIGS. 1a and 1b show the emission spectra of the irradiation sources used for the irradiation of the photocurable samples, namely a light emitting diode (LED) centred at 405 nm (M405L2 from ThorLabs; about 1100 mW/cm$^2$) and a blue dental LED centred at 477 nm (SmartLite® Focus from Dentsply, about 1000 mW/cm$^2$).

Curve (1): BDMSI/ethyldimethylaminobenzoate (EDB) 1%/2% w/w;
curve (2): BDMSi/diphenyliodonium hexafluorophosphate (DPI) 1%/2% w/w;
curve (3): BDMSi/2,4,6-tris(trichloromethyl)-1,3,5-triazine 1%/2% w/w;
curve (4): BDMSi/DPI/EDB 1%/2%/2% w/w;
curve (5): BDMSi/DPI/EDB 1%/2%/2% w/w after one day aging;
curve (6): BDMSi/2,4,6-tris(trichloromethyl)-1,3,5-triazine/EDB 1%/2%/2% w/w; and
curve (7): BDMSi/DPI/EDB 1%/4%/4% w/w.

Figure 4:
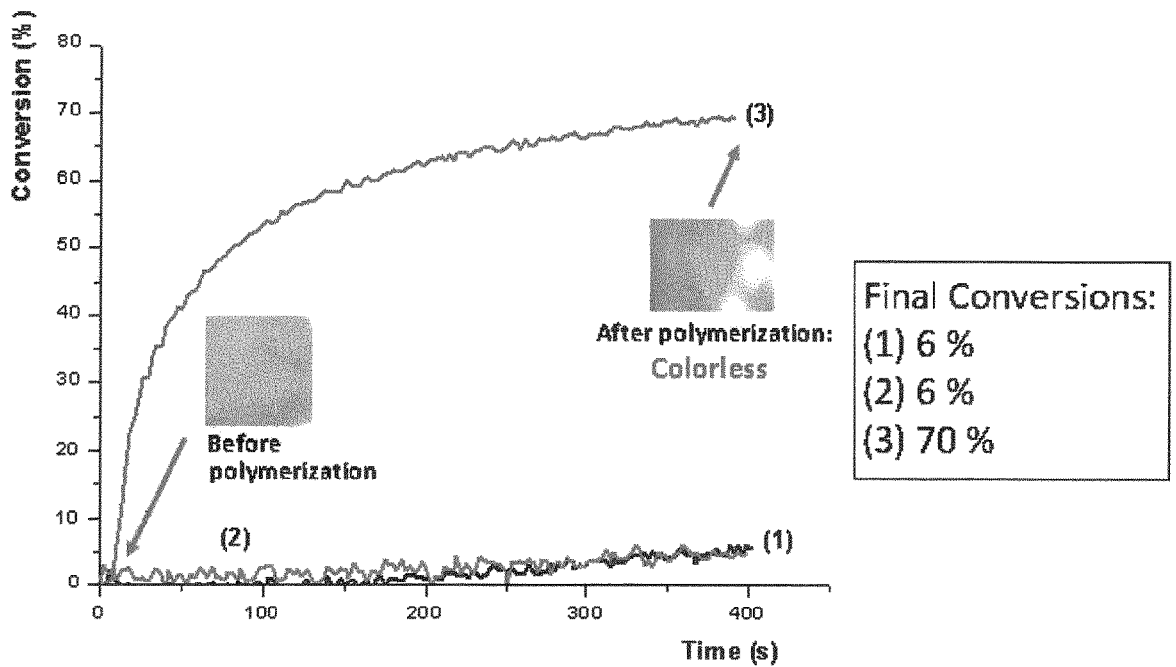

FIG. 4 shows the photopolymerization profiles of Bis-GMA/TEGDMA formulations polymerized in samples of 30 μm thickness in laminate upon the exposure to LED at 405 nm for the following different polymerization initiator systems:

Curve (1): BTMSi 1% w/w;
curve (2): BTMSi/EDB 1%/4% w/w; and
curve (3): BTMSi/DPI/EDB 1%/4%/4% w/w.

Figure 5:
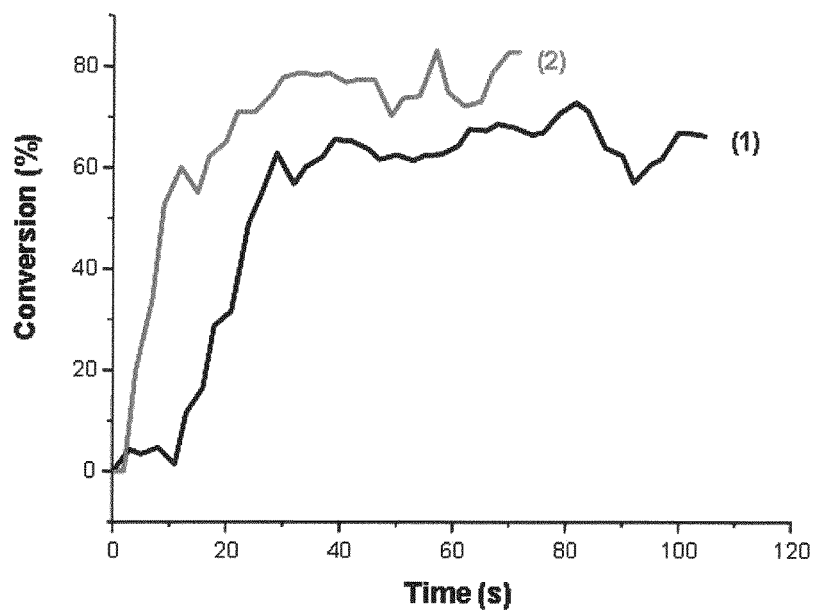

FIG. 5 shows the photopolymerization profiles of Bis-GMA/TEGDMA formulations polymerized in samples of 1.4 mm thickness under air upon the exposure to LED at 405 nm for the following different polymerization initiator systems:

Curve (1): BDMSi/DPI/EDB 1%/4%/4% w/w; and
curve (2): BTMSi/DPI/EDB 1%/4%/4% w/w.

Figure 6:
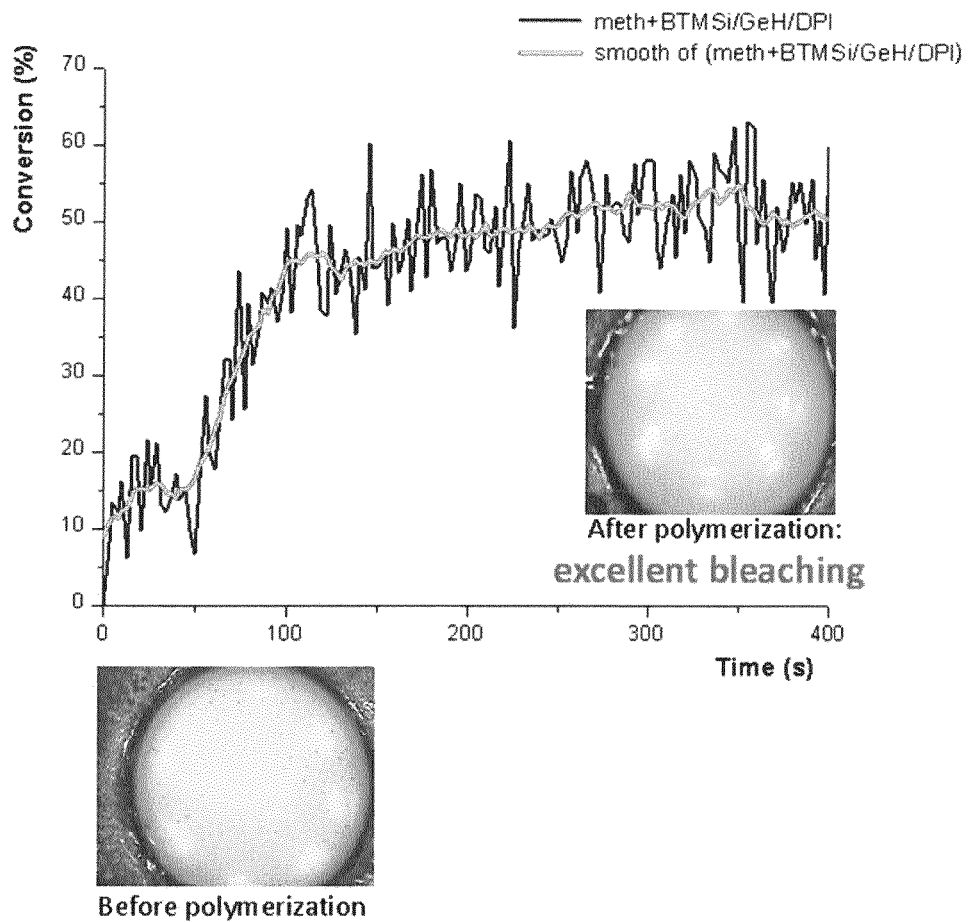

FIG. 6 shows the photopolymerization profile of a Bis-GMA/TEGDMA formulation polymerized in a sample of 1.4 mm thickness under air in the presence of a BTMSi/Ph$_3$GeH/DPI 2%/2%/2% w/w polymerisation initiator system upon the exposure to LED at 405 nm. The black curve is the raw data, the grey curve is the smoothed curve of the raw data.

Figure 7:
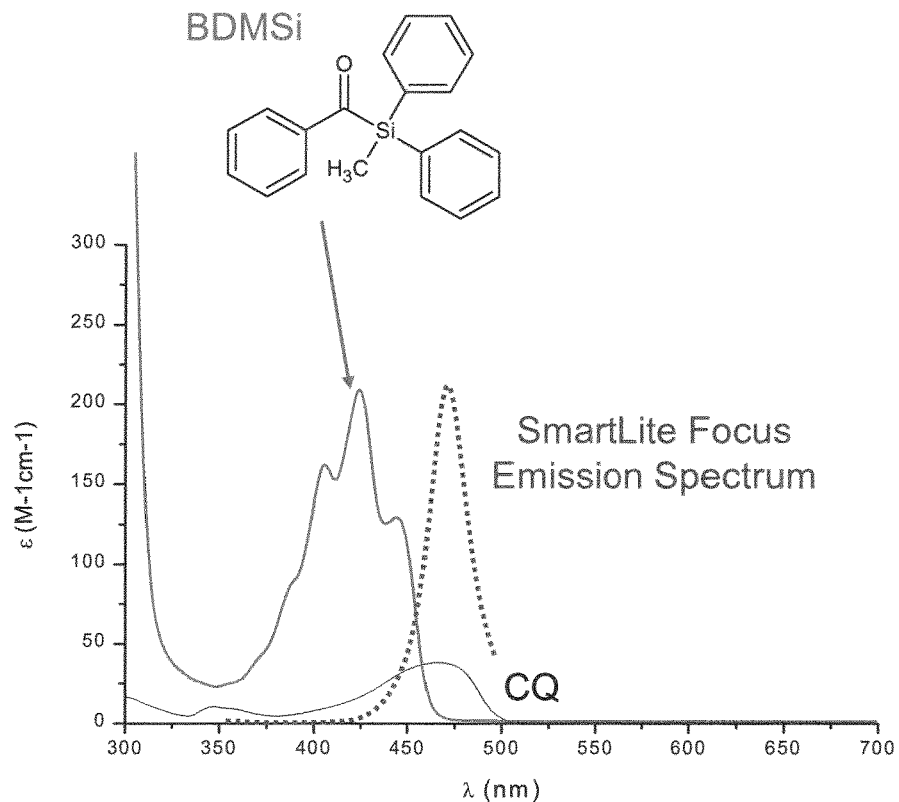

FIG. 7 shows the UV-VIS absorption spectra of BDMSi and camphor quinone (CQ) and matching with the emission spectrum of SmartLite® Focus.

Figure 8:
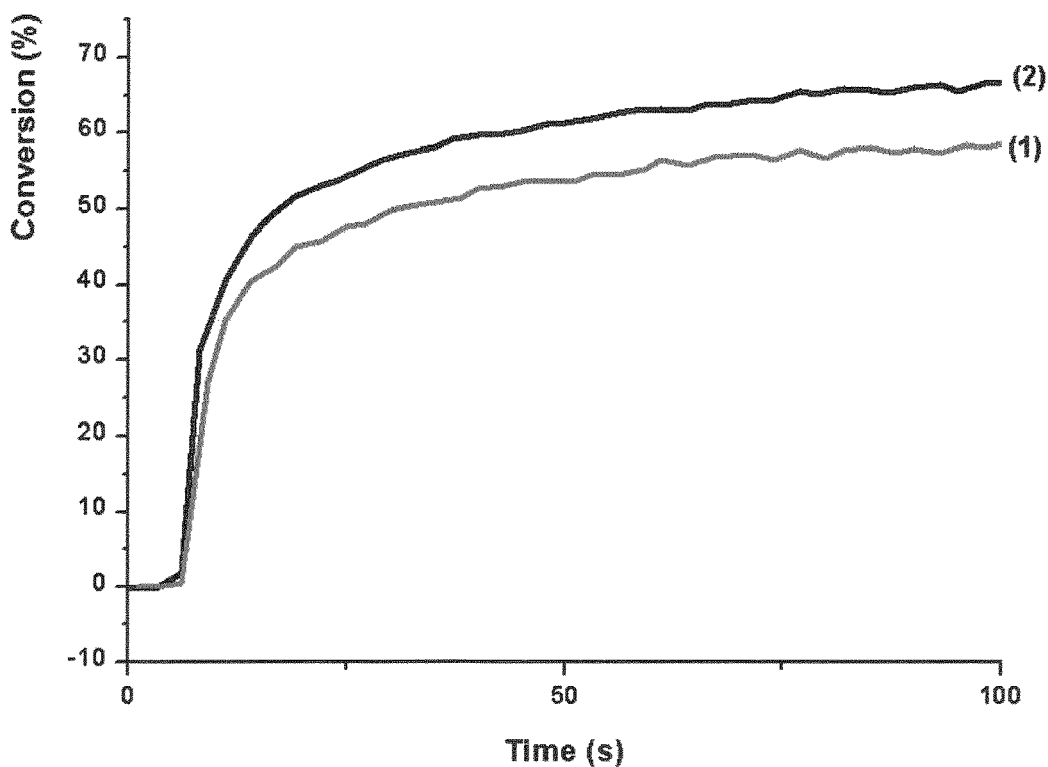

FIG. 8 shows the photopolymerization profiles of Bis-GMA/TEGDMA formulations polymerized in samples of 30 μm thickness in laminate upon the exposure to dental LED at 477 nm in the presence of the following different polymerization initiator systems:

Curve (1): CQ/EDB/DPI 1%/2%/2% w/w; and
curve (2): CQ/BDMSi/EDB/DPI 1%/2%/2%/2% w/w.

Figure 9:
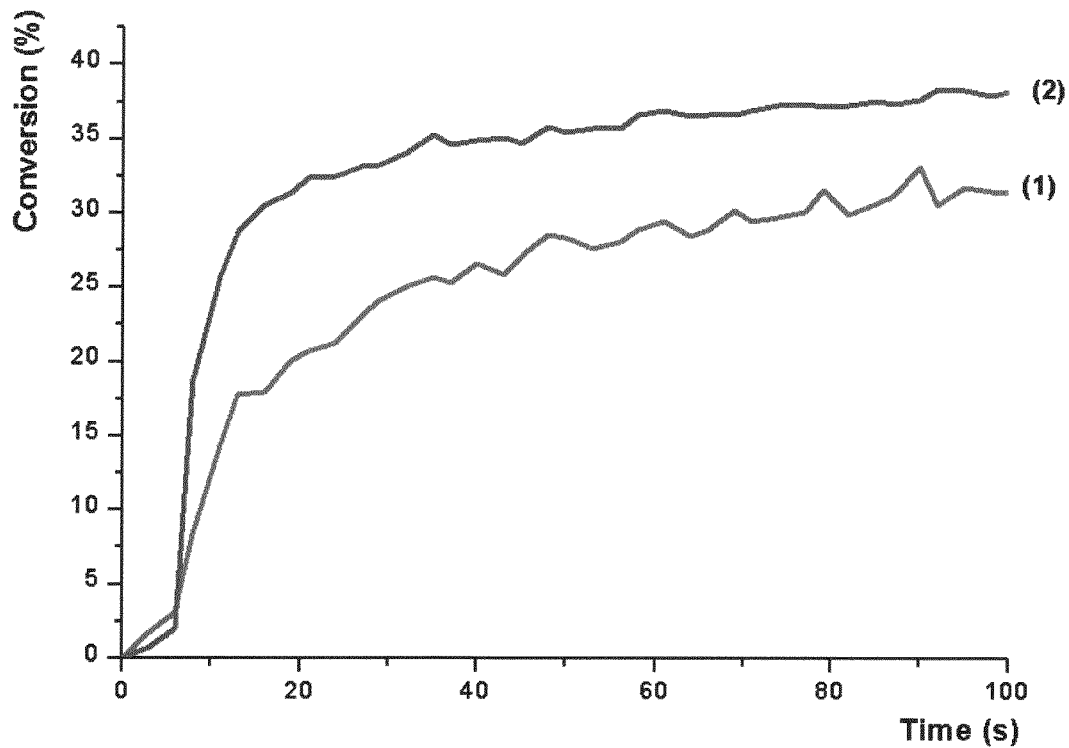

FIG. 9 shows the photopolymerization profiles of Bis-GMA/TEGDMA formulation polymerized in samples of 30 μm thickness under air upon the exposure to dental LED at 477 nm in the presence of the following different polymerization initiator systems:

Curve (1): CQ/GeH/DPI 1%/2%/2% w/w; and
curve (2): CQ/BDMSi/GeH/DPI 1%/1%/2%/2% w/w.

Figure 10:
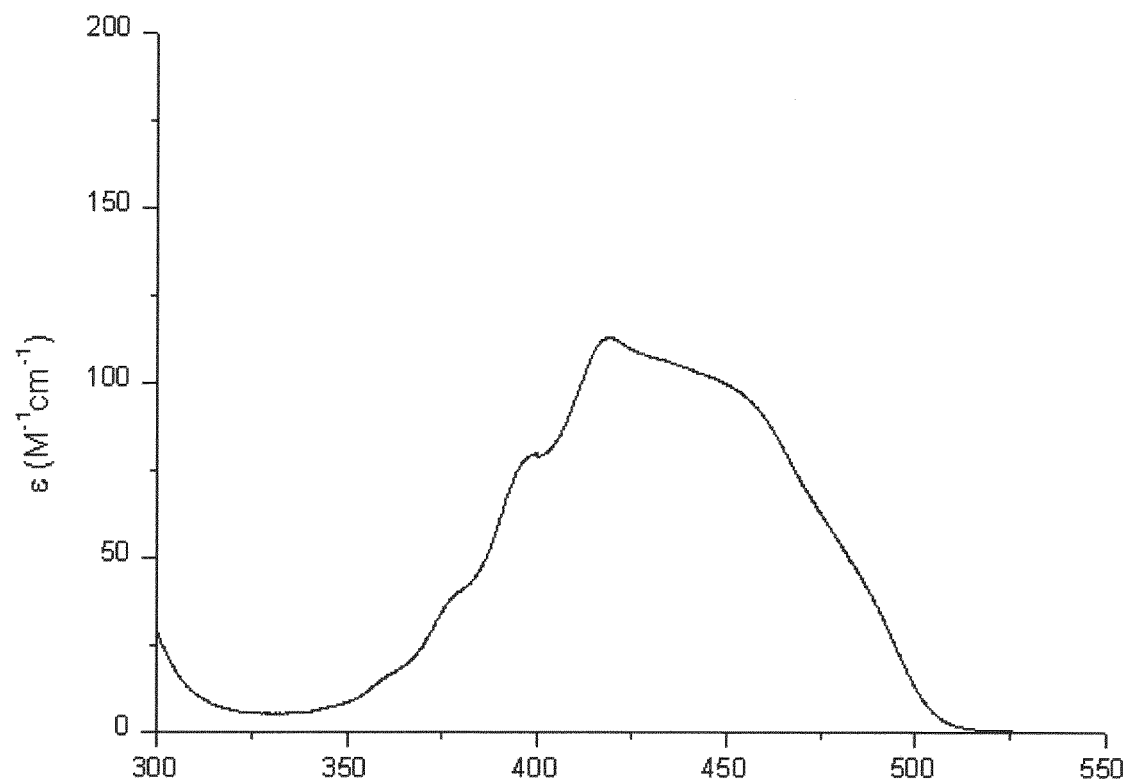

FIG. 10 shows the UV-VIS absorption spectrum of tert-butyl (tert-butyldimethylsilyl)glyoxylate) (DKSi) in toluene.

Figure 11:
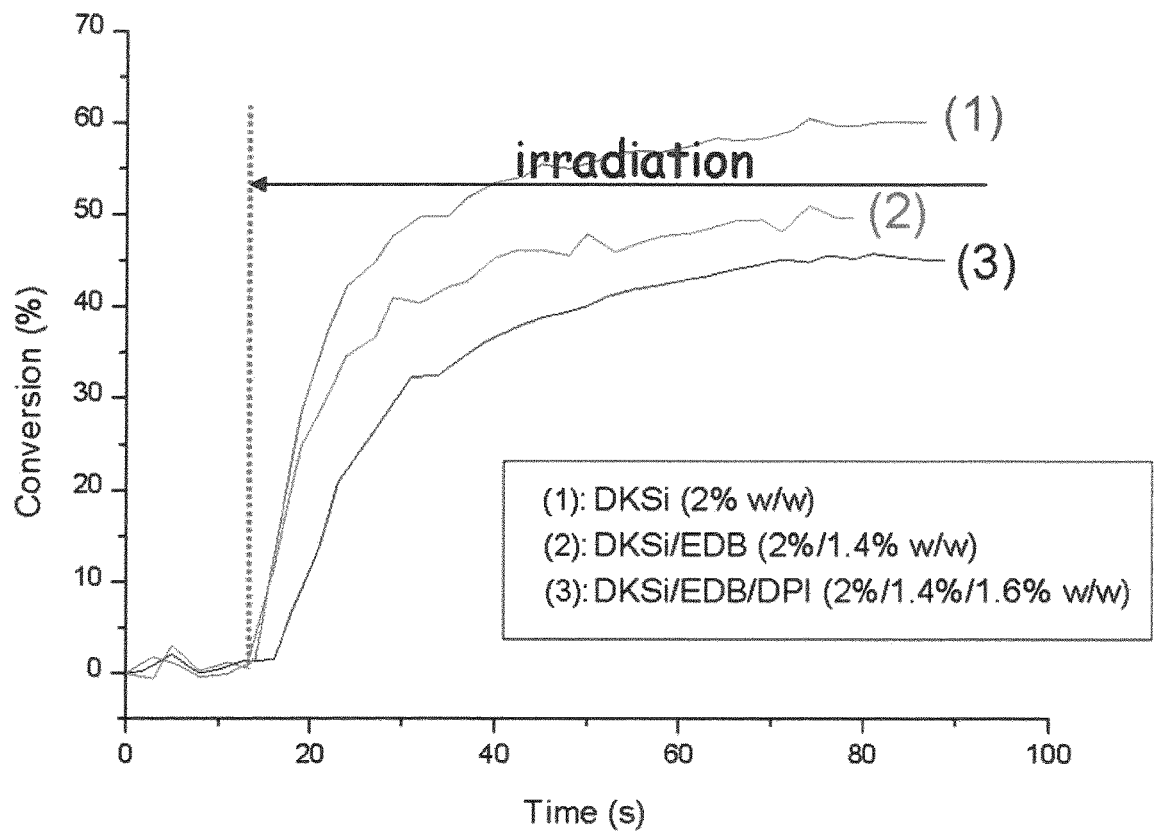

FIG. 11 shows the photopolymerization profiles of Bis-GMA/TEGDMA formulations polymerized in samples of 20 μm thickness in laminate upon the exposure to dental LED at 477 nm for the following different polymerization initiator systems:

Curve (1): DKSi/EDB/DPI 2%/1.4%/1.6% w/w
curve (2): DKSi/EDB 2%/1.4% w/w, and
curve (3): DKSi 2% w/w.

Figure 12:
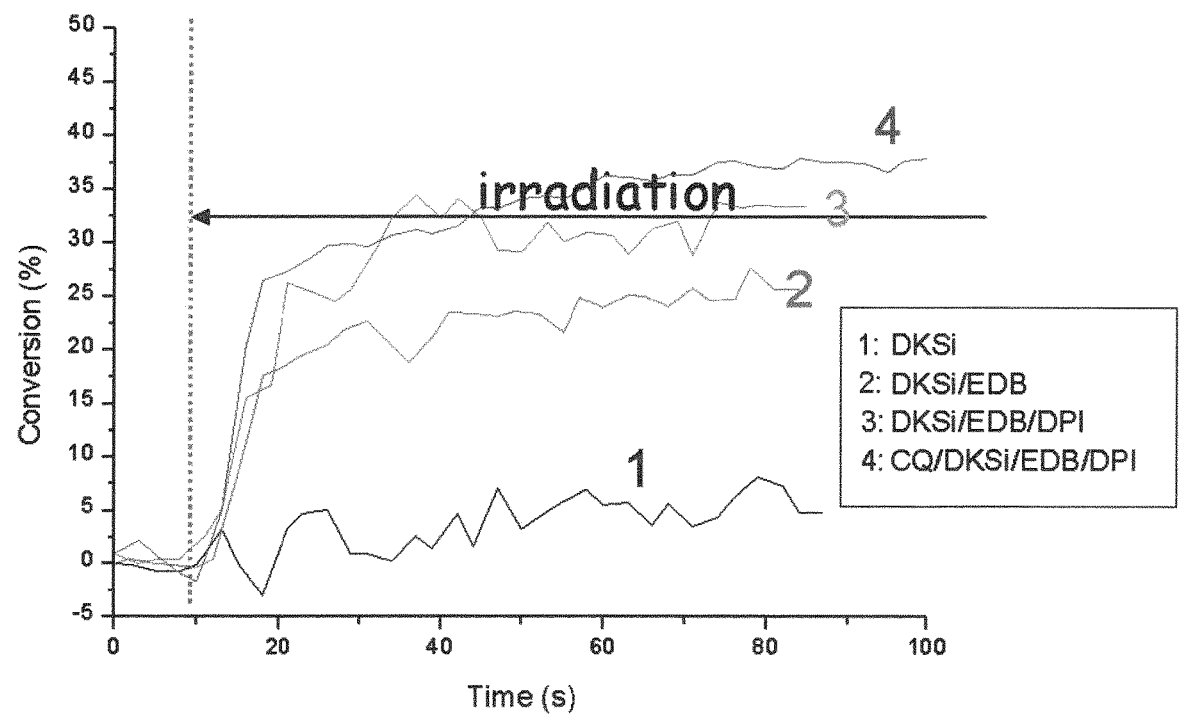

FIG. 12 shows the photopolymerization profiles of Bis-GMA/TEGDMA formulations polymerized in samples of 20 μm thickness under air upon the exposure to dental LED at 477 nm for the following different polymerization initiator systems:

Curve (1): DKSi 2% w/w;
curve (2): DKSi/EDB 2%/1.4% w/w;
curve (3): DKSi/EDB/DPI 2%/1.4%/1.6% w/w; and
curve (4): CQ/DKSi/EDB/DPI 1%/2%/1.4%/1.6% w/w.

Figure 13:
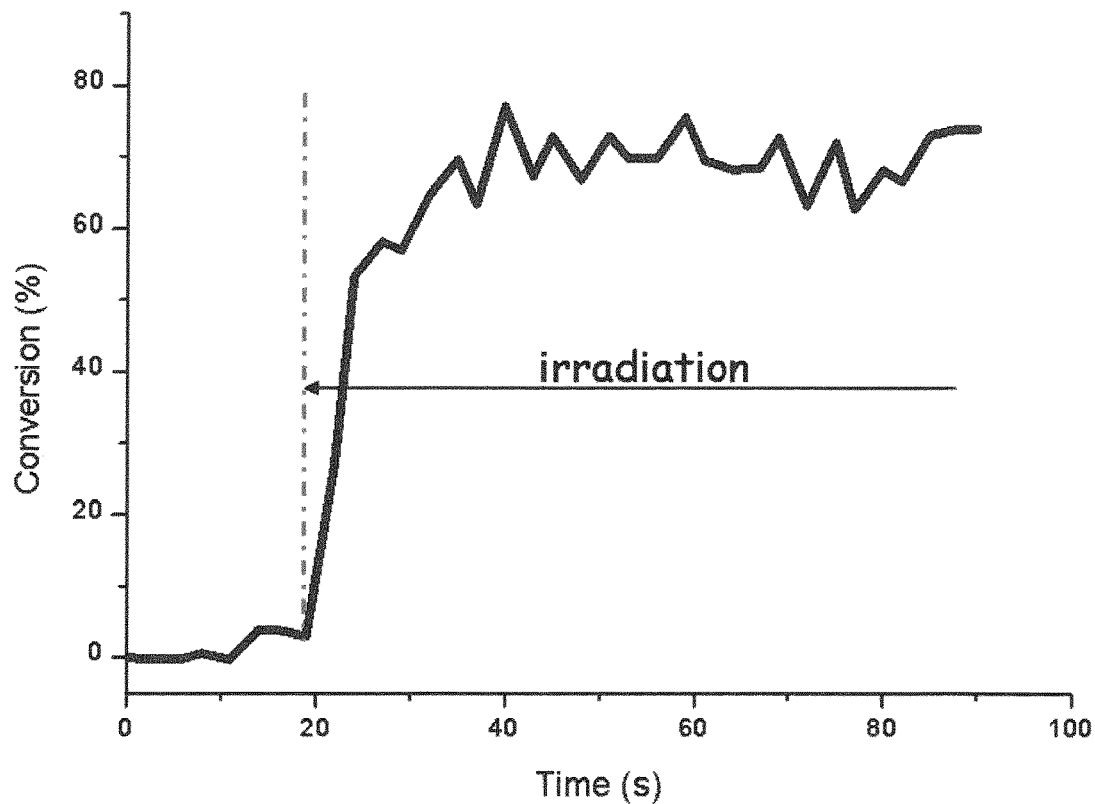

FIG. 13 shows the photopolymerization profile of a Bis-GMA/TEGDMA formulation polymerized in a sample of 1.4 mm thickness under air in the presence of a DKSi/EDB/DPI 2%/1.4%/1.6% w/w polymerisation initiator system upon the exposure to dental LED at 477 nm.

Figure 14:
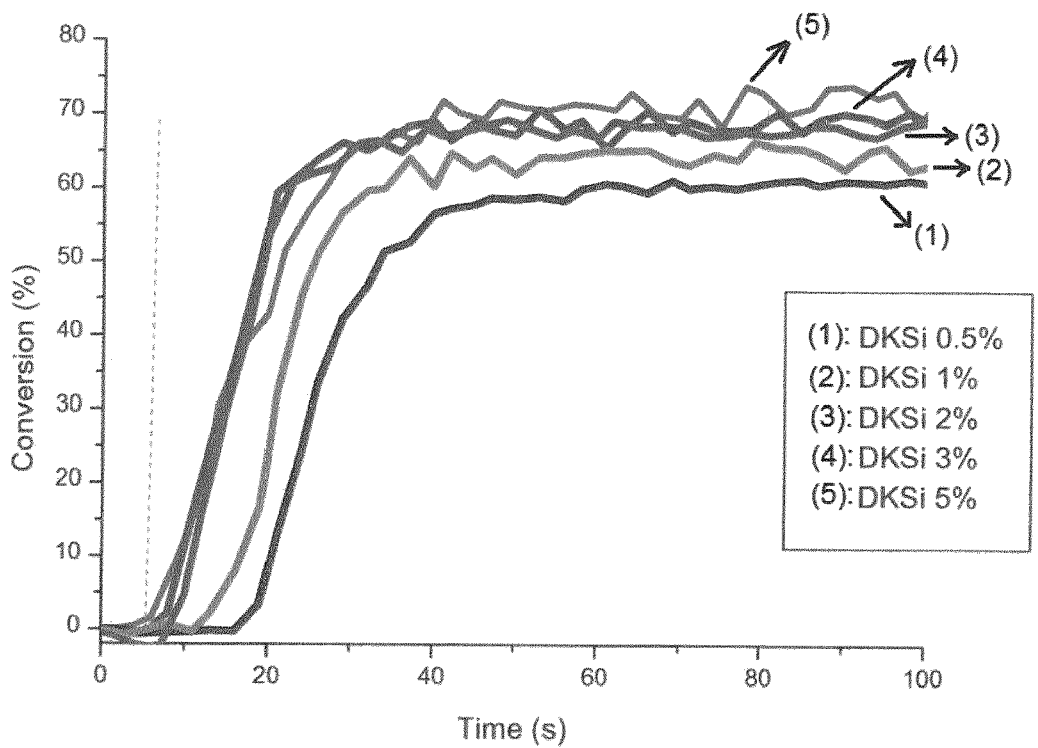

FIG. 14 shows the photopolymerization profiles of 11,14-dioxa-2,9-diazaheptadec-16-enoicacid, 4,4,6,16 (or 4,6,6,16)-tetramethy-10,15-dioxo-2-[(2-methyl-1-oxo-2-propen-1-yl)oxy]ethyl ester (UDMA) formulations polymerized in samples of 1.4 mm thickness under air upon the exposure to LED at 405 nm for the following different polymerization initiator systems:

Curve (1): DKSi 0.5% w/w;
curve (2): DKSi 1% w/w;
curve (3): DKSi 2% w/w;
curve (4): DKSi 3% w/w; and
curve (5): DKSi 5% w/w.

Figure 15A:
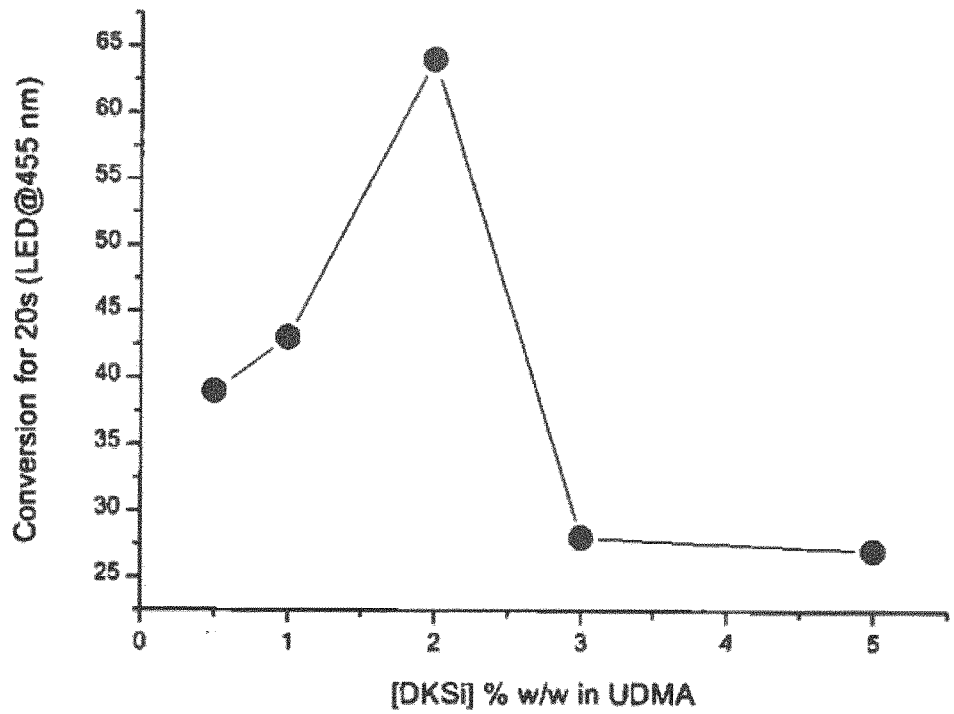
Figure 15B:
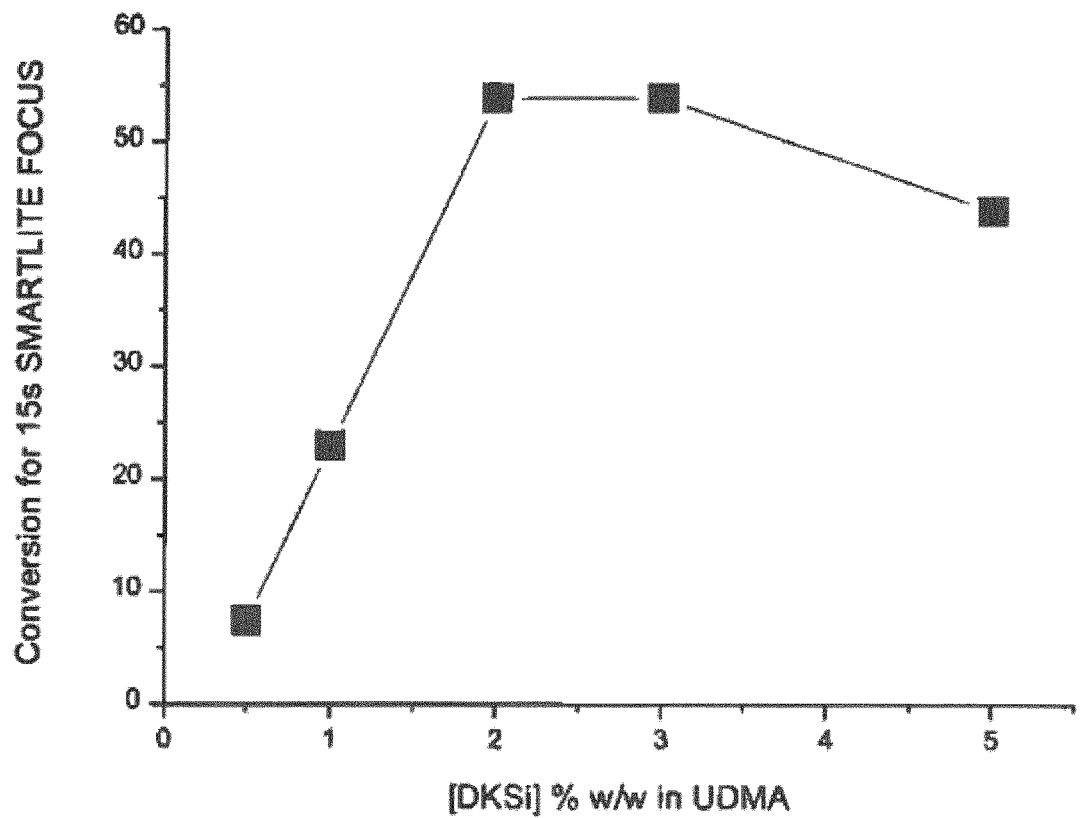

FIGS. 15a and 15b show the conversion rate for the photopolymerization of UDMA formulations polymerized in samples of 1.4 mm thickness under air after 20 seconds exposure to LED at 455 nm and to dental LED at 477 nm.

Figure 16:
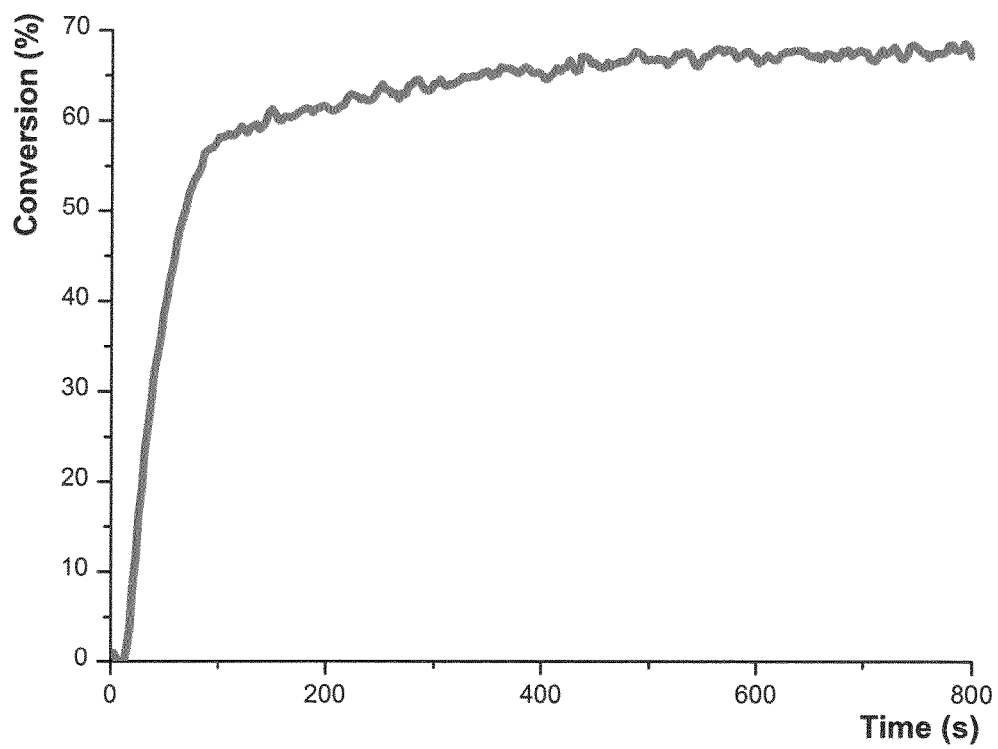

FIG. 16 shows photopolymerization profiles of an UDMA formulation polymerized in a sample of 6 mm thickness under air in the presence of DKSi (2% w/w) upon the exposure to LED at 455 nm (80 mW/cm$^2$).

Figure 17:
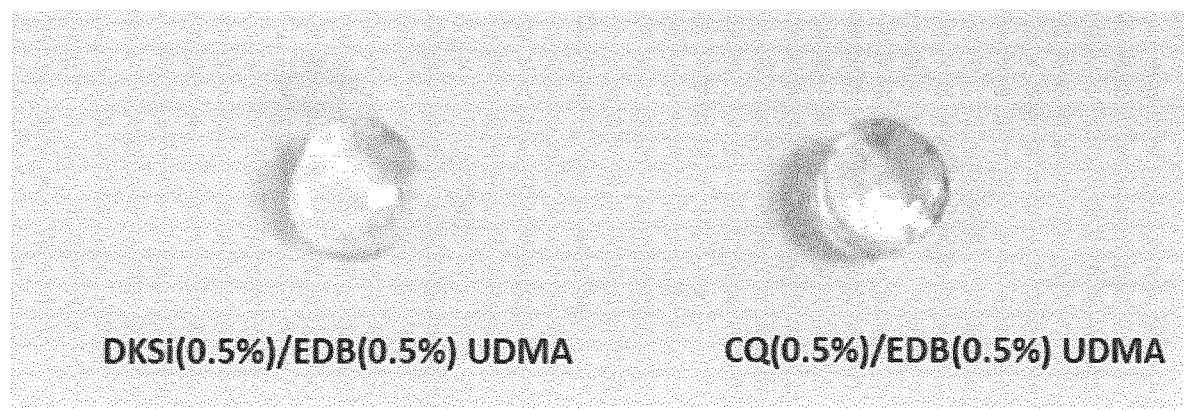

FIG. 17 shows the final colour of two polymers obtained from the photopolymerization of UDMA in a sample of 6 mm thickness under air in the presence of a DKSi/EDB or a CQ/EDB polymerization initiator system and upon exposure to LED at 455 nm (80 mW/cm$^2$).

Figure 18:
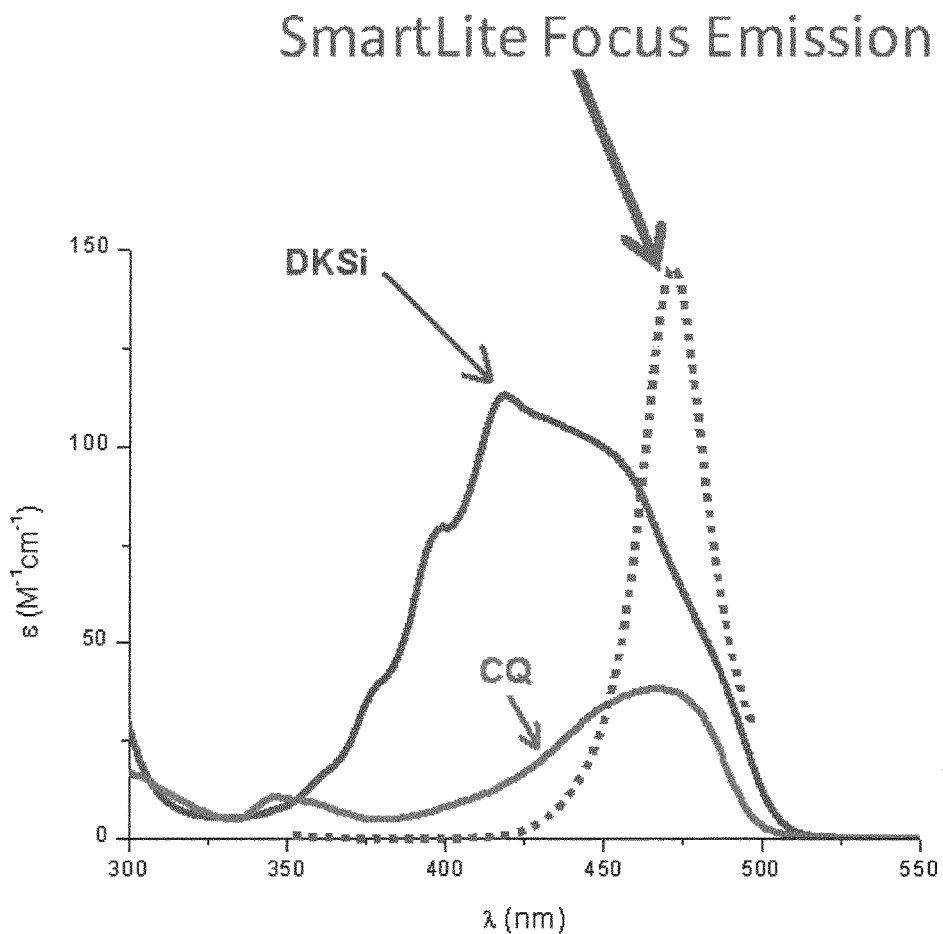

FIG. 18 shows the absorption spectrum of a CQ/DKSi polymerization initiator system and the emission spectrum of SmartLite® Focus.

Figure 19:
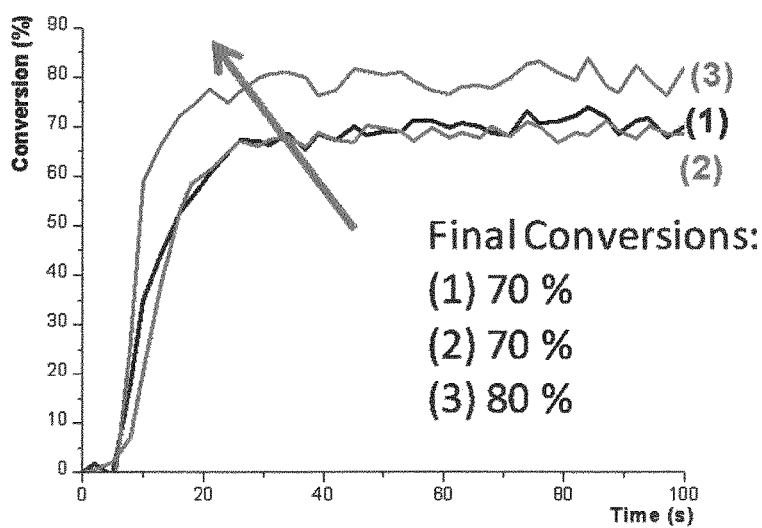

FIG. 19 shows the photopolymerization profiles of UDMA formulations polymerized in a sample of 1.4 mm thickness under air upon exposure to SmartLite® Focus for the following different polymerization initiator systems:

Curve (1): CQ (0.5% wt)/EDB (2% wt);
curve (2): DKSi (0.5% wt)/EDB (2%); and
curve (3): CQ (0.5% wt)/DKSi(0.5% wt)/EDB (2%).

Figure 20:
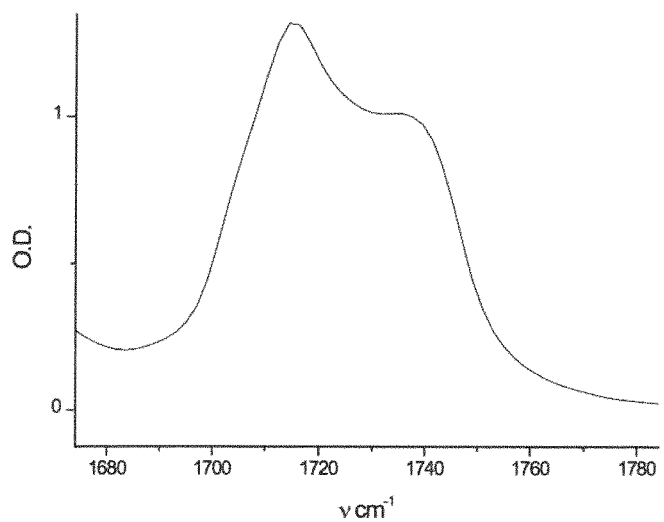

FIG. 20 shows the Fourier transform infrared (FTIR) spectrum of tert-butyl (trimethylgermanyl)glyoxylate (TKGe) obtained with an BaF$_2$ IR pellet.

Figure 21:
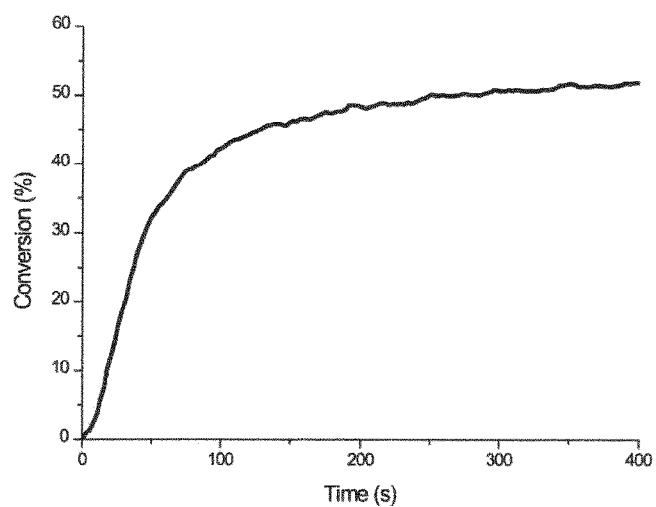

FIG. 21 shows the photopolymerization profile of UDMA polymerized with 2% w/w tert-butyl (trimethylgermanyl) glyoxylate (TKGe) under air upon the exposure to LED at about 470 nm (300 mW/cm$^2$) with SmartLite® Focus in samples of a thickness of 1.4 mm.

Figure 22:
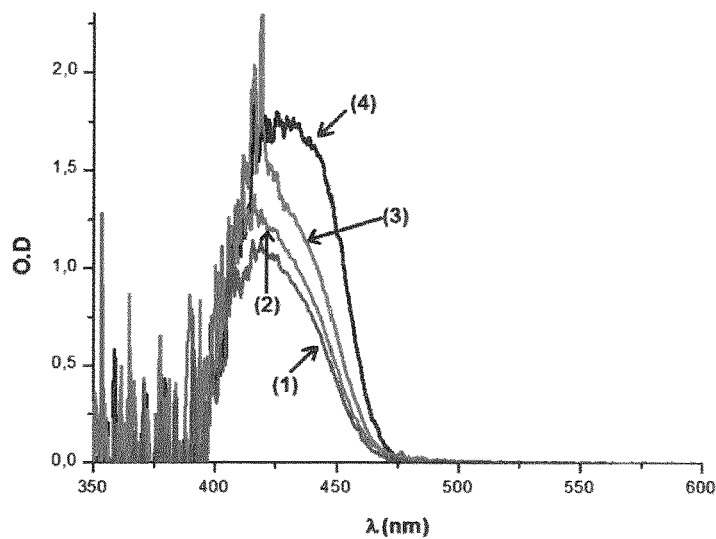
Figure 23:
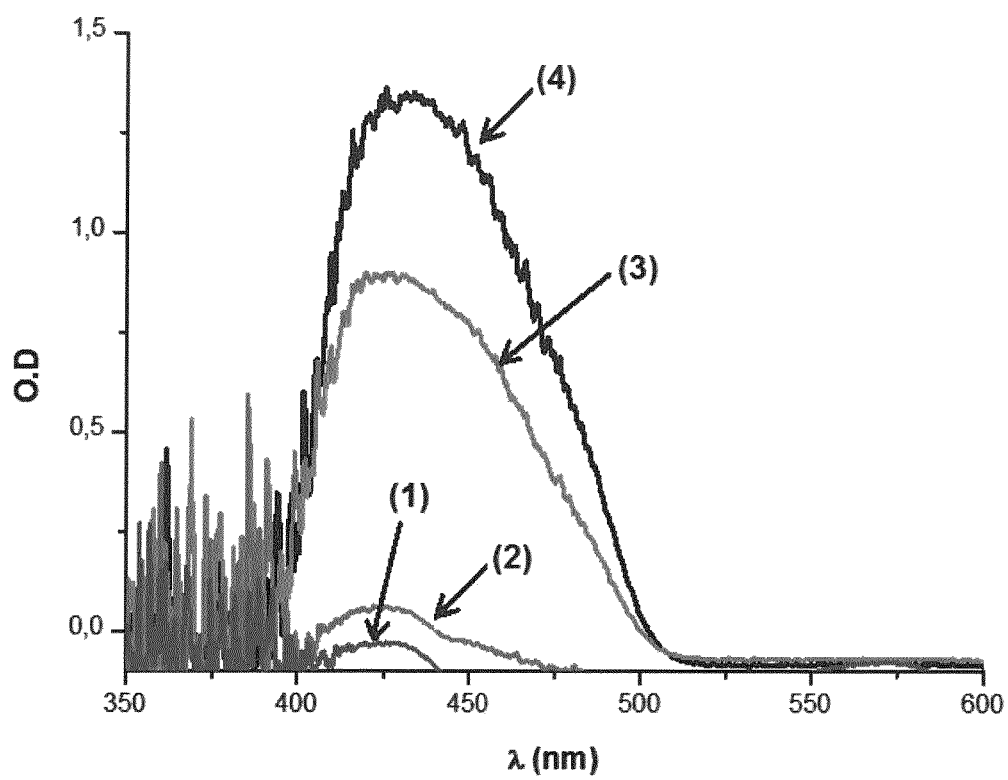

FIGS. 22 and 23 show absorption spectra obtained from steady state photolysis of UDMA polymerized with the photoinitiator 2% w/w bis-(benzoyl) diethylgermane (BBG) (cf. FIG. 22) or DKSi (cf. FIG. 23) under air upon the exposure to LED at 477 nm with SmartLite® Focus in samples of a thickness of 1.4 mm. The absorption spectra were recorded at the following different times of irradiation:

Curve (1): 60 s,
curve (2): 40 s,
curve (3): 20 s, and
curve (4): 0 s.

Figure 24:
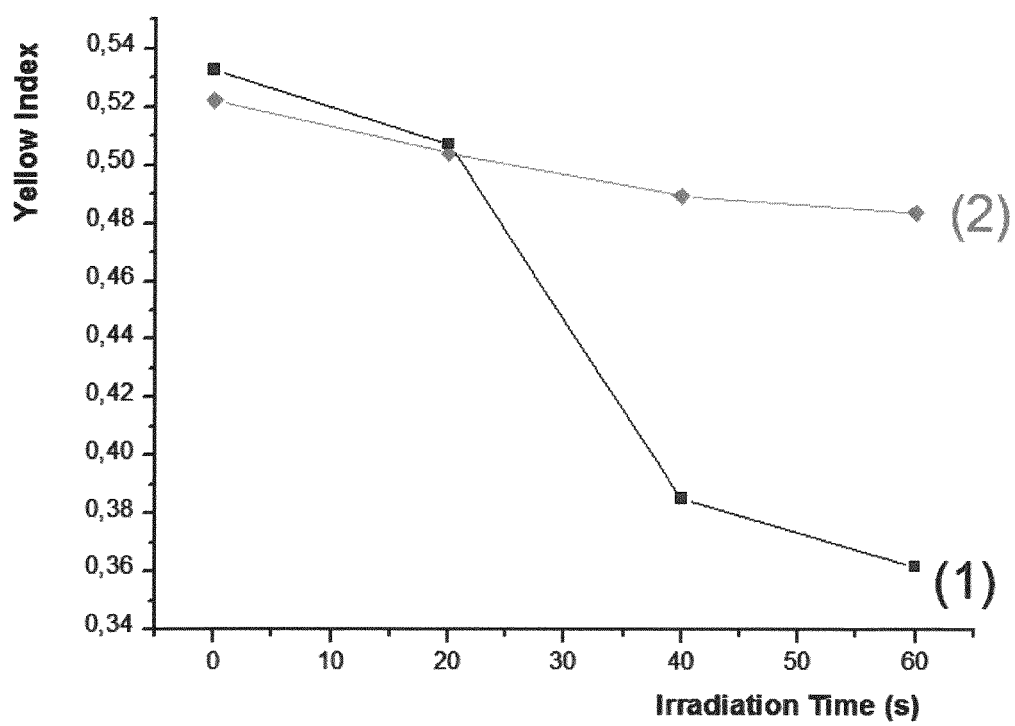

FIG. 24 shows the change of the yellow index in correlation with the irradiation time for the photopolymerization system described for FIGS. 22 and 23 for the following different photoinitiators:

Curve (1): DKSi (2% w/w); and
curve (2): BBG (2% w/w).

Figure 25:
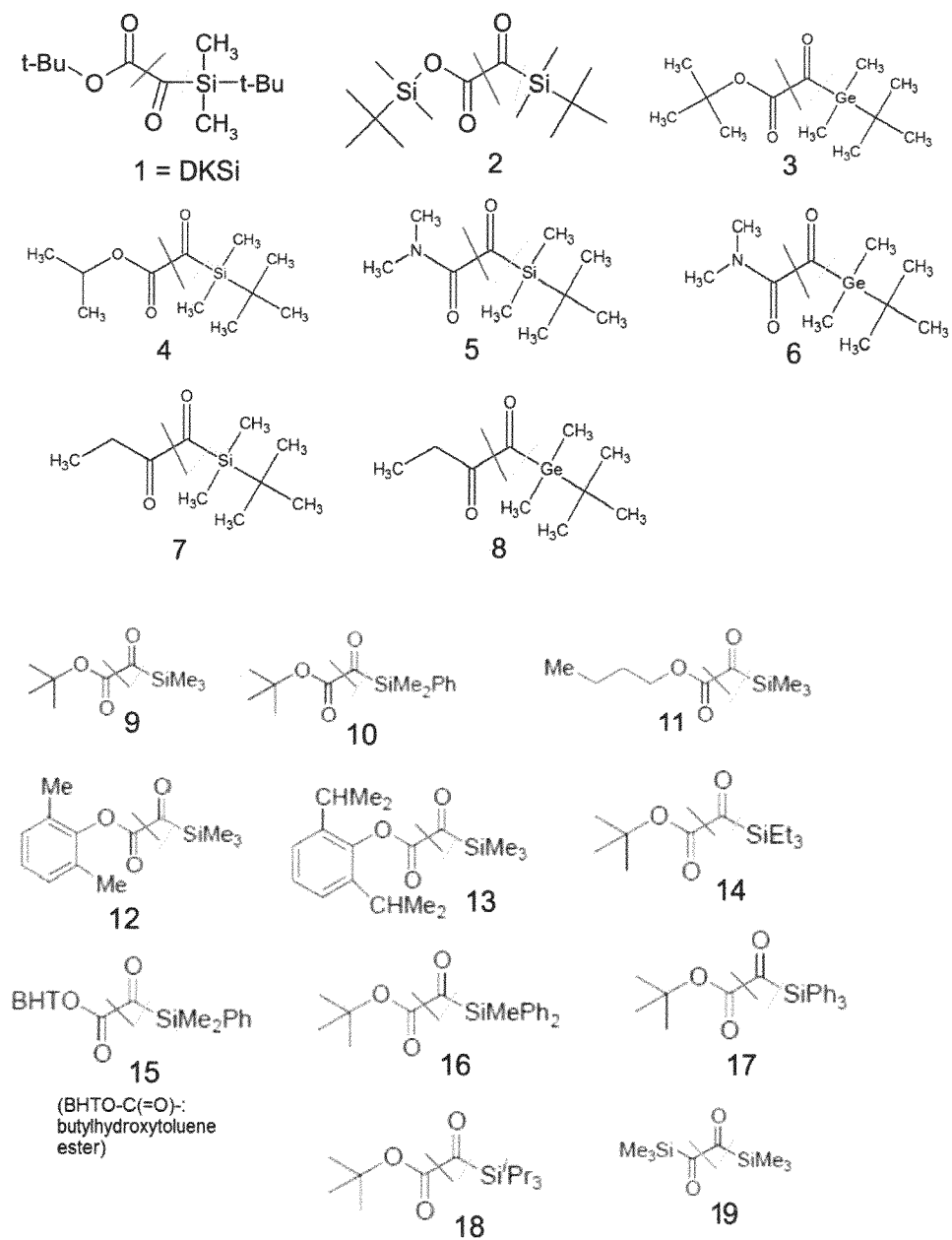

FIG. 25 shows the structural formulae of molecules 1 to 19 for which molecular modelling was carried out. In the structural formulae, it is indicated which bonds (Si—C═O, Ge—C═O and/or O═C—R) may be cleaved upon exposure to irradiation.

DETAILED DESCRIPTION OF PREFERRED EMBODIMENTS

The term "polymerization" relates to the combining by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as networks. In case of a higher conversion rate of the polymerizable monomer, the amount of multifunctional monomers may be reduced or the leaching problem may be alleviated.

The terms "curing" and "photocuring" mean the polymerization of functional oligomers and monomers, or even polymers, into a crosslinked polymer network. Curing is the polymerization of unsaturated monomers or oligomers in the presence of crosslinking agents.

The terms "photocurable" and "curable" refer to a dental composition that will polymerize into a crosslinked polymer network when irradiated for example with actinic radiation such as ultraviolet (UV), visible, or infrared radiation.

The term "quantum yield" is used herein to indicate the efficiency of a photochemical process. More particularly, quantum yield is a measure of the probability of the excitation of a particular molecule after absorption of a light quantum. The term expresses the number of photochemical events per photon absorbed.

"Actinic radiation" is any electromagnetic radiation that is capable of producing photochemical action and can have a wavelength of at least 150 nm and up to and including 1250 nm, and typically at least 300 nm and up to and including 750 nm.

The term "polymerizable double bound" as used herein in connection with compound(s) (a) and compound(s) (b4) means any double bond capable of radical polymerization, preferably a carbon-carbon double bond. Examples of the polymerizable double bond include vinyl, conjugated vinyl, allyl, acryl, methacryl and styryl. More preferably, the polymerizable double bound is selected from the group consisting of acryl, methacryl and styryl. Acryl and methacryl may be (meth)acryloyl or (meth)acrylamide. Most preferably, for the compound(s) (a), the polymerizable double bound is acryl or methacryl, and for the compound (b4), the polymerizable double bond with which groups $R^5$, $R^6$ Ar and L may be substituted is styryl.

The term "polymerization initiator system" refers to a system comprising at least (b1) a compound of formula (I). Optionally, the polymerization initiator system may further comprise at least one compound selected from the group consisting of (b2) a coinitiator, (b3) electron donor, an iodonium salt, a sulfonium salt and a phosphonium salt, and (b4) an aromatic tertiary phosphine compound.

The term "coinitiator" refers to a molecule that produces a chemical change in another molecule such as a photoinitiator in a photochemical process, or to a photoinitiator other than compound of formula (I). The coinitiator may be a photoinitiator or an electron donor.

The term "photoinitiator" is any chemical compound that forms free radicals when activated, e.g. by exposure to light or interaction with a coinitiator in a photochemical process. For example, the compound of formula (I) represents a photoinitiator.

The term "electron donor" as used herein means a compound which is capable of donating electrons in a photochemical process. Suitable examples include organic compounds having heteroatoms with electron lone pairs, for example amine compounds.

The ordinate axis label "O.D." in FIGS. 20, 22 and 23 means optical density, which is an arbitrary unit.

The present invention relates to a dental composition. The dental composition may be a dental restorative or dental prosthetic composition. More preferably, the dental composition is selected from the group consisting of a dental adhesive composition, a dental composite composition, a resin modified dental cement, a pit and fissure sealer, a desensitizer and a varnish. The dental composition may be cured by irradiation of actinic radiation.

The dental composition comprises (a) one or more compounds having at least one polymerizable double bond. The one or more compounds having a polymerizable double bond may preferably be polymerizable N-substituted alkyl acrylic or acrylic acid amide monomers or a (meth)acrylate compounds.

A polymerizable N-substituted alkyl acrylic or acrylic acid amide monomer may be preferably selected from compounds of the following formulae (A), (B) and (C):

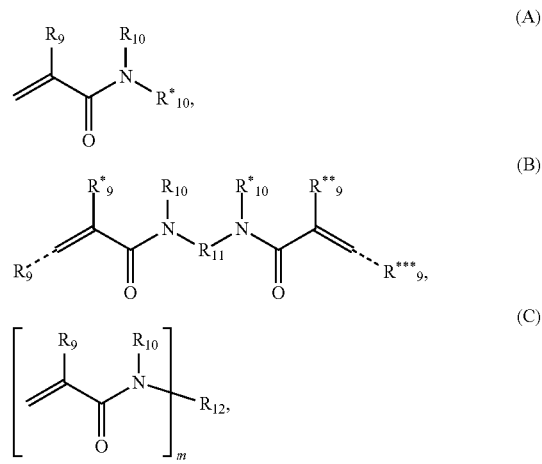

wherein $R_9$, $R^*_9$, $R^{}_9$, $R^{*}_9$ independently represent a hydrogen atom, —COOM, a straight chain or branched $C_1$ to $C_{18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{10}$ and $R^*_{10}$ independently represent a hydrogen atom, a straight chain or branched $C_1$ to $C_{18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, or a $C_5$ to $C_{18}$ aryl or $C_3$ to $C_{18}$ heteroaryl group which may be substituted by —COOM, —PO$_3$M, —O—PO$_3$M$_2$ or —SO$_3$M, $R_{11}$ represents a divalent substituted or unsubstituted organic residue having from 1 to 45 carbon atoms, whereby said organic residue may contain from 1 to 14 carbonyl groups or heteroatoms selected from oxygen, nitrogen and sulphur; preferably $R_{11}$ is a $C_1$ to $C_{18}$ alkylene group or a $C_2$ to $C_{18}$ alkenylene group, which may contain 1 to 6 carbonyl groups or heteroatoms selected from oxygen, nitrogen and sulfur, and which may be substituted by a hydroxyl group, a $C_{6-14}$ aryl group, —COOM, —PO$_3$M, —O—PO$_3$M$_2$ or —SO$_3$M, wherein in said $C_1$ to $C_{18}$ alkylene group and said $C_2$ to $C_{18}$ alkenylene group, from 1 to 6 —CH$_2$— groups may be replaced by a —N—(C=O)—CR$_z$=CH$_2$ group wherein $R_z$ is a hydrogen atom or a $C_1$ to $C_{18}$ alkyl group, a substituted or unsubstituted $C_3$ to $C_{18}$ cycloalkyl group, a substituted or unsubstituted $C_4$ to $C_{18}$ aryl or heteroaryl group, a substituted or unsubstituted $C_5$ to $C_{18}$ alkylaryl or alkylheteroaryl group, a substituted or unsubstituted $C_7$ to $C_{30}$ aralkyl group, and a substituted or unsubstituted $C_2$ to $C_{45}$ mono-, di- or polyether group having from 1 to 14 oxygen atoms, $R_{12}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one $R_9$, $R^*_9$, $R^{}_9$, $R^{*}_9$, $R_{10}$, $R^*_{10}$, $R_{11}$ and $R_{12}$, which M are independent from each other, each represent a hydrogen atom or a metal atom.

For $R_9$, $R^*_9$, $R^{}_9$ and $R^{*}_9$, the straight chain or branched $C_1$ to $C_{18}$ alkyl group may e.g. be methyl, ethyl, n-propyl, i-propyl, n-butyl, isobutyl, tert-butyl, sec-butyl, pentyl or hexyl. For $R_{10}$ and $R^*_{10}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_9$, $R^*_9$, $R^{}_9$, $R^{*}_9$, $R_{10}$ and $R^*_{10}$, an aryl group may, for example, be a phenyl group or a naphthyl group, and a $C_{3-14}$ heteroaryl group may contain 1 to 3 heteroatoms selected from nitrogen, oxygen and sulfur.

In formula (B), the dotted bond indicates that $R_9$ and $R^{***}_9$ may be in cis or trans configuration relative to CO.

Preferably, in formula (B), $R_9$, $R^*_9$, $R^{}_9$ and $R^{*}_9$ independently represent a hydrogen atom, —COOM, a straight chain or branched $C_{1-16}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl or $C_{3-14}$ heteroaryl group which may be substituted by —COOM, —PO$_3$M, —O—PO$_3$M$_2$ or —SO$_3$M. More preferably, in formula (B), $R_9$, $R^*_9$, $R^{}_9$ and $R^{*}_9$ independently represent a hydrogen atom, a straight chain or branched $C_{1-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_9$, $R^*_9$, $R^{}_9$ and $R^{*}_9$ independently represent a hydrogen atom, a straight chain or branched $C_{1-4}$ alkyl group which may be substituted by a cyclohexyl group or a phenyl group, or a cyclohexyl group which may be substituted by a $C_{1-4}$ alkyl group. Most preferably, $R_9$, $R^*_9$, $R^{}_9$ and $R^{*}_9$ independently represent a hydrogen atom or a straight chain or branched $C_{1-4}$ alkyl group.

Preferably, in formula (B), $R_{10}$ and $R^*_{10}$ independently represent a hydrogen atom, a straight chain or branched $C_{1-16}$ alkyl group or $C_{2-16}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M, a $C_{3-6}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M, a $C_{6-14}$ aryl or $C_{3-14}$ heteroaryl group which may be substituted by —COOM, —PO$_3$M, —O—PO$_3$M$_2$ or —SO$_3$M. More preferably, $R_{10}$ and $R^*_{10}$ independently represent a hydrogen atom, a straight chain or branched $C_{1-10}$ alkyl or $C_{2-10}$ alkenyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{10}$ and $R^*_{10}$ independently represent is a hydrogen atom, a straight chain or branched $C_{1-10}$ alkyl group or $C_{2-10}$ alkenyl group which may be substituted by a cyclohexyl group or a phenyl group, or a cyclohexyl group which may be substituted by a $C_{1-4}$ alkyl group. Yet even more preferably, $R_{10}$ and $R^*_{10}$ represent an unsubstituted $C_{1-10}$ alkyl group or $C_{2-10}$ alkenyl group, still even more preferably an unsubstituted $C_{2-6}$ alkyl group or $C_{3-6}$ alkenyl group, and most preferably an ethyl group or an allyl group.

Particular preferred mono- or bis- or (meth)acrylamides and poly[(meth) acrylamides] have the following formulae:

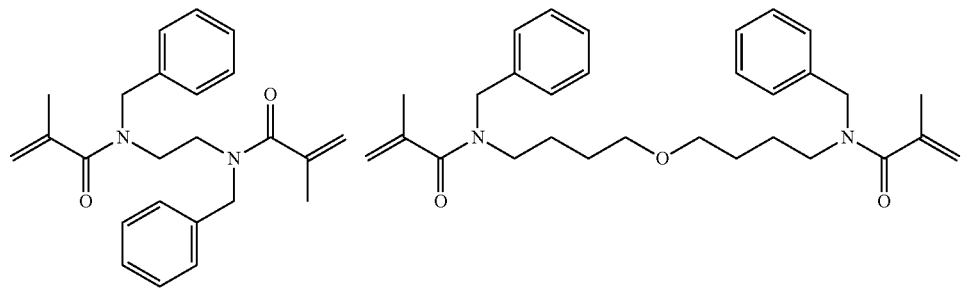

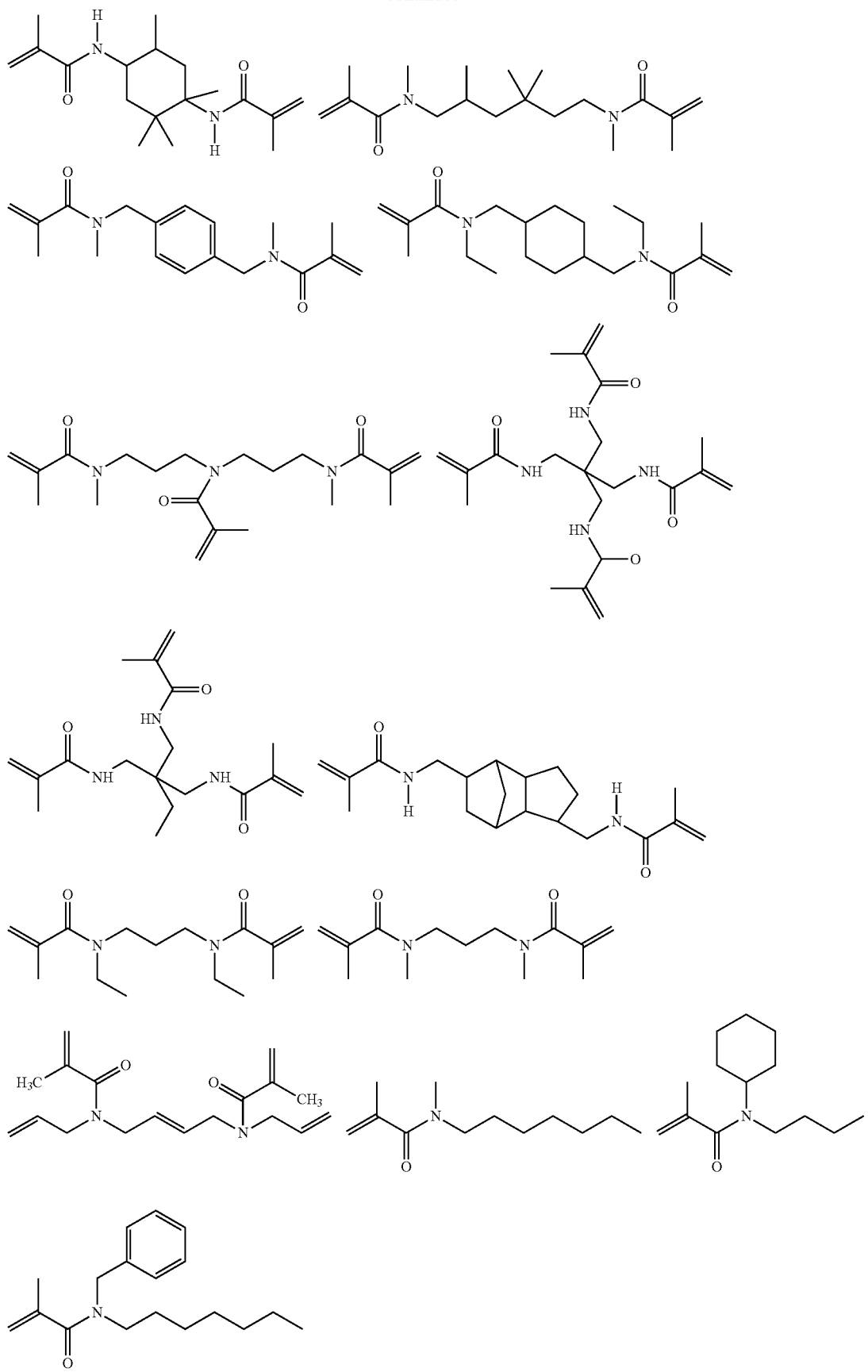

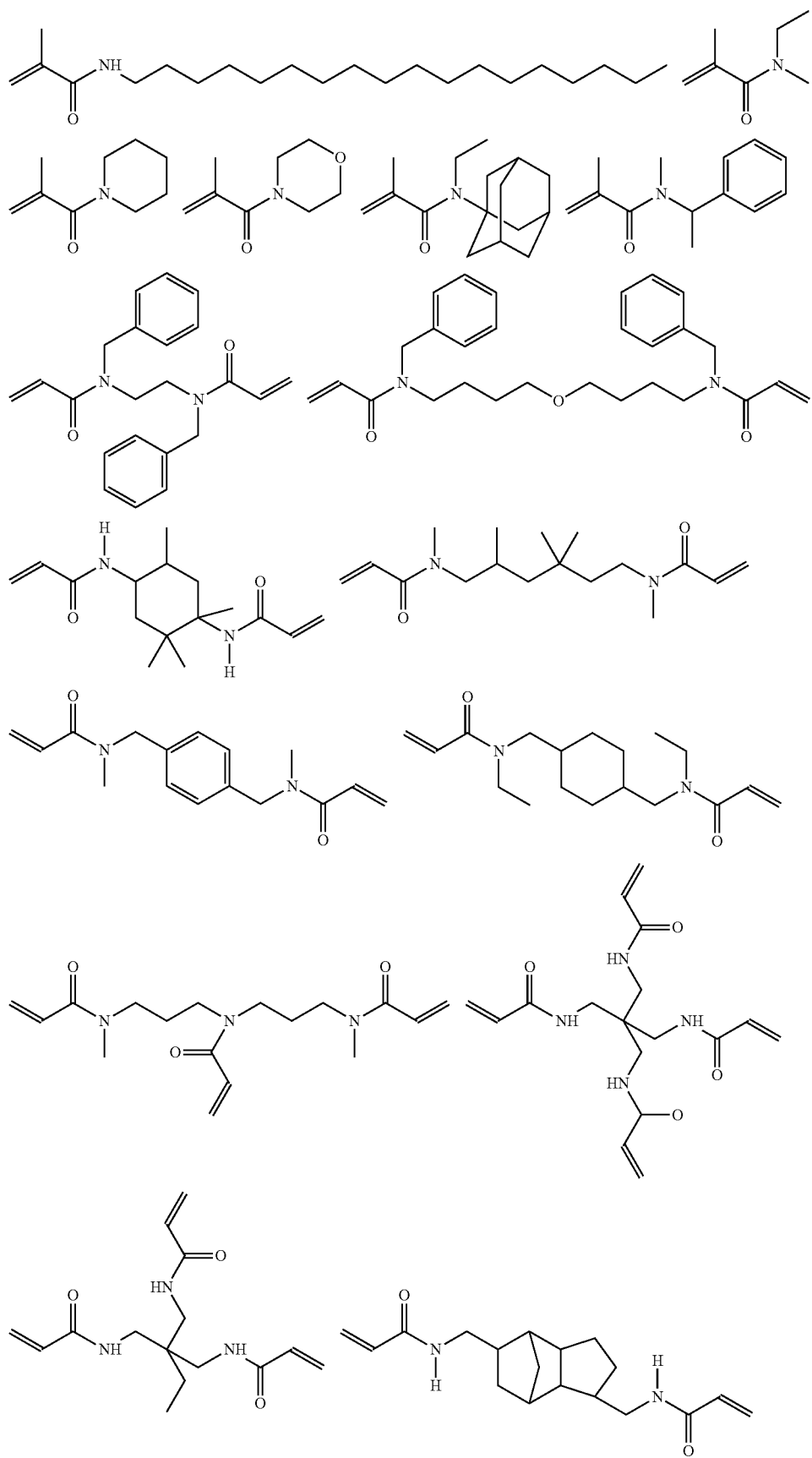

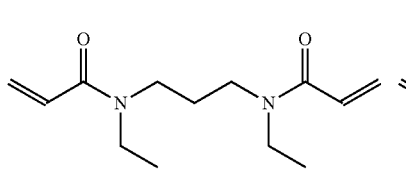
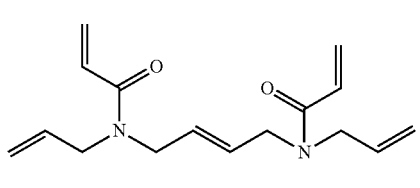
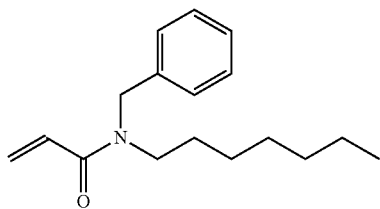
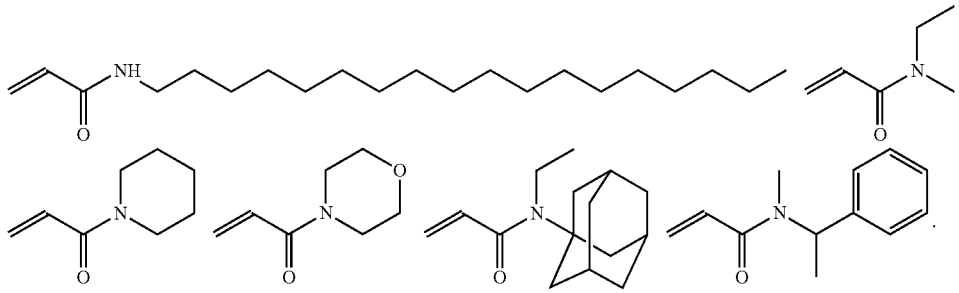

Most preferred are the bis-(meth)acrylamides:
N,N'-diallyl-1,4-bisacrylamido-(2E)-but-2-en (BAABE) having the structural formula

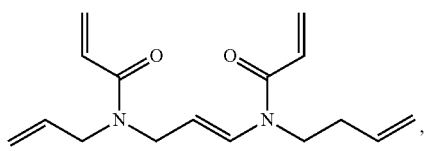 [SMILES: C=CCCN(/C=C/CN(CC=C)C(=O)C=C)C(=O)C=C]

and N,N'-diethyl-1,3-bisacrylamido-propan (BADEP) having the structural formula

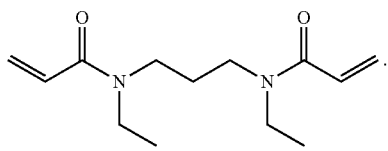 [SMILES: C=CC(=O)N(CC)CCCN(CC)C(=O)C=C]

Other suitable examples of polymerizable compounds having a polymerizable double bond are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

A (meth)acrylate compound may be selected from the group of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, the diglycidyl methacrylate of bis-phenol A ("bis-GMA"), 11,14-dioxa-2,9-diazaheptadec-16-enoicacid, 4,4,6,16 (or 4,6,6,16)-tetramethyl-10,15-dioxo-,2-[(2-methyl-1-oxo-2-propen-1-yl)oxy]ethyl ester (UDMA), glycerol mono- and di-acrylate, glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethyloi propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexy carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl 4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane, may be mentioned. Other suitable examples of polymerizable components are isopropenyl oxazoline, vinyl azalactone, vinyl pyrrolidone, styrene, divinylbenzene, urethane acrylates or methacrylates, epoxy acrylates or methacrylates and polyol acrylates or methacrylates.

It is preferred to select polymerizable compounds having a polymerizable double bond with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, particularly preferred are polymerizable compounds having a polymerizable double bond which do not comprise an ester group. That is, for acidic dental compositions, (meth)acrylates are preferably excluded.

It is preferred that at least one of the polymerizable compounds having at least one polymerizable double bond has an acidic group. This acidic group is preferably selected from a carboxylic acid group, a sulfonic acid ester group, a phosphonic acid ester group and a phosphoric acid ester group.

Phosphoric acid ester group containing polymerizable compounds having at least one polymerizable double bond preferably have the following formula (D):

wherein
the moieties Y independent from each other represent a hydrogen atom or
a moiety of the following formulae (Y*), (Y) or (Y*):

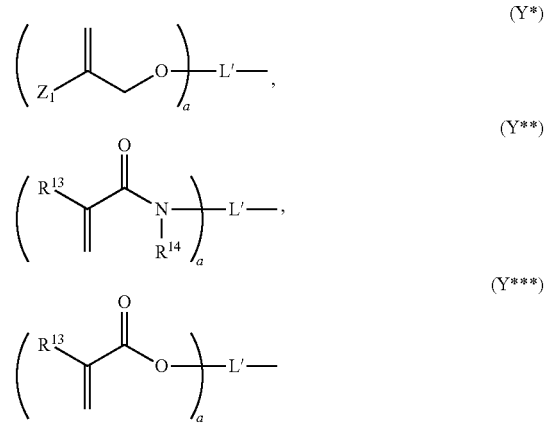

wherein
$Z_1$ is $COOR^\alpha$, $COSR^\beta$, $CON(R^\alpha)_2$, $CONR^\alpha R^\beta$, or $CONHR^\alpha$, wherein $R^\alpha$ and $R^\beta$ independently represent a hydrogen atom, a $C_{1-18}$ alkyl group optionally substituted by a $C_{3-8}$ cycloalkyl group, an optionally substituted $C_{3-8}$ cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby two $R^\alpha$ residues may form together with the adjacent nitrogen atom to which they are bound a 5- to 7-membered heterocyclic ring which may contain further nitrogen atoms or an oxygen atoms, and whereby the optionally substituted groups may be substituted by 1 to 5 $C_{1-5}$ alkyl group(s);

$R^{13}$ and $R^{14}$ independently represent a hydrogen atom, an optionally substituted $C_{1-18}$ alkyl group, an optionally substituted $C_{3-18}$ cycloalky group, an optionally substituted $C_{5-18}$ aryl or heteroaryl group, an optionally substituted $C_{5-18}$ alkylaryl or alkylheteroaryl group, an optionally substituted $C_{7-30}$ aralkyl group, whereby the optionally substituted groups may be substituted by 1 to 5 $C_{1-5}$ alkyl group(s);

L* represents an (a+b)-valent organic residue (whereby b is 1 when Y in formula (D) is within the round brackets) containing 2 to 45 carbon atoms and optionally heteroatoms such as oxygen, nitrogen and sulfur atoms, the carbon atoms including a+b carbon atoms selected from primary and secondary aliphatic carbon atoms, secondary alicyclic carbon atoms, and aromatic carbon atoms, each of the a+b carbon atoms linking a phosphate or a moiety of any one of formula (Y*), (Y) and (Y*); a is an integer of from 1 to 10, preferably 1 to 5; b is an integer of from 1 to 10, preferably 1 to 5; provided that at least one Y is not hydrogen. The preparation of such compounds wherein Y=Y* is known from EP-A 1 548 021.

Furthermore, the polymerizable monomer having one or more acidic groups may be selected from:

1) phosphonic acid group containing polymerizable acidic compounds of the following formula (E):

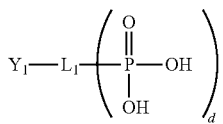
(E)

wherein
the moiety $Y_1$ represents a moiety of the following formulae $(Y_1^*)$, $(Y_1^{})$ or $(Y_1^{*})$:

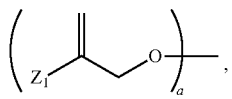
$(Y_1^*)$

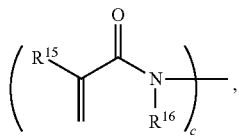
$(Y_1^{**})$

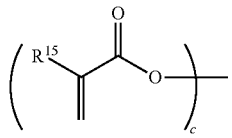
$(Y_1^{***})$ $Z_2$ independently has the same meaning as defined for $Z_1$;
$R^{15}$ and $R^{16}$ independently have the same meaning as defined for $R^{13}$ and $R^{14}$;
$L_1$ represents a (c+d) valent organic residue containing 2 to 45 carbon atoms and optionally heteroatoms such as oxygen, nitrogen and sulfur, the carbon atoms including c+d carbon atoms selected from primary and secondary aliphatic carbon atoms, secondary alicyclic carbon atoms, and aromatic carbon atoms, each of the c+d carbon atoms linking a phosphonate or a moiety of any one of formula $(Y_1^*)$, $(Y_1^{})$ and $(Y_1^{*})$; and
c and d independently represent integers of from 1 to 10; and/or 2) sulfonic acid group containing polymerizable acidic compounds of the following formula (E):

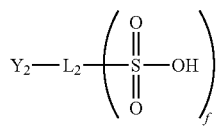
(F)

wherein
the moiety $Y_2$ represents a moiety of the following formulae $(Y_2^*)$, $(Y_2^{})$ or $(Y_2^{*})$:

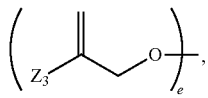
$(Y_2^*)$

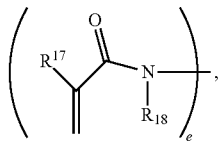
$(Y_2^{**})$

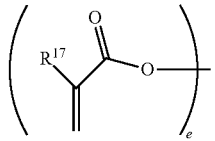
$(Y_2^{***})$ $Z_3$ independently has the same meaning as defined for $Z_1$;
$R^{17}$ and $R^{18}$ independently have the same meaning as defined for $R^{13}$ and $R^{14}$;
$L_2$ represents an (e+f) valent organic residue containing 2 to 45 carbon atoms and optionally heteroatoms such as oxygen, nitrogen and sulfur atoms, the carbon atoms including e+f carbon atoms selected from primary and secondary aliphatic carbon atoms, secondary alicyclic carbon atoms, and aromatic carbon atoms, each of the e+f carbon atoms linking a sulphonate or a moiety of any one of formula $(Y_2^*)$ $(Y_2^{**})$ and $(Y_2^*)$; and e and f independently represent an integer of from 1 to 10.

It is preferred to select compounds of formula (D), (E) and (F) with the proviso that they do not contain ester groups, or at least only ester groups which do not significantly hydrolyze in aqueous media at pH 3 at room temperature within one month, such as the phosphoric acid ester group of compounds of formula (D). Thereby, an advantageous stability of an acidic dental composition, that is a composition having a pH of less than 7, in terms of shelf-life stability of the uncured dental composition as well as stability after curing in the mouth of a patient is ensured. Therefore, particularly preferred are compounds of formula (D) excluding the moiety of formula $Y^{***}$ and the moiety of formula $Y^*$ wherein $Z_1$ is $COOR^\alpha$ or $COSR^\beta$, compounds of formula (E) excluding the moiety of formula $Y_1^{***}$ and the moiety of formula $Y_1^*$ wherein $Z_2$ is $COOR^\alpha$ or $COSR^\beta$ as well as compounds of formula (F) excluding the moiety of formula $Y_2^{***}$ and the moiety of formula $Y_2^*$ wherein $Z_3$ is $COOR^\alpha$ or $COSR^\beta$.

From the phosphoric acid ester group containing polymerizable compound having at least one polymerizable double bond, compounds of formula (D') characterized by one of the following formulae are particularly preferred:

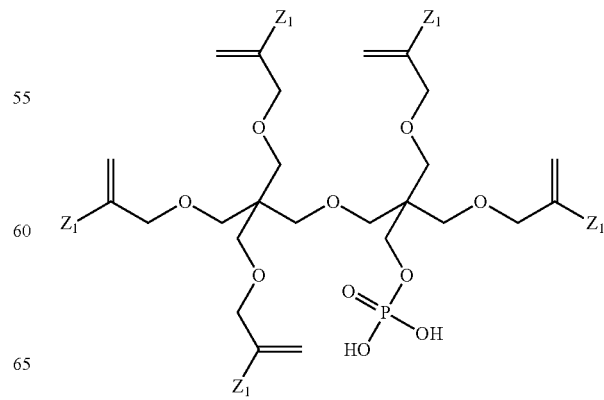

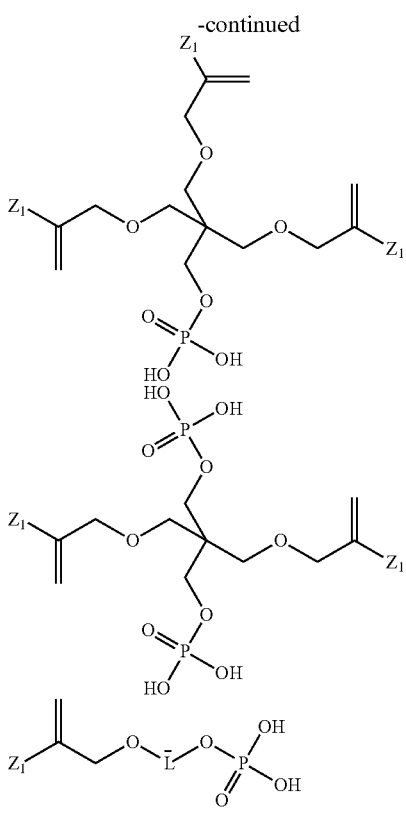

wherein $Z_1$ is defined as above, and L* is an optionally substituted alkylene group. More preferably, $Z_1$ is methyl, and L* is a $C_4$ to $C_{16}$ alkylene group. Even more preferably, L* is a $C_8$ to $C_{12}$ alkylene group.

From the sulfonic acid group containing polymerizable compound having at least one polymerizable double bond, compounds of formula (XI') characterized by one of the following formulae are particularly preferred:

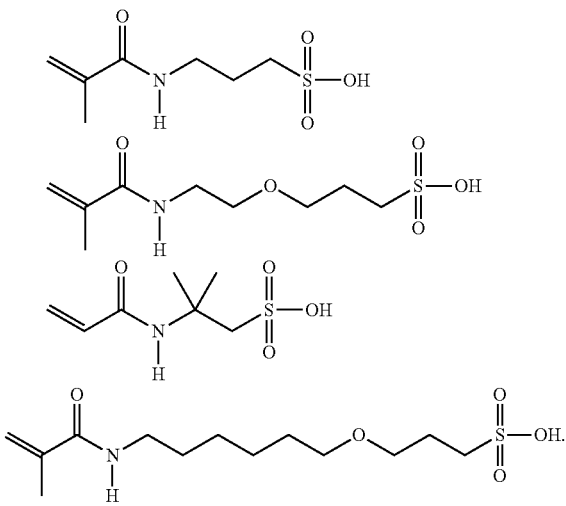

In a particularly preferred embodiment, according to (a), the dental composition according to the present invention contains at least one polymerizable compound having at least one (meth)acryl moiety and optionally at least one polymerizable compound having a polymerizable double bond and an acidic group, more preferably at least one polymerizable compound of formula (A), (B) or (C) described above and optionally at least one polymerizable compound of formula (D), (E) or (F) described above.

Carboxylic acid group containing polymerizable compounds having at least one polymerizable double bond may be selected e.g. from acrylic acid and methacrylic acid.

Preferably, the one or more compounds having a polymerizable double bond each contain one or two radical-polymerizable groups.

It is preferable that a blending ratio of the one or more compounds having a polymerizable double bond to the entire dental composition is 5 to 80% by weight. More preferably, the blending ratio is 10 to 60% by weight.

The dental composition further comprises (b) a polymerization initiator system comprising (b1) a compound of formula (I). The dental composition may comprise one or more compound(s) of formula (I).

The compound (b1) has the following formula (I):

In formula (I), X is an acylsilyl or acylgermanyl group of the following formula (II):

In formula (II), M is Si or Ge, $R^1$ and $R^2$ independently from each other represent a substituted or unsubstituted hydrocarbyl or hydrocarbylcarbonyl group, and $R^3$ represents a substituted or unsubstituted hydrocarbyl group.

R of formula (I) may (i) have the same meaning as X, whereby the compound of formula (I) may be symmetrical or unsymmetrical, (ii) be a group of formula (III), or (iii) when M is Si, R may be a substituted or unsubstituted hydrocarbyl group.

The group of formula (III) has the following structural formula:

In the group of formula (III), Y represents a single bond, an oxygen atom or a group NR', wherein R' represents a substituted or unsubstituted hydrocarbyl group. $R^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

It was surprisingly found that compounds of formula (I) represent polymerization initiators which are particularly suitable for dental compositions. With compounds of formula (I), a high polymerization efficiency is attained, and no coloration problems occur, or in a polymerization system comprising a conventional photoinitiator such as camphor quinone, coloration is efficiently suppressed. Furthermore, compounds of formula (I) have a light absorption within the wavelength range typically applied in dental application, they are compatible with the ingredients of dental compositions and besides, they are considered physiologically harmless.

In connection with compound of formula (I), the term "substituted" as used herein means that $R^1$, $R^2$, $R^3$, $R^4$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^1$, $R^2$ and $R^3$ are substituted, then it is preferred that they are substituted with 1 to 3 substituents, more preferably with 1 substituent.

In the compound of formula (I), moieties $R^1$, $R^2$ and $R^3$ may be defined as follows:

$R^1$ and $R^2$ independently from each other represent a substituted or unsubstituted hydrocarbyl or hydrocarbylcarbonyl group, and $R^3$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a C3-8 cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(–) group can for example, include methylcyclopropyl(–) methylcyclobutyl(–), methylcyclopentyl(–), methylcyclohexyl(–), ethylcyclopropyl(–), ethylcyclobutyl(–), ethylcyclopentyl(–), ethylcyclohexyl(–), propylcyclopropyl (–), propylcyclobutyl(–), propylcyclopentyl(–), propylcyclohexyl(–).

An arylalkyl(–) group may be a $C_{7-20}$ arylalkyl(–) group, typically a combination of a linear or branched alkyl group having 1 to 6 carbon atoms and an aryl(–) group having 6 to 10 carbon atoms. Specific examples of an arylalkyl(–) group are a benzyl(–) group or a phenylethyl(–) group.

An aryl group can include aryl groups having 6 to 10 carbon atoms. Examples of the aryl group are phenyl and naphtyl.

The hydrocarbylcarbonyl groups of $R^1$ and $R^2$ represent acyl groups ($R_{org}$—(C=O)—) in which the organic residue $R_{org}$ is a hydrocarbyl residue as defined above.

Compound of formula (I) may contain one or two hydrocarbylcarbonyl groups, that is either one of $R^1$ or $R^2$ is a hydrocarbylcarbonyl group, or both $R^1$ and $R^2$ are hydrocarbylcarbonyl groups. Preferably, compound of formula (I) contains one hydrocarbylcarbonyl group.

Preferably, the hydrocarbylcarbonyl group is an arylcarbonyl group, more preferably a benzoyl group.

Preferably, $R^1$ and $R^2$ are independently selected from the group consisting of a straight chain or branched $C_{1-6}$ alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-6}$ alkyl group or a phenyl group.

Most preferably, $R^1$ and $R^2$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^3$ is a straight chain or branched $C_{1-4}$ alkyl group.

In the compound of formula (I), R may have the same meaning as X, whereby the compound of formula (I) may be symmetrical or unsymmetrical. Alternatively, R may represent a substituted or unsubstituted hydrocarbyl group, or a group of formula (III). Preferably, if R has the same meaning as X, then compound of formula (I) is unsymmetrical. If R represents a substituted or unsubstituted hydrocarbyl group, then the hydrocarbyl group has the same meaning as defined above for $R^1$ and is independently selected therefrom.

In the group of formula (III) of compound of formula (I), $R^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group.

If $R^4$ of formula (III) is a trihydrocarbylsilylgroup, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^1$, $R^2$ and $R^3$ and is independently selected therefrom.

In formula (III), R' has the same meaning as defined for $R^3$ and is independently selected therefrom.

If M is Si in compound of formula (I), R may be also be a substituted or unsubstituted hydrocarbyl group, wherein the hydrocarbyl group has the same meaning as defined above for $R^3$ and is independently selected therefrom.

For example, compounds of formula (I) wherein R has the same meaning as X and which are symmetrical may be have the following structural formulae:

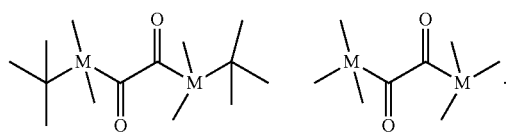

For example, compounds of formula (I) wherein R represents a group of formula (III) wherein Y is a bond, an oxygen atom or a NR' group, and $R^4$ represents a substituted or unsubstituted hydrocarbyl group may have the following structural formulae:

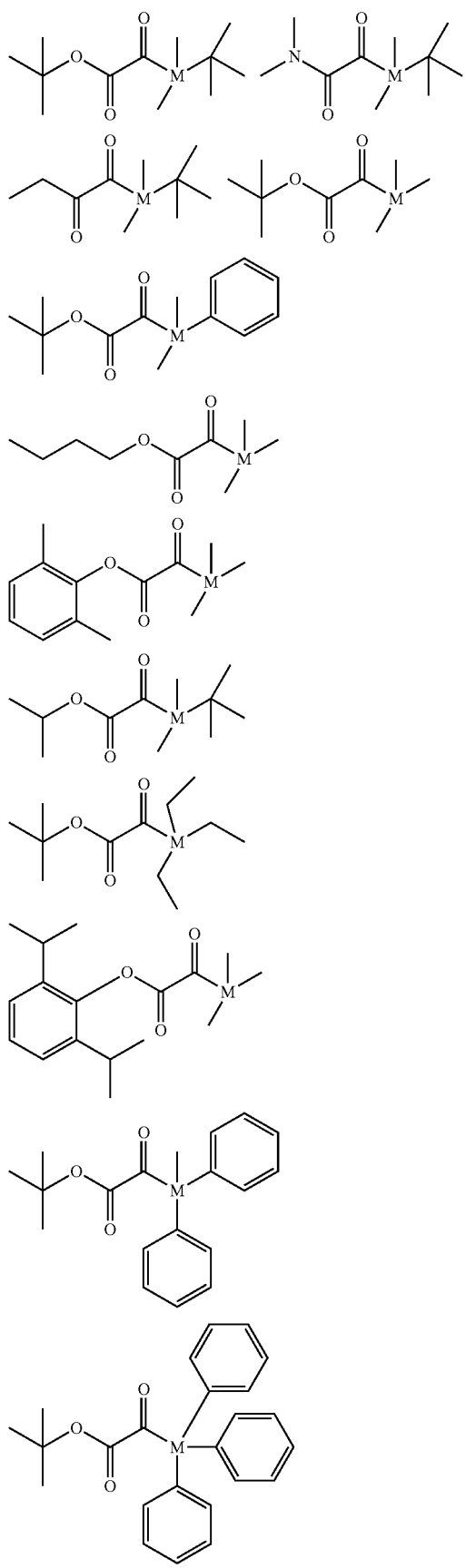
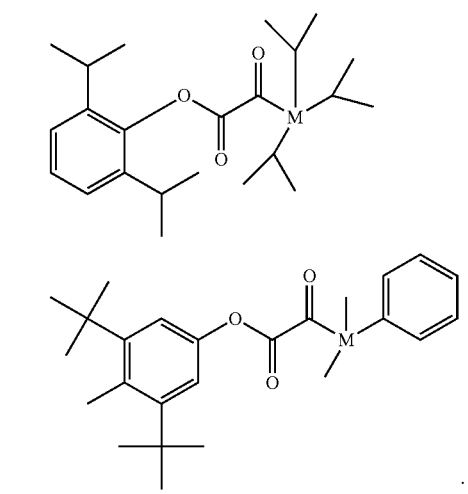
For example, compounds of formula (I) wherein R represents a group of formula (III) wherein $R^4$ represents a trihydrocarbylsilyl group have the following structural formulae:
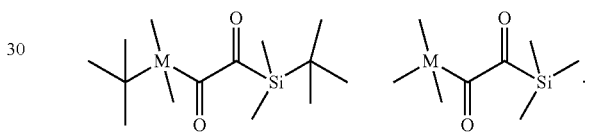
For example, compounds of formula (I) wherein M is Si and R represents a substituted or unsubstituted hydrocarbyl group, may have the following structural formulae:
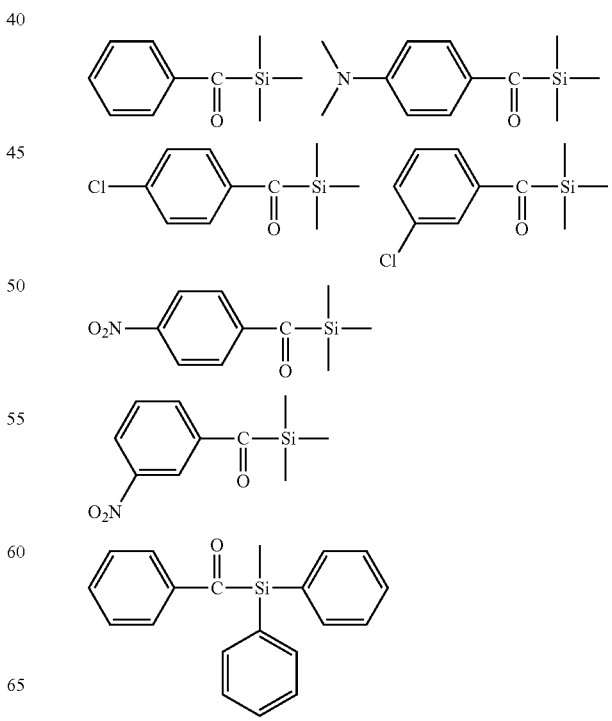

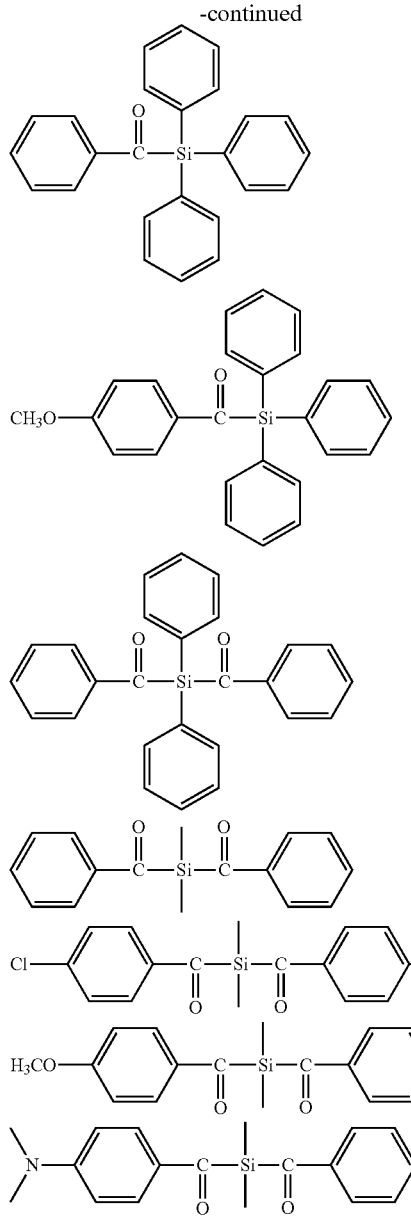

Preferably, compound of formula (I) is selected from the group consisting of:

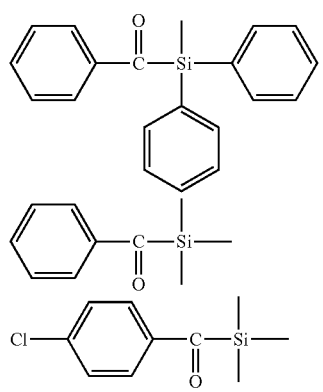

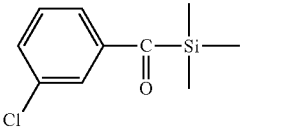
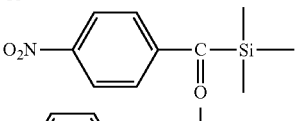
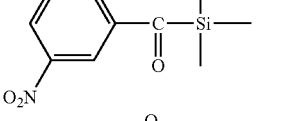
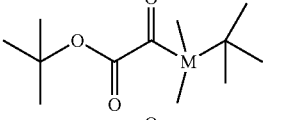
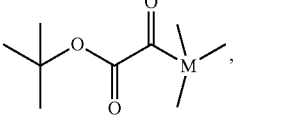

wherein compounds of formula (I) with M=Si are particularly preferred.

Most preferably, compound of formula (I) is selected from the group consisting of:

compound of formula (i) is selected from the group consisting of:

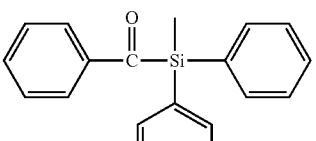
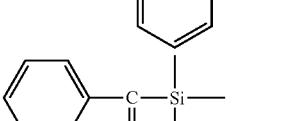
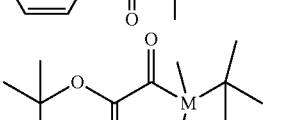
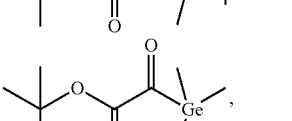
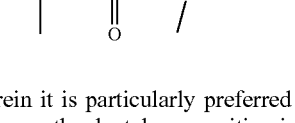

wherein it is particularly preferred that M=Si.

In case the dental composition is in the form of an acidic composition, that is a composition having a pH of less than 7, depending on the composition's pH level, it is preferred to select compounds of formula (I) with the proviso that they do not contain ester groups, or at least only ester groups which do not significantly hydrolyze in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are compounds of formula (I) excluding R being a group of formula (III) in which Y is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (I) may be a known compound which is commercially available or a may be prepared according to published procedures.

The compound of formula (I) wherein M is Si and R represents a substituted or unsubstituted hydrocarbyl group may for example be readily prepared by means of a one-step Pd-catalyzed reaction with a disilane as described e.g. by Yamamoto K. et al., *J. Tetrahedron Lett.*, 1980, vol. 21, pages 1653 to 1656:

Scheme 1: Preparation of acylsilanes

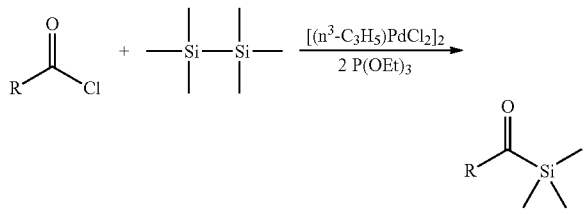

In Scheme 1, the reaction is exemplary depicted with hexamethylsilan as the disilane, whereby a compound of formula (I) wherein $R^1$, $R^2$ and $R^3$ represent a methyl group is obtained. It is understood that $R^1$, $R^2$ and $R^3$ can be varied by applying disilanes having hydrocarbon substituents other than methyl.

The compound of formula (I) wherein R represents a group of formula (III) in which Y is an oxygen atom and $R^4$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyltrifluoromethane-sulfonate to obtain a trihydrocarbylsilyldiazoacetate, which is finally reacted with potassium peroxymonosulfate to arrive at the target compound:

Scheme 2: Preparation of silylglyoxylates

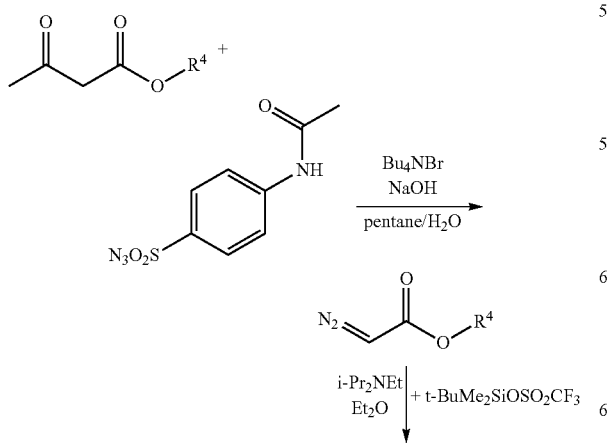

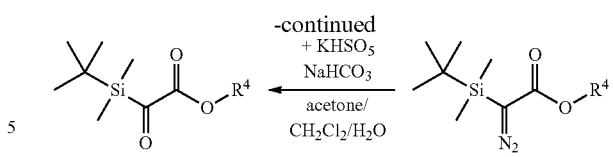

In Scheme 2, the reaction is exemplary depicted for obtaining a compound of formula (I) wherein in X of formula (II), $R^1$ and $R^2$ represent a methyl group, and $R^3$ represents a tert-butyl group. It is understood that $R^1$, $R^2$ and $R^3$ can be varied by applying a trihydrocarbylsilyltrifluoromethane-sulfonate other than t-BuMeSiOSO$_2$CF$_3$. Alternatively, compounds of formula (I) wherein M is Si, R represents a group of formula (III) and Y represents an oxygen atom may be prepared by a single-pot three-component coupling reaction of a silylglyoxylate, a terminal alkyne and an aldehyde in the presence of ZnI$_2$ and Et$_3$N as described by Nicewicz D. A. in J. Am. Chem. Soc., 2005, 127 (17), pages 6170 to 6171. Further syntheses of silylglyoxylate compounds are described e.g. by Boyce G. R. et al. in *J. Org. Chem.*, 2012, 77 (10), pages 4503 to 4515 and Boyce G. R. et al. in Org. Lett., 2012, 14 (2), pages 652 to 655.

For example, the following compounds of formula (I) are known and commercially available, and their Chemical Abstracts (CAS) No. is given in brackets: benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1), (4-methoxybenzoyl) triphenylsilan (1174-56-7) and tert-butyl (tert-butyldimethylsilyl)glyoxylate (852447-17-7).

The compound of formula (I) wherein M of X is Ge and R represents a group of formula (III) in which Y is an oxygen atom and $R^4$ represents a hydrocarbyl group may for example be prepared by a two step synthesis starting from a trihydrocarbylgermanyltrifluoromethane-sulfonate such as trimethylgermane triflate. Such trimethylgermane triflate may be prepared starting from commercially available chlorotrimethylgermane as described by S. P. Mallela et al. in J. Fluorine Chem., 1989, vol. 44, issue 2, pages 309 to 328. As shown in Scheme 3 below, the trihydrocarbylgermanyltrifluoromethane-sulfonate and an azide compound are reacted to obtain a trihydrocarbylgermanyldiazoacetate, which is reacted with oxone (potassium peroxymonosulfate) to arrive at the target compound:

Scheme 3: Preparation of germanylglyoxylates

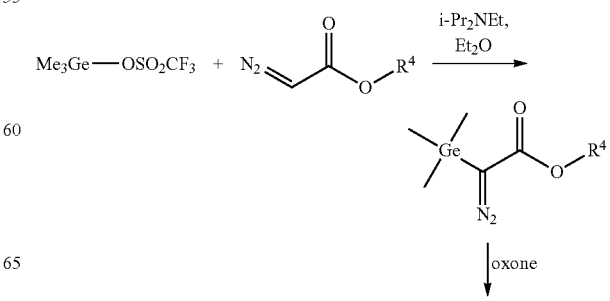

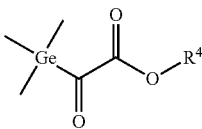

in Scheme 3, the reaction is exemplary depicted for obtaining a compound of formula (I) wherein in X of formula (II), $R^1$, $R^2$ and $R^3$ represent a methyl group. It is understood that $R^1$, $R^2$ and $R^3$ can be varied by applying a trihydrocarbylgermanyltrifluoromethane-sulfonate other than $Me_3Ge$—$OSO_2CF_3$.

All compounds of formula (I) comprise the group of formula (II)

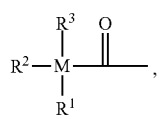

(II)

wherein M, $R_1$, $R_2$ and $R_3$ are defined as above. Depending on the selection of M, the group of formula (II) represents an acylsilane or acylgermane group. Upon exposure to UV-VIS-light, the bond between M and the acyl group may be cleaved, whereby a silyl/germanyl and an acyl radical is formed as a polymerization initiating structure, but in competition to the cleavage into to radicals, a carbene structure might be formed:

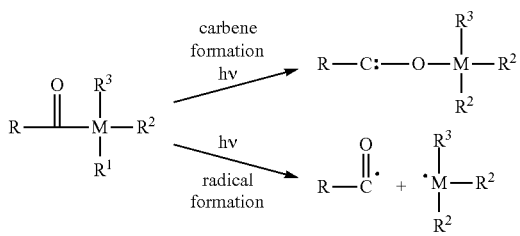

Scheme 4: carbene formation versus radical formation

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (I) wherein R has the same meaning as X or is a group of formula (III), the C—C bond of the 1,2-diketone moiety (—C(=O)—C(=O)—) may be cleaved upon exposure to UV-VIS-light into two acyl radicals. This cleavage is exemplary shown for compound of formula (I) wherein R is a group of formula (III) and Y is an oxygen atom, that is for a glyoxylate (—O—C=O)—C(=O)—) compound:

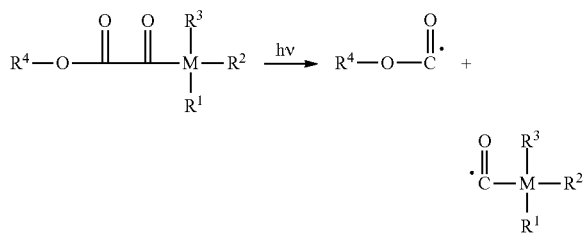

Scheme 5: cleavage of —O—C(=O)—C(=O)— moiety of a glyoxylate

Besides, in compound of formula (I), there is a third possibility for a radical cleavage in case R is a compound of formula (III) wherein Y is an oxygen atom and $R^4$ is a substituted or unsubstituted hydrocarbyl group. Namely, an intra- or intermolecular hydrogen abstraction might occur, where a hydrogen radical is abstracted:

Scheme 6: hydrogen abstraction (intra- or intermolecular)

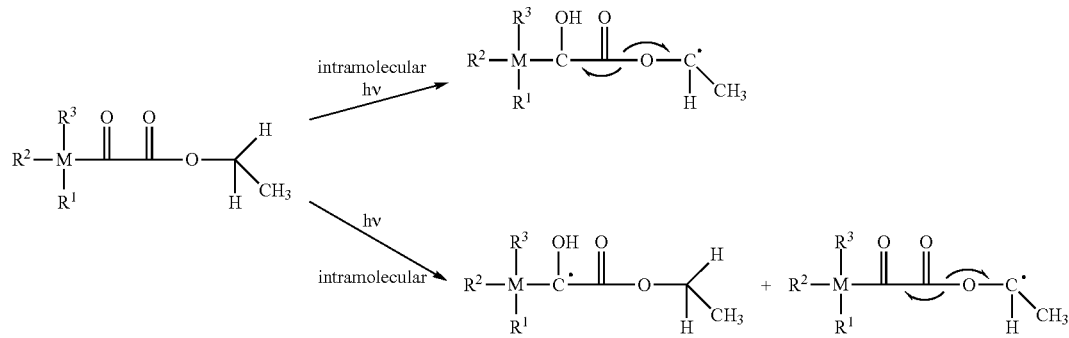

Both the cleavage of a glyoxylate group and the hydrogen abstraction mechanism is known for photoinitiators which do not contain silicium or germanium, such as ethyl phenylglyoxylate (Irgacure® MBF).

For compounds of formula (I) wherein R has the same meaning as X or is a group of formula (III), the present inventors carried out molecular modelling calculations from which it appears that a Si—C or Ge—C bond cleavage can be ruled out, since the C—C bond of the —C(=O)—C(=O)— moiety is weaker than the Si—C or Ge—C bond.

The compounds of formula (I) represent photoinitiators. Specifically, they may act as Norrish type I photoinitiators and thus may be used alone, or in combination with a coinitiator (b2).

The dental composition may further comprise a coinitiator (b2). The dental composition may comprise one or more coinitiator(s) (b2). The coinitiator may be selected from electron donors in the form of an amine compound and compounds having a Si—H or Ge—H bond, and photoinitiators other than compound of formula (I).

The coinitiator (b2) may be an electron donor. Preferred electron donors include, for example, amines, amides, ethers, thioethers, ureas, thioureas, ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. Particularly preferred donors contain an electron donor atom such as a nitrogen, oxygen, phosphorus, or sulfur atom, and an abstractable hydrogen atom bonded to a carbon or silicon atom alpha to the electron donor atom.

Particularly preferred amine compounds are tertiary amines selected from the group consisting of triethanolamine, 4-N,N-dimethylaminobenzonitrile, methyl N,N-dimethylaminobenzoate, ethyl N,N-dimethylaminobenzoate, N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene. In particular, the tertiary amine is selected from the group consisting of triethanolamine, methyl 4-N,N-dimethylaminobenzoate, ethyl 4-N,N-dimethylaminobenzoate, 4-N,N-dimethylaminoethyl methacrylate and isoamyl 4-N,N-dimethylaminobenzoate.

The coinitiator (b2) may be a compound having a Si—H or Ge—H bond. Preferably, compounds having a Si—H or Ge—H bond are trihydrocarbylsilanes or trihydrocarbylgermanes in which the three hydrocarbylgroups have the same meaning as defined for $R_1$, $R_2$ and $R_3$. More preferably, the compound having a Si—H or Ge—H bond is triphenylsilicium hydride ($Ph_3SiH$) or triphenylgermanium hydride ($Ph_3GeH$), most preferably triphenylgermanium hydride ($Ph_3GeH$).

The coinitiator (b2) may be a photoinitiator other than compound of formula (I). Such a photoinitiator may for example be added to improve the matching of the emission spectrum of dental LED with the absorption of the photoinitiating system. For example, if compound of formula (I) does not or not sufficiently absorb light within the range of 450 to 500 nm, it is preferred to add a photoinitiator having a good absorption within this range.

For the coinitiator (b2) in the form of a photoinitiator other than compound of formula (I), isopropylthioxanthone is excluded.

A coinitiator (b2) in the form of a photoinitiator other than compound of formula (I) may be in the form of a Norrish type I or type II photoinitiator.

The Norrish type I photoinitiator may be selected from the group consisting of a triazine derivate, 2,4-6-trimethylbenzoyl-diphenylphosphine oxide (Irgacure® TPO), 2,4-6-trimethylbenzoyl-diphenylphosphinate (Irgacure® TPO-L, TPO-L), bis(2,4-6-trimethylbenzoyl)-phenylphosphineoxide (Irgacure® BAPO-X). Preferably, the Norrish type I photoinitiator is a triazine derivative, preferably tris(trihaloalkyl)-triazine, more preferably tris(trihalomethyl)-triazine, even more preferably tris(trichloromethyl)-triazine and in particular 2,4,6-tris(trichloromethyl)-1,3,5-triazine.

Typical Norrish type II photoinitiators are e.g a 1,2-diketone or a 1,3 diketone. Examples of suitable 1,2-diketones are camphor quinone, benzil, 2,2'-3,3'- and 4,4'-dihydroxylbenzil, 2,3-butanedione, 2,3-pentanedione, 2,3-hexanedione, 3,4-hexanedione, 2,3-heptanedione, 3,4-heptanedione, 2,3-octanedione, 4,5-octanedionefuril, biacetyl, 1,2-cyclohexanedione, 1,2-naphthaquinone, and acenaphthaquinone. Examples of suitable 1,3-diketones are dibenzoyl methane, benzoyl acetone and acetyl propionyl methane.

Preferably, the coinitiator (b2) is a Norrish type II photoinitiator, more preferably a 1,2-diketone, most preferably camphor quinone.

It was surprisingly found that by means of adding a photoinitiator such as camphor quinone as a coinitiator (b2), the matching of the absorption of polymerization initiator system comprising (b1) the compound of formula (I) with the emission spectrum of an irradiation source can be improved compared to a conventional polymerization initiator system based on a conventional Norrish type I or II photoinitiator.

It is preferred that the coinitiator is an electron donor in the form of an amine compound or a compound having a Si—H or Ge—H bond, optionally in combination with a photoinitiator other than compound of formula (I).

The polymerization initiator system may further comprise one or more components selected from
(b3) an iodonium salt, a sulfonium salt and a phosphonium salt.

Preferably, the iodonium, sulfonium and phosphonium salts are selected from the following group:
(1) an iodonium compound of the following formula (VI):

$$R^{19}-I^+-R^{20}A^- \quad (VI)$$

wherein
$R^{19}$ and $R^{20}$
which are independent from each other, represent an organic moiety, and
$A^-$ is an anion;
(2) a sulfonium compound of the following formula (VII):

$$R^{21}R^{22}R^{23}S^+A^- \quad (VII)$$

wherein
$R^{21}$, $R^{22}$ and $R^{23}$
which are independent from each other, represent an organic moiety or wherein any two of $R^{21}$, $R^{22}$ and $R^{23}$ form a cyclic structure together with the sulfur atom to which they are bound, and
$A^-$ is an anion;
(3) a phosphonium compound of the following formula (VIII):

$$R^{24}R^{25}R^{26}P^+A^- \quad (VIII)$$

wherein
$R^{24}$, $R^{25}$ and $R^{26}$
which are independent from each other, represent an organic moiety, and
$A^-$ is an anion;

In the iodonium compounds of formula (VI), $R^{19}$ and $R^{20}$ preferably represent an aromatic, an aliphatic or an alicyclic group. An aromatic group may be a phenyl group. The phenyl group may be substituted by one or more straight chain or branched alkyl groups having 1 to 6 carbon atoms, straight chain or branched alkoxy groups having 1 to 6 carbon atoms, aromatic groups such as aryl groups or aryloxy groups, alicyclic groups having 3 to 6 carbon atoms, halogen atoms, hydroxyl groups, or amino groups. The aliphatic group may be a straight chain or branched alkyl groups having 1 to 6 carbon atoms which may be substituted by one or more aromatic groups, alicyclic groups having 3 to 6 carbon atoms, halogen atoms, hydroxyl groups or amino groups. An alicyclic group may be a group having 3 to 6 carbon atoms which may be substituted by one or more aromatic groups, aliphatic groups, halogen atoms, hydroxyl groups or amino groups.

According to a preferred embodiment, the iodonium compound of formula (VI) is a diaryl iodonium salt. Examples of useful diaryl iodonium salt include (4-methylphenyl)[4-(2-methylpropyl) phenyl]iodonium hexafluoroantimonate, include (4-methylphenyl)[4-(2-methylpropyl) phenyl]iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds of formula (VI) include diaryliodonium hexafluorophosphate such as diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl]iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl]iodonium tetrafluoroborate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis(pentafluorophenyl)borate.

According to a particularly preferred embodiment, the iodonium compounds of formula (VI) are selected from the group consisting of DPI hexafluorophosphate and 4-methylphenyl)[4-(2-methylpropyl)phenyl]iodonium hexafluorophosphate (Irgacure® 250, commercial product available from BASF SE).

According to a preferred embodiment, the polymerizable matrix contains the iodonium compound of the following formula (VI), preferably in the form of a diphenyl iodonium (DPI) or di(4-methylphenyl)iodonium (Me2-DPI) compound, more preferably di(4-methylphenyl)iodonium (Me2-DPI), in an amount from 0.001 to 2 percent by weight based on the total weight of the composition.

A preferred sulfonium compound of the formula (VII) is S-(phenyl)thianthrenium hexafluorophosphate of the following formula:

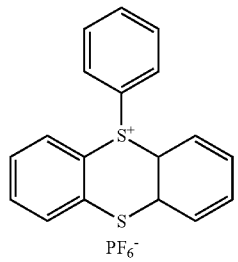

The phosphonium compound of formula (VII) may be a tetrakis-(hydroxymethyl)-phosphonium (THP) salt or a tetrakis-(hydroxymethyl)-phosphonium hydroxide (THPOH) salt, wherein the anion $A^-$ is selected from the group consisting of formate, acetate, phosphate, sulphate, fluoride, chloride, bromide and iodide.

In a salt of a compound of any one of formula (VI) to (VIII), the anion may be an anion selected from halogenides such as chloride, bromide and iodide, hexafluorophosphate, tetrafluoroborate, tetraphenylborate, hexafluoroantimonate and trifluoromethylsulfonate.

The use of (b1) a compound of formula (I) and (b2) an optional coinitiator together with (b3) an optional iodonium-, sulfonium or phosphonium salt may provide for a synergistic effect, in particular in the case of iodonium salts.

Preferably, the polymerisation initiator system (b) comprises a combination of components (b1), (b2) and (b3). More preferably, the polymerisation initiator system (b) comprises:
- (b1) a compound of formula (I),
- (b2) a coinitiator being an amine compound or a compound having a Si—H or Ge—H bond, and optionally additionally a coinitiator being an 1,2 diketone photoinitiator, and
- (b3) a iodonium salt, a sulfonium salt or a phosphonium salt.

According to a particularly preferred embodiment, polymerisation initiator system (b) comprises
- (b1) a compound of formula (I), preferably selected from the group consisting of benzoyldiphenylmethylsilane (BDMSi), benzoyltrimethylsilane (BTMSi) and tert-butyl (tert-butyldimethylsilyl)glyoxylate (DKSi),
- (b2) a coinitiator being ethyl N,N-dimethylaminobenzoate (EDB) or triphenylgermanium hydride ($Ph_3GeH$), and optionally additionally camphor quinone (CQ), and
- (b3) a diphenyliodonium (DPI) salt, preferably DPI hexafluorophosphate.

It was surprisingly found that owing to synergistic effects between components (b1), (b2) and (b3), a higher conversion rate of the compounds having a polymerizable double bond (a) and more advantageous kinetics in terms of the polymerization time can be obtained compared with a polymerization initiator system consisting of (b1). Furthermore, a polymerization initiator system comprising components (b1), (b2) and (b3) is particularly suitable for polymerizing relatively thin films of up to 0.1 mm, such as adhesive films, as well as for relative thick samples having a thickness of about 1 to 2 mm or more, such as fillings and prosthetics. Besides, a polymerization initiator system comprising components (b1), (b2) and (b3) provides for good bleaching, that is, colorless polymers are obtained. When camphor quinone (CQ) is used as additional coinitiator, for the polymerization initiator system comprising components (b1), (b2) and (b3), the aforementioned effects are significantly improved compared to a conventional polymerization initiator system consisting of camphor quinone (CQ) as polymerisation initiator in combination with components (b2) and (b3).

Preferably, the polymerization initiator system further comprises
- (b4) an aromatic tertiary phosphine compound of the following formula (IV):

$$Z—R^5 \quad \text{(IV)}$$

wherein
Z is a group of the following formula (V)

$$R^6(Ar)P— \quad \text{(V)}$$

wherein
R⁶ represents a substituted or unsubstituted hydrocarbyl group;
Ar represents a substituted or unsubstituted aryl or heteroaryl group;
R⁵ is a substituted or unsubstituted hydrocarbyl group or a group LZ', wherein
L is a substituted or unsubstituted divalent hydrocarbyl group which may contain a linkage selected from an ether linkage, a thioether linkage, an ester linkage, an amide linkage, and a urethane linkage and
Z' has the same meaning as Z, whereby Z and Z' may be the same or different;
wherein the group R⁶ and Ar may be substituted by one or more groups selected from a hydroxyl group, an oxo group, a —NR⁷R⁸ group (wherein R⁷ and R⁸, which may be the same or different, are selected from a hydrogen atom and $C_{1-6}$ alkyl groups), a carboxyl group, and a group having a polymerizable double bond, and
R⁵ and L may be substituted by one or more groups selected from a hydroxyl group, an oxo group, a —NR⁷R⁸ group (wherein R⁷ and R⁸, which may be the same or different, are selected from a hydrogen atom and $C_{1-6}$ alkyl groups), a carboxyl group, and a group having a polymerizable double bond.

In the aromatic tertiary phosphine compound of the formula (IV), moieties Z, R⁵, Ar, F⁶, L, Z, Z' may be defined as follows:

For R⁶, the monovalent hydrocarbyl group may be an alkyl group, a cycloalky group, a cycloalkylalkyl group, an arylalkyl group or an aryl group.

Ar represents a substituted or unsubstituted aryl or heteroaryl group. An aryl group may be selected from a phenyl group, a naphtyl group, a tolyl group, a xylyl group, and a styryl group. A heteroaryl group may be a pyridyl group.

L is a substituted or unsubstituted divalent hydrocarbyl group which may contain a linkage selected from an ether linkage, a thioether linkage, an ester linkage, an amide linkage, and a urethane linkage. For L, the divalent hydrocarbyl group may be an alkyldiyl group, a cycloalkyldiyl group, a cycloalkylalkyl-diyl group, an arylalkyl-diyl group or an aryldiyl group. In a cycloalkylalkyl-diyl, one valency may be bonded to each of the cycloalkyl moiety or the alkyl moiety, or both valencies may be bonded to either the cycloalkyl moiety or the alkyl moiety. In a arylalkyl-diyl group, each of the aryl moiety or the alkyl moiety may be monovalent respectively, or either the aryl moiety or the alkyl moiety is divalent, while the other moiety is nonvalent. In a cycloalkylalkyl-diyl, each of the cycloalkyl moiety or the alkyl moiety may be monovalent respectively, or either the cycloalkyl moiety or the alkyl moiety is divalent, while the other moiety is nonvalent.

The following definitions apply both for the monovalent and the divalent hydrocarbyl group, therefore, for the definition of the divalent hydrocarbyl group, the suffixes "diyl" and "-diyl" are bracketed.

An alkyl(diyl) group may be straight-chain or branched $C_{1-20}$ alkyl(diyl) group, typically a $C_{1-8}$ alkyl(diyl) group. Examples for a $C_{1-6}$ alkyl(diyl) group can include linear or branched alkyl(diyl) groups having 1 to 6 carbon atoms, preferably 1 to 4 carbon atoms, for example, methyl(diyl), ethyl(diyl), n-propyl(diyl), isopropyl(diyl), n-butyl(diyl), isobutyl(diyl), sec-butyl(diyl), tert-butyl(diyl), n-pentyl(diyl), isopentyl(diyl) and n-hexyl(diyl).

A cycloalkyl(diyl) group may be a $C_{3-20}$ cycloalkyl(diyl) group. Examples of the cycloalkyl(diyl) group can include those having 3 to 14 carbon atoms, for example, cyclopropyl(diyl), cyclobutyl(diyl), cyclopentyl(diyl) and cyclohexyl(diyl). A cycloalkylalkyl(diyl) group can include those having 4 to 20 carbon atoms.

A cycloalkylalkyl(-diyl) group can include a combination of a linear or branched alkyl(diyl) group having 1 to 6 carbon atoms and a cycloalkyl(diyl) group having 3 to 14 carbon atoms. Examples of the cycloalkylalkyl(-diyl) group can for example, include methylcyclopropyl(-diyl) methylcyclobutyl(-diyl), methylcyclopentyl(-diyl), methylcyclohexyl(-diyl), ethylcyclopropyl(-diyl), ethylcyclobutyl(-diyl), ethylcyclopentyl(-diyl), ethylcyclohexyl(-diyl), propylcyclopropyl(-diyl), propylcyclobutyl(-diyl), propylcyclopentyl(-diyl), propylcyclohexyl(-diyl).

An arylalkyl(-diyl) group may be a $C_{7-20}$ arylalkyl(-diyl) group, typically a combination of a linear or branched alkyl(diyl) group having 1 to 6 carbon atoms and an aryl(-diyl) group having 6 to 10 carbon atoms. Specific examples of an arylalkyl(-diyl) group are a benzyl(-diyl) group or a phenylethyl(-diyl) group.

An aryl(diyl) group can include aryl(diyl) groups having 6 to 10 carbon atoms. Examples of the aryl(diyl) group are phenyl(diyl) and naphtyl(diyl). Aryl(diyl) groups may contain 1 to 3 substituents. Examples of such substituents can include halogen atoms, a cyano group, a hydroxy group, an amino group, $C_{1-6}$ alkyl groups and $C_{1-6}$ alkoxy groups. Here, illustrative of the halogen atoms can be fluorine, chlorine, bromine and iodine. The $C_{1-4}$ alkyl(diyl) groups are, for example, methyl(diyl), ethyl(diyl), n-propyl(diyl), isopropyl(diyl) and n-butyl(diyl). Illustrative of the $C_{1-4}$ alkoxy(diyl) groups are, for example, methoxy(diyl), ethoxy(diyl) and propoxy(diyl). The alkyl(diyl) moieties in these substituents may be linear, branched or cyclic.

Preferably, the hydrocarbyl group is an aryl(diyl) group selected from a phenyl(diyl) group and a naphthyl(diyl) group, which groups may optionally be substituted by one to three groups selected from halogen atoms, a cyano group, an amino group, a hydroxy group, $C_{1-6}$ alkyl groups and C1-6 alkoxy groups, or wherein the hydrocarbyl group is a non-aromatic hydrocarbyl group selected from a straight chain or branched alkyl group, a straight chain or branched alkenyl group, or a straight chain or branched alkynyl group.

The $C_{1-8}$ alkyl(diyl) group and the $C_{3-14}$ cycloalkyl(diyl) group may optionally be substituted by one or more members of the group selected from a $C_{1-4}$ alkyl group, $C_{1-4}$ alkoxy group, a phenyl group, and a hydroxy group. Examples for a $C_{1-4}$ alkyl group can include linear or branched alkyl groups having 1 to 4 carbon atoms, for example, methyl, ethyl, n-propyl, isopropyl, n-butyl, isobutyl, sec-butyl, tert-butyl. Examples for an $C_{1-4}$ alkoxy group can include linear or branched alkoxy groups having 1 to 4 carbon atoms, for example, methoxy, ethoxy, n-propoxy, isopropoxy, n-butoxy, isobutoxy, sec-butoxy, and tert-butoxy.

Moreover, in formula (IV), any of the hydrocarbyl group may be substituted by on or more groups selected from halogen atoms, a cyano group, an amino group or a hydroxy group. Accordingly, in the hydrocarbyl groups some or all hydrogen atoms are replaced by halogen atoms (e.g., fluoro, bromo, chloro), for example, halo-substituted alkyl groups such as chloromethyl, chloropropyl, bromoethyl and trifluoropropyl, and cyanoethyl.

In case the hydrocarbyl group contains an alkyl(diyl) chain, one or more carbon atoms in the alkyl(diyl) chain may be replaced by an oxygen atom, a sulfur atom, an amide group, an ester group, or a urethane group. In case the hydrocarbyl group is an alkyl group having more than one carbon atom, the alkyl group contains an alkylene. Accordingly, in case the hydrocarbyl group is an n-hexyl group, any of the carbon atoms of the alkylene chain excluding the terminal methyl group may be replaced by an oxygen atom, a sulfur atom, an amide group, an ester group, a urethane group or an NH group. Therefore, the following groups may be given as specific examples in case of one or more oxygen atoms:

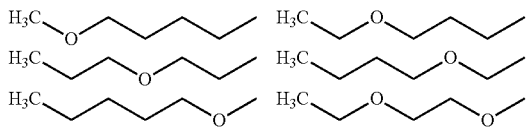

In formula (IV), group $R^6$ and/or Ar as well as $R^5$ and/or may be substituted with a polymerizable double bond, preferably a carbon-carbon double bond. Examples of polymerizable carbon-carbon double bonds include vinyl, conjugated vinyl, allyl, acryl, methacryl and styryl. Preferably, the polymerizable double bond is selected from the group consisting of methacryl, acryl and styryl. More preferably, the double bond is styryl.

Preferably, $R^6$ and Ar independently are aromatic hydrocarbyl groups selected from a phenyl group, a naphtyl group, a tolyl group, a xylyl group, and a styryl group.

As regards $R^5$, this moiety is preferably an aryl group, which may be substituted by one or more groups selected from a hydroxyl group, an amino group, a —$NR^7R^8$ group (wherein $R^7$ and $R^8$, which may be the same or different, are selected from $C_{1-6}$ alkyl groups), a carboxyl group, and a group having a polymerizable double bond. Alternatively, $R^5$ is preferably a group LZ' wherein Z' and Z are the same.

More preferably, $R^5$ is a $C_{1-6}$ alkyl group or a $C_{1-6}$ alkenyl group, which groups may be substituted by one or more groups selected from a hydroxyl group, an amino group, a —$NR^7R^8$ group (wherein $R^7$ and $R^8$, which may be the same or different, are selected from $C_{1-6}$ alkyl groups), a carboxyl group, and a group having a polymerizable double bond. The group having a polymerizable double bond may be vinyl group, an allyl group, a (meth)acryloyloxy group or a (meth)acryloylamido group.

Even more preferably, the aromatic phosphine compound is a compound of formula (IV) wherein Z is a group of the following formula (V'):

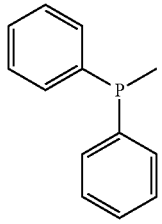

Specific examples for a compound of formula (IV) include triphenyl phosphine (TPP), 4-(diphenylphosphino)styrene (DPPS), 4-(diphenylphosphino)benzoic acid, 4-(diphenylphosphino) benzoic acid, 3-(diphenylphophonino) propionic acid, (4-(diphenylphosphino) N,N'-dimethylaniline, 2,2'-bis(diphenylphosphino)benzophenone (BDPPEP), bis[2-(diphenylphosphino)phenyl]ether (BD-PPE), (4-Hydroxyphenyl)diphenylphosphine, allyldiphenylphosphine. Preferably, the compound of formula (I) is triphenyl phosphine (TPP) or 4-(diphenylphosphino)styrene (DPPS), more preferably 4-(diphenylphosphino)styrene (DPPS).

It was surprisingly found that aromatic tertiary phosphine compounds of formula (IV) may provide for both an advantageous efficiency in terms of a higher polymerisation rate and a higher final conversion rate compared to a dental composition comprising a polymerization initiator system without an aromatic tertiary phosphine compound of formula (IV). Advantageously, the polymeriation rate may be adjusted within a range which still provides for corrections when applying the dental composition to a patient's tooth or when forming a prosthesis. Although photopolymerization is achieved at a higher polymerisation and conversion rate, owing to the present polymerization initiator system, undesired side reaction resulting e.g. in discoloration of the cured dental composition can be effectively suppressed. Besides, by adding an aromatic tertiary phosphine compound of formula (IV) to the present polymerization initiator system, a yellow coloration of the dental composition eventually formed already before light curing can efficiently be reduced/decreased. That is, there is a photo-bleaching effect which provides for an advantageous effective reduction/decrease of yellow discolorations of the dental composition, while the initiator system furthermore provides for an advantageous polymerization and conversation rate throughout the whole course of time of the photopolymerization.

The present polymerisation initiator system is not only advantageous for relatively thin films of up to 0.1 mm such as adhesive films, but also particularly suitable for polymerizing relative thick samples of a dental composition having a thickness of about 1 to 2 mm or more, such as fillings and prosthetics.

Without wishing to be bound to theory, it is believed that a synergistic effect due to the combination of (b1) the compound of formula (I) and (b2) the coinitiator together with (b3) the aromatic tertiary phosphine of formula (IV) is provided according to the present invention.

A further positive effect associated with the application of tertiary phosphines of formula (IV) is that owing to the tertiary phosphines of formula (IV), the present compositions may exhibit an advantageous storage stability, that is the compositions keep the above characteristics of an advantageous efficiency in terms of a higher polymerisation rate and a higher final conversion rate even after a long storage time, e.g. about 2 month.

From the above listed aromatic tertiary compounds of formula (IV), 4-(diphenylphosphino)styrene (DPPS) is particularly preferred, since this compound provides for particularly improved photo-bleaching results compared to the already advantageous results obtained with triphenyl phosphine (TPP). Besides, DPPS is particularly suitable for initiating polymerization of thick samples of about 1 to 2 mm thickness. Besides, DPPS not only provides for an improved conversion rate, but with DPPS, the conversion rate of the dental composition can be maintained even after a storage time of 2 weeks or more.

Preferably, in the present dental composition, the polymerization initiator system comprises component (b1), (b2), (b3) and (b4) in a molar ratio ((b1):(b2):(b3):(b4)) of 1:(0.0 to 3.0):(0.0 to 3.0):(0.0 to 3.0), more preferably 1:(0.1 to 2.0):(0.1 to 2.0):(0.1 to 2.0), even more preferably 1:(0.2 to 1.0):(0.2 to 1.0):(0.2 to 1.0). It is preferred that in the aforementioned molar ratio, the amount of the aromatic tertiary phosphine (b4) is 0.1 or higher. Because, when the amount of the aromatic tertiary phosphine (b4) is less than 0.1, then the conversion rate of the compounds having a polymerizable double bond, and the reaction rate of the polymerization reaction (in the following termed "polymerization rate") may be low. By means of the addition of the optional coinitiator (b2) and/or the optional (b3) iodonium salt, sulfonium salt or phosphonium salt, both conversion rate and polymerization rate can be further advantageously adjusted.

Optionally, the dental compositions of the present invention may further comprise a stabilizer, a solvent and/or a particulate filler.

The dental composition may comprise one or more stabilizer(s).

The term "stabilizer" as used herein means any compound capable of preventing polymerizable compounds contained in the dental composition from spontaneous polymerization during storage. However, the stabilizer does not disturb or prevent intended polymerisation curing of the dental composition during application.

For example, the stabilizer may be a conventional stabilizer selected from the group consisting of hydroquinone, hydroquinone monomethylether, tert-butyl-hydroquinone, tert-butylhydroxyanisol, propyl gallate and 2,6-di-tert-butyl-p-cresol. From these conventional stabilizers, 2,6-di-tert-butyl-p-cresol is preferred.

Preferably, the stabilizer is a compound of the following formula (IX) and/or (X):

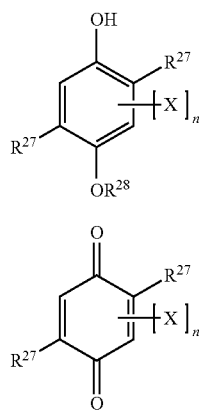

wherein
the $R^{27}$, which may be the same or different, independently represent a branched $C_{3-8}$ alkyl group or alkenyl or a $C_{3-8}$ cycloalkyl or cycloalkenyl group,
$R^{28}$ represents a hydrogen atom, $C_{1-6}$ alkyl or $C_{2-6}$ alkenyl group, or a $C_{1-6}$ fluoroalkyl or $C_{2-6}$ fluoroalkenyl group,
X represents a group selected from a $C_{1-8}$ alkyl group or a $C_{3-8}$ cycloalkyl group, and
n is 0, 1 or 2.

It was surprisingly found that the class of stabilizers of formula (IX) and/or (X) provides for full or at least substantial avoidance of discoloration upon storage and/or during photocuring. In particular, this class of stabilizers provides for a surprising stabilizing effect in an acidic aqueous mixture so that a dental composition having a pH of less than 7 may be provided which has no or substantially no discoloration upon storage and an excellent storage stability due to an improved resistance against premature polymerization.

More preferably, the stabilizer is a compound of formula (IX) and/or (X) wherein the $R^{27}$, which may be the same or different, independently represent a branched $C_{3-8}$ alkyl group or a $C_{3-8}$ cycloalky group, and $R^{28}$ represents a hydrogen atom, $C_{1-6}$ alkyl group or a $C_{1-6}$ fluoroalkyl group, and n is 0 or 1. Even more preferably, the stabilizer is a compound of formula (IX) and/or (X) wherein the $R^{27}$, which may be the same or different, independently represent a branched $C_{3-8}$ alkyl group and $R^{28}$ represents a hydrogen atom or a $C_{1-6}$ alkyl group, and n is 0. Most preferably, the stabilizer is a compound of the following formulae (IXa), (IXb) or (Xa):

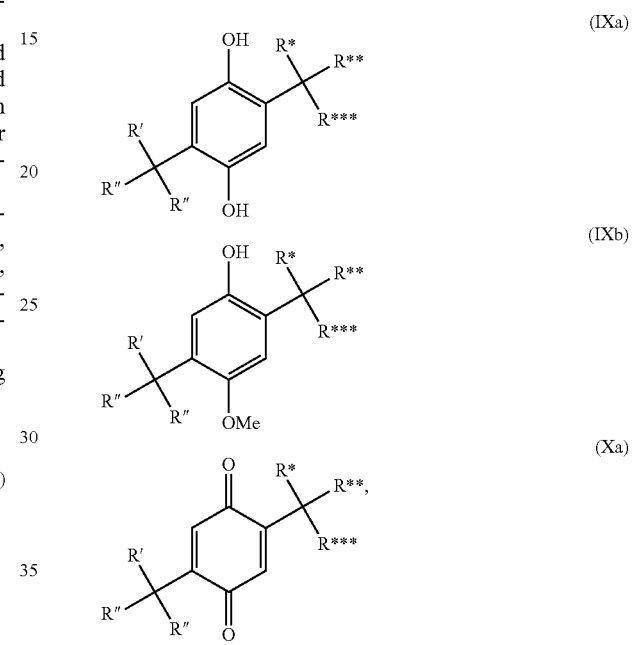

wherein R', R", R"', R*, R and R*, which may be the same or different, independently represent a methyl or an ethyl group. It is particularly preferred that the stabilizer of formulae (IXa), (IXb) or (Xa) is a compound of the following formulae:

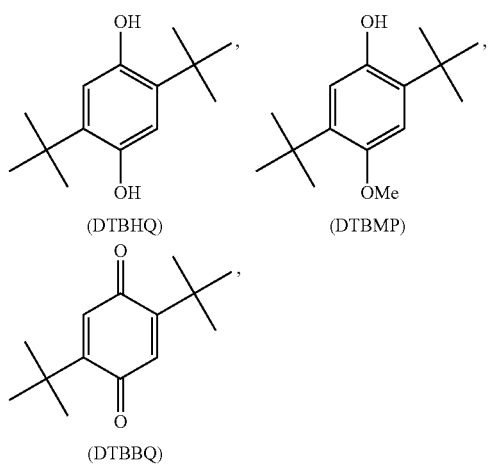

preferably DTBHQ.

The stabilizer DTBHQ is particularly preferred, since from experimental testings it appears that this stabilizer provides the best results in view of the discoloration problematic, i.e. there is no or almost no discoloration of the dental composition upon storage at 50° C. for 30 days.

Discoloration upon storage and/or during photocuring may be determined according to ISO 7491:2000(en).

The dental composition according to the invention contains the stabilizer in an amount of 0.001 to 1 percent by weight, preferably 0.005 to 0.8 percent by weight based on the total weight of the composition. When the amount of the stabilizer is below the above indicated lower limit of 0.001, then storage stability of the dental composition might be insufficient, since the amount of stabilizer is too small to provide a stabilizing effect. However, when the amount of stabilizer is above the maximum threshold of 1 percent by weight, then the applicability of the dental composition might be negatively affected, since higher amounts of stabilizer may disturb or even substantially prevent intended polymerisation curing of the dental composition during application.

Suitable solvents may be selected from water, alcohols such as methanol, ethanol, propanol (n-, i-), butanol (n-, iso-, tert.-), ketones such as acetone or the like.

The dental composition of the present invention may preferably comprise 5 to 75 percent by weight based on the total weight of the composition of a solvent.

Suitable particulate fillers may be selected from fillers currently used in dental compositions.

The filler should be finely divided and preferably has a maximum particle diameter less than about 100 μm and an average particle diameter less than about 10 μm. The filler may have a unimodal or polymodal (e.g., bimodal) particle size distribution.

The filler can be an inorganic material. It can also be a crosslinked organic material that is insoluble in the polymerizable resin, and is optionally filled with inorganic filler. The filler can be radioopaque. Examples of suitable particulate inorganic fillers are naturally-occurring or synthetic materials such as quartz, nitrides such as silicon nitride, glasses derived from, for example Ce, Sb, Sn, Zr, Sr, Ba and Al, colloidal silica, feldspar, borosilicate glass, kaolin, talc, titania, and zinc glass, and submicron silica particles such as pyrogenic silicas. Examples of suitable non-reactive organic filler particles include filled or unfilled pulverized polycarbonates or polyepoxides. Preferably the surface of the filler particles is treated with a coupling agent in order to enhance the bond between the filler and the matrix. The use of suitable coupling agents include gamma-methacryloxypropyltrimethoxysilane, gamma-mercaptopropyltriethoxysilane, gamma-aminopropyltrimethoxysilane, and the like.

The particulate filler may also be a filler obtainable by a process for the preparation of composite filler particles, comprising:

(a) coating a particulate filler having a median particle size (D50) of from 1 to 1200 nm with a coating composition containing a film-forming agent forming a coating layer on the surface of the particulate filler, said coating layer displaying reactive groups on the surface of the coating layer, said reactive groups being selected from addition polymerizable groups and step-growth polymerizable groups, thereby forming a coated particulate filler; subsequently or concurrently (b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

(c) optionally milling, classifying and/or sieving the granulation of the coated particulate filler; and (d) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP-A 2 604 247.

The dental composition of the present invention may preferably comprise 0.1 to 85 percent by weight based on the total weight of the composition of particulate filler.

The dental compositions of the present invention may further containpreservatives, pigments, free radical scavengers, reactive and nonreactive diluents, coupling agents to enhance reactivity of fillers, rheology modifiers, and surfactants.

Suitable preservatives may be selected from reducing agents such as vitamin C, inorganic sulfides and polysulfides and the like.

According to a particularly preferred embodiment, the dental composition according to the invention comprises (a) one or more compounds having at least one polymerizable double bond, preferably at least one of compounds of formulae (A), (B), (C), (D), (E) and (F), more preferably at least one of the group consisting of bis-GMA, TGDMA, UDMA, PENTA, BAABE and BADEP;

(b) a polymerization initiator system comprising (b1) a compound of the following formula (I'):

X'—R'  (I')

wherein
X' is a group of the following formula (II'):

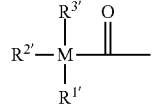

wherein
M is Si or Ge, preferably Si;
$R^{1'}$ and $R^{2'}$ are independently selected from the group consisting of a straight chain or branched $C_{1-4}$ alkyl group, and a phenyl or benzoyl group optionally substituted with one substituent selected from the group consisting of a halogen atom, a nitro group, a $C_{1-4}$ alkoxy group and a —$NR^xR^y$ group wherein $R^x$ and $R^y$ independently from each other represent a $C_{1-4}$ alkyl group, and
$R^{3'}$ is a straight chain or branched $C_{1-4}$ alkyl group, or a phenyl group optionally substituted with one substituent selected from the group consisting of a halogen atom, a nitro group, a $C_{1-4}$ alkoxy group and a —$NR^xR^y$ group wherein $R^x$ and $R^y$ independently from each other represent a $C_{1-4}$ alkyl group, R' (i) has the same meaning as X', whereby the compound of formula (I') may be symmetrical or unsymmetrical; or (ii) a group of the following formula (III'):

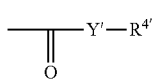

(III')

wherein
Y' represents a single bond, an oxygen atom or a group NR", wherein R" has the same meaning as R¹' and is selected independently therefrom;
R⁴' has the same meaning as R³' and is selected independently therefrom, or represents a trihydrocarbylsilyl group, a mono(hydrocarbylcarbonyl)dihydrocarbylsilyl group or a bi(hydrocarbylcarbonyl)monohydrocarbylsilyl) group, wherein the hydrocarbyl and hydrocarbylcarbonyl groups have the same meaning as R¹', R²' and R³' and is selected independently therefrom, or
(iii) when M is Si, R may be a substituted or unsubstituted hydrocarbyl group having the same meaning as defined for R³' and being selected independently therefrom;
preferably the compound of formula (I) is selected from the group consisting of benzoyldiphenylmethylsilane (BDMSi), benzoyltrimethylsilane (BTMSi), 4-chlorophenyl(trimethylsilyl)methanone, 3-chlorophenyl(trimethylsilyl)-methanone, 4-nitrophenyl (trimethylsilyl)methanone, 3-nitrophenyl-(trimethylsilyl)methanone, tert-butyl (tert-butyldimethylsilyl) glyoxylate) (DKSi), N,N-dimethylamino (tert-butyldimethylsilyl)glyoxamide and N,N-dimethylamino (tert-butyldimethylgermanyl)glyoxamide, tert-butyl (trimethylgermanyl)glyoxylate (TKGe); most preferably from the group consisting of benzoyldiphenylmethylsilane (BDMSi), benzoyltrimethylsilane (BTMSi), tert-butyl (tert-butyldimethylsilyl)-glyoxylate) (DKSi) and tert-butyl (trimethylgermanyl)glyoxylate (TKGe);
(b2) optionally at least one coinitiator selected from the group consisting of an amine compound or a compound having a Si—H or Ge—H bond, and optionally a photoinitiator other than compound of formula (I),
preferably the coinitiator is selected from the group consisting of triethanolamine, 4-N,N-dimethylaminobenzonitrile, methyl N,N-dimethylaminobenzoate, ethyl N,N-dimethylaminobenzoate (EDB), N,N-dimethylaminoethyl methacrylate and isoamyl 4-N,N-dimethylaminobenzoate, N,N-dimethylaniline, N,N-dimethyltoluidine, N,N-diethanoltoluidine, dimethylaminoanisole, 1 or 2-dimethylaminonaphthalene, triphenylgermanium hydride, and camphor quinone (CQ); more preferably the coinitiator is at least one selected from the group consisting of EDB, Ph₃GeH, CQ and 2,4,6-tris(trichloromethyl)-1,3,5-triazine; most preferably, the coinitiator is EDB or Ph₃GeH, optionally in combination with CQ;
(b3) optionally a compound selected from the group consisting of (4-methylphenyl)[4-(2-methylpropyl) phenyl]iodonium hexafluoroantimonate, include (4-methylphenyl)[4-(2-methylpropyl) phenyl]iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl) iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, DPI hexafluorophosphate, S-(phenyl)thianthrenium hexafluorophosphate, tetrakis-(hydroxymethyl)-phosphonium (THP) salt and tetrakis-(hydroxymethyl)-phosphonium hydroxide (THPOH) salt; preferably, a diphenyliodonium (DPI) salt, most preferably DPI hexafluorophosphate;
(b4) optionally at least one aromatic tertiary phosphine selected from the group consisting of triphenyl phosphine (TPP), 4-(diphenylphosphino)styrene (DPPS), 4-(diphenylphosphino)benzoic acid, 4-(diphenylphosphino) benzoic acid, 3-(diphenylphophonino)propionic acid, (4-(diphenylphosphino) N,N'-dimethylaniline, 2,2'-bis(diphenylphosphino)benzophenone (BDPPEP), bis[2-(diphenylphosphino)phenyl]ether (BDPPE), (4-hydroxyphenyl)diphenylphosphine and allyldiphenylphosphine; preferably, the compound of formula (IV) is triphenyl phosphine (TPP) or 4-(diphenylphosphino)styrene (DPPS), most preferably 4-(diphenylphosphino)styrene (DPPS),
wherein the polymerization initiator system comprises component (b1), (b2), (b3) and (b4) in a molar ratio ((b1): (b2):(b3):(b4)) of 1:(0.0 to 3.0):(0.0 to 3.0):(0.0 to 3.0), preferably of 1:(0.1 to 2.0):(0.1 to 2.0):(0.1 to 2.0).

In the above particularly preferred embodiment, the polymerization initiator system (b) preferably comprises components (b2) or (b3), more preferably (b2) and (b3).

The compound of formula (I) according to the present invention may be used for the preparation of a dental composition, preferably of a dental composition according to the invention as described above.

The invention will now be further illustrated by the following Examples.

EXAMPLES

Example 1: Preparation of Acylsilanes

General procedure for the preparation of acylsilanes.[1] A 10 mL screw-capped glass tube with a magnetic stir bar was charged with 0.054 g dichloro(Θ³-allyl)dipalladium(II) (0.3 mmol), 0.1 g Triethylphosphit (0.6 mmol) under N₂. Hexametyldisilane (0.96 g, 6.6 mmol) was added, and the mixture was stirred for 5 min at room temperature. After that, 6 mmol benzoylchloride was added slowly to the yellow solution. The reaction mixture was heated at 110° C. for 2.5 h. After cooling to room temperature, the reaction mixture was purified by column chromatography using the indicated eluent, without any preceding purification step.

[1] Yamamoto, K.; Suzuki, S.; Tsuji, J. Tetrahedron Lett. 1980, 21, 1653.

Example 1a: Phenyl(Trimethylsilyl)Methanone

The title compound was prepared according to the general procedure using 0.84 g benzoylchloride (6 mmol), 0.054 g dichloro(η³-allyl)dipalladium(II) (0.3 mmol), 0.1 g Triethylphosphit (0.6 mmol) and 0.96 g hexametyldisilane (6.6 mmol). The crude product was purified by column chromatography and received as clear yellow oil.

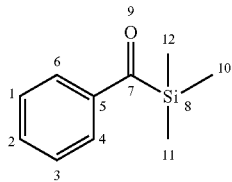

¹H-NMR [ppm]: (300 MHz, CDCl₃) δ 7.85-7.82 (m, 2H, Pos. 4, 6), δ 7.57-7.44 (m, 4H, Pos. 1, 2, 3), δ 0.38 (s, 9H, Pos. 10, 11, 12)

¹³C-NMR [ppm]: (75 MHz, CDCl₃) δ 235.94 (Pos. 7); δ 141.48 (Pos. 5); δ 132.84 (Pos. 2); δ 128.80 (Pos. 4, 6); δ 127.63 (Pos. 1, 3); δ -1.21 (Pos. 10, 11, 12)

5.000 g (9.7656 mmol) 2,2-bis[4-[2-hydroxy-3-methacryloyloxypropoxy)phenyl]propane (Bis-GMA), 1.1983 g (4.1853 mmol) triethylene glycol dimethacrylate (TGDMA), 0.0497 g (0.2790 mmol) Benzoyl trimethylsilan (BTMS), 0.0999 g (0.6696) dimethylaniline and 0.0047 g (0.0212 mmol) 2,6-di-tert-butyl-p-cresol were mixed homogeneously. The polymerization enthalpy of this mixture is $\Delta_R H = -56.5$ kJ/mol, measured with the DSC 7 (Perkin-Elmer).

Example 1b:
4-Chlorophenyl(Trimethylsilyl)Methanone

The title compound was prepared according to the general procedure using 1.05 g 4-Chlorobenzoyl chloride (6 mmol), 0.054 g dichloro(η³-allyl)dipalladium(II) (0.3 mmol), 0.1 g Triethylphosphit (0.6 mmol) and 0.96 g Hexametyldisilan (6.6 mmol). The crude product was purified by column chromatography with ethyl acetate/n-Hexane (10:1) to afford 0.215 g (17%) of the acylsilane as clear yellow oil.

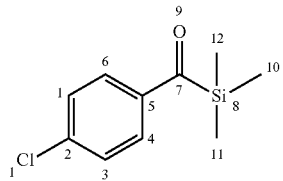

Element. anal.: theor. (C: 56.46%, H: 6.16%) pract. (C: 57.71%, H: 5.82%)

¹H-NMR [ppm]: (300 MHz, CDCl₃) δ 7.78-7.75 (m, 2H, Pos. 4, 6), δ 7.46-7.44 (m, 2H, Pos. 1, 3), δ 0.37 (s, 9H, Pos. 10, 11, 12)

¹³C-NMR [ppm]: (75 MHz, CDCl₃) δ 234.44 (Pos. 7); δ 139.65 (Pos. 2); δ 139.19 (Pos. 5); δ 129.15 (Pos. 4, 6); δ 129.97 (Pos. 1, 3); δ -1.28 (Pos. 10, 11, 12)

GC/MS: 212 [M⁺]

Example 1c:
3-Chlorophenyl(Trimethylsilyl)Methanone

The title compound was prepared according to the general procedure using 1.05 g 3-Chlorobenzoyl chloride (3 mmol), 0.027 g dichloro(η³-allyl)dipalladium(II) (0.15 mmol), 0.05 g Triethylphosphit (0.3 mmol) and 0.48 g Hexametyldisilan (3.3 mmol). The crude product was purified by column chromatography with ethyl acetate/n-Hexane (10:1) to afford 0.220 (17%) of the acylsilane as clear yellow oil.

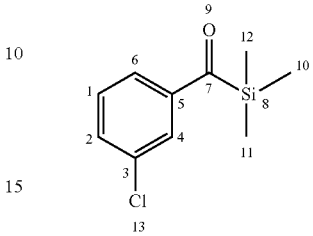

Element. anal.: theor. (C: 56.46%, H: 6.16%) pract. (C: 57.83%, H: 6.43%)

¹H-NMR [ppm]: (300 MHz, CDCl₃) δ 7.76-7.75 (m, 1H, Pos. 4), δ 7.73-7.69 (m, 1H, Pos. 2/6), δ 7.52-7.48 (m, 1H, Pos. 2/6); δ 7.44-7.39 (m, 1H, Pos. 1); δ 0.38 (s, 9H, Pos. 10, 11, 12)

¹³C-NMR [ppm]: (75 MHz, CDCl₃) δ 234.30 (Pos. 7); δ 142.63 (Pos. 2); δ 144.82 (Pos. 5); δ 128.27 (Pos. 4, 6); δ 124.27 (Pos. 1, 3); δ -1.17 (Pos. 10, 11, 12)

GC/MS: 212 [M⁺]

Example 1d:
4-Nitrophenyl(Trimethylsilyl)Methanone

The title compound was prepared according to the general procedure using 0.56 g 4-Nitrobenzoyl chloride (3 mmol), 0.027 g dichloro(Θ³-allyl)dipalladium(II) (0.15 mmol), 0.05 g Triethylphosphit (0.3 mmol) and 0.48 g Hexametyldisilan (3.3 mmol). The crude product was purified by column chromatography with ethyl acetate/n-Hexane (10:1) to afford 0.13 g (19.5%) of the acylsilane as clear yellow oil.

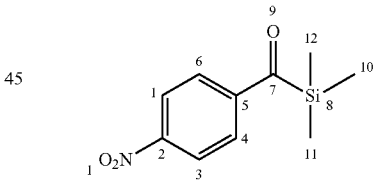

Element. anal.: theor. (C: 53.79%, H: 5.87%, N: 6.27) pract. (C: 52.84%, H: 5.75%, N: 6.29)

¹H-NMR [ppm]: (300 MHz, CDCl₃) δ 8.35-8.32 (m, 2H, Pos. 1, 3), δ 7.95-7.92 (m, 2H, Pos. 1, 3), δ 0.40 (s, 9H, Pos. 10, 11, 12)

¹³C-NMR [ppm]: (75 MHz, CDCl₃) δ 235.38 (Pos. 7); δ 149.98 (Pos. 2); δ 144.82 (Pos. 5); δ 128.27 (Pos. 4, 6); δ 124.27 (Pos. 1, 3); δ -1.17 (Pos. 10, 11, 12)

GC/MS: 223 [M⁺]

Example 1e:
3-Nitrophenyl(Trimethylsilyl)Methanone

The title compound was prepared according to the general procedure using 0.56 g 4-Nitrobenzoyl chloride (3 mmol), 0.027 g dichloro(Θ³-allyl)dipalladium(II) (0.15 mmol), 0.05 g Triethylphosphit (0.3 mmol) and 0.48 g Hexametyldisilan (3.3 mmol). The crude product was purified by column chromatography with ethyl acetate/n-Hexane (10:1) to afford 0.3 g (22%) of the acylsilane as a yellow solid.

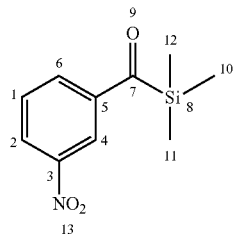

Element. anal.: theor. (C: 53.79%, H: 5.87%, N: 6.27) pract. (C: 52.73%, H: 5.77%, N: 6.31)

$^1$H-NMR [ppm]: (300 MHz, CDCl$_3$) δ 8.87-8.85 (m, 1H, Pos. 2), δ 8.41-8.37 (m, 1H, Pos. 4), δ 8.14-8.12 (m, 1H, Pos. 6); δ 7.71-7.66 (m, 1H, Pos. 1); δ 0.42 (s, 9H, Pos. 10, 11, 12)

$^{13}$C-NMR [ppm]: (75 MHz, CDCl$_3$) δ 233.83 (Pos. 7); δ 148.72 (Pos. 3); δ 142.11 (Pos. 5); δ 132.70 (Pos. 6); δ 130.10 (Pos. 1); δ 126.97 (Pos. 2), δ 122.60 (Pos. 4), δ −1.44 (Pos. 10, 11, 12)

GC/MS: 223 [M$^+$]

Example 2: Preparation of Germanyiglyoxylates

General procedure for the preparation of germanylglyoxylates: Germanylglyoxylates can be synthesized according to the general procedure depicted in Scheme 3.

Specifically, according to this general procedure, tert-butyl (trimethylgermanyl)glyoxylate (TKGe) having the structural formula

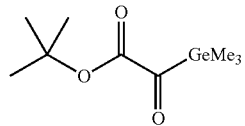

was synthesized.

FTIR spectrum (BaF$_2$ pellet) within wavelength range v=1600 to 1780 nm (cf. FIG. 20): glyoxylate peak at 1720 cm$^{-1}$.

Remarkably, this compound exhibits a good light absorption property in the 400-500 nm range with an extinction coefficient of about 120 M$^{-1}$cm$^{-1}$ at 470 nm.

Examples 3 to 5: Photopolymerisation Testing with Different Photoinitiator Systems Materials Camphor quinone (CQ) was obtained from Aldrich and used as representative Norrish type II system (Scheme 7).

Ethyldimethylaminobenzoate (EDB) and triphenylgermanium hydride (Ph$_3$GeH) used as coinitiators were obtained from Aldrich. Benzoyltrimethylsilane (BTMSi) and benzoyldiphenylmethylsilane (BDMSi) (Scheme 7) were used as Type I photoinitiators.

Diphenyliodonium hexafluorophosphate (DPI) was obtained from Aldrich. Bisphenol A-glycidyl methacrylate (Bis-GMA) and triethyleneglycol dimethacrylate (TEGDMA) were obtained from Sigma-Aldrich and used with the highest purity available (Scheme 7). A blend Bis-GMA/TEGDMA (70%/30% w/w) was used as benchmark matrix for dental material photopolymerizations.

compounds of formula (I) (b1)

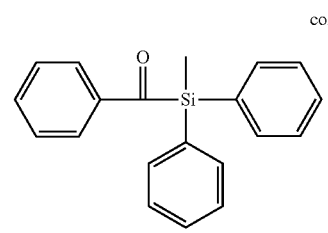

BDMSi

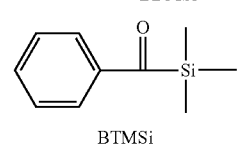

BTMSi

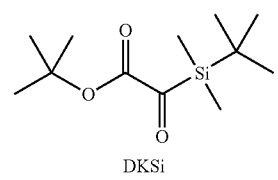

DKSi

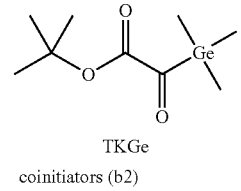

TKGe coinitiators (b2)

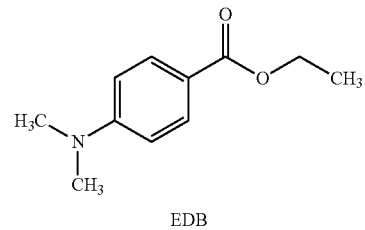

EDB

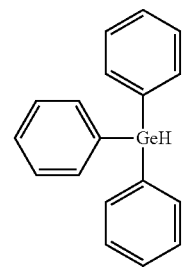

Ph$_3$GeH

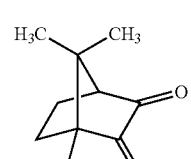

Camphorquinone (CQ)

component (b3)

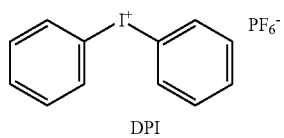

DPI compounds having a polymerizable double bond (a)

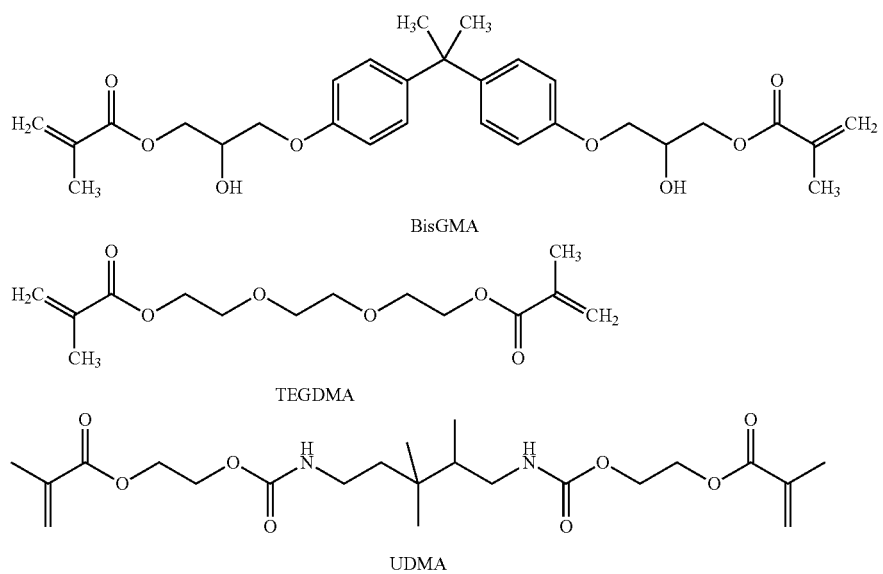

BisGMA

TEGDMA

UDMA bisacylgermane photoinitiator for comparison

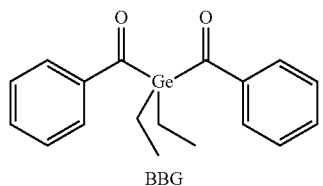

BBG

Figure 1B:
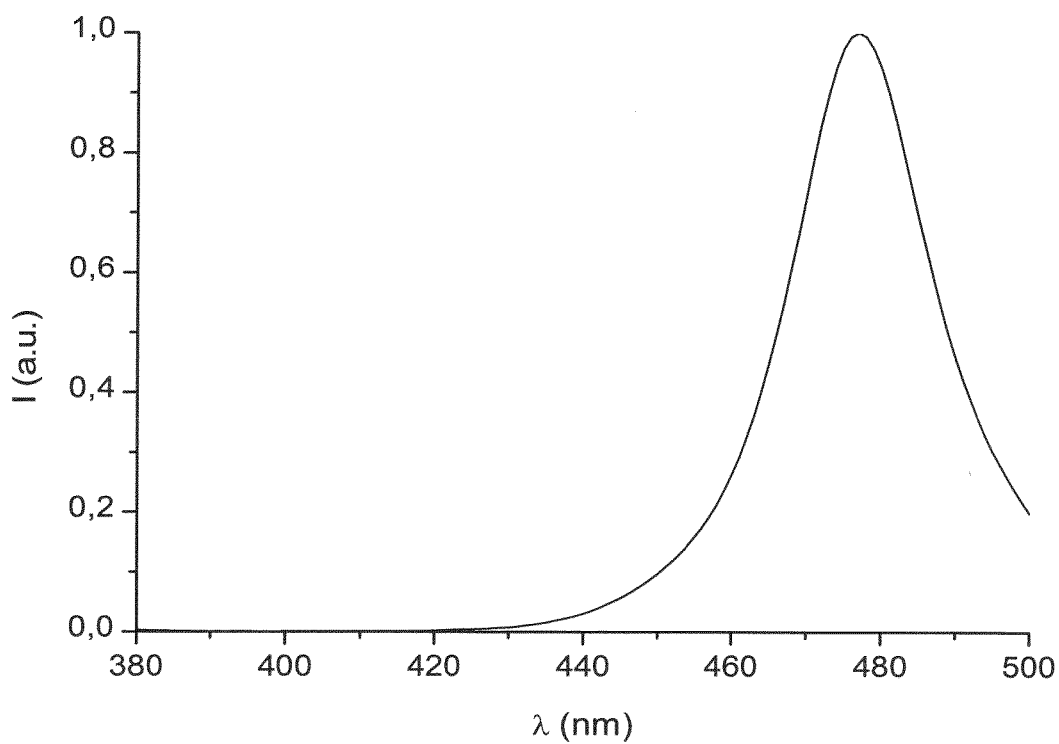

Scheme 7. Chemical structures of compound of formula (I) (b1), coinitiators (b2), component (b3), compounds having a polymerizable double bond (a) and BBG Irradiation Sources Several light sources were used for the irradiation of the photocurable samples: LED centered at 405 nm (M405L2—ThorLabs; ~110 mW cm$^{-2}$), at 420 nm (M420L2—ThorLabs; ~80 mW cm$^{-2}$), at 455 nm (M455L2—ThorLabs; ~60 mW cm$^{-2}$) and blue dental LED centered at 477 nm (SmartLite® Focus from Dentsply ~70 mW cm$^{-2}$ in the selected conditions). Different emission spectra of the irradiation sources are given in FIGS. 1a and 1b.

Photopolymerization Experiments:

For the photopolymerization experiments, the conditions are given in the figure captions. The photo-sensitive formulations were deposited on a BaF$_2$ pellet in laminate (about 25 μm or 30 20 μm thick samples) or under air (about 20 μm thick for adhesives and 1.4 mm for thick samples) for irradiation with different lights. The evolution of the double bond content of methacrylate was continuously followed by real time FTIR spectroscopy (JASCO FTIR 4100) at about 1630 cm$^{-1}$ for thin samples (10-30 μm) or 6165 cm$^{-1}$ for thick samples (1-2 mm—use of NIR), respectively.

Figure 2A:
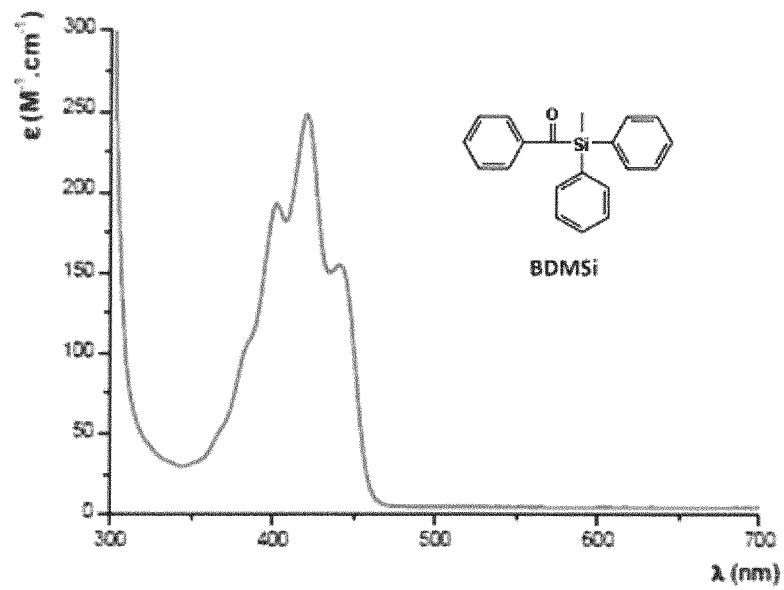
FIGS. 2a and 2b show the UV-VIS absorption spectra of benzoyldiphenylmethylsilane (BDMSi) and benzoyltrimethylsilane (BTMSi) in acetonitrile.
Figure 2B:
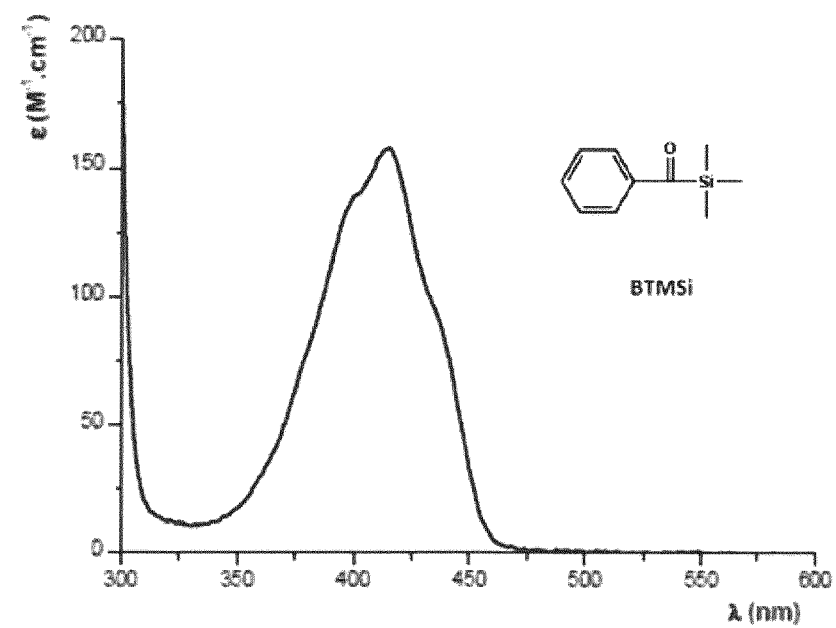

Example 3: Photopolymerisation Testing of Polymerization Initiator Systems Comprising an Acylsilane Testing of the Light Absorption Properties of BDMSi and BTMSi:

Acylsilanes are usually characterized by a n-π* transition centered at about 420 nm. The absorption spectra of BDMSi and BTMSi are depicted in FIGS. 2a and 2b. These two compounds allow good light absorption properties in the 380-460 nm range and can be used for dental LED (alone or in combination with CQ).

Figure 3:
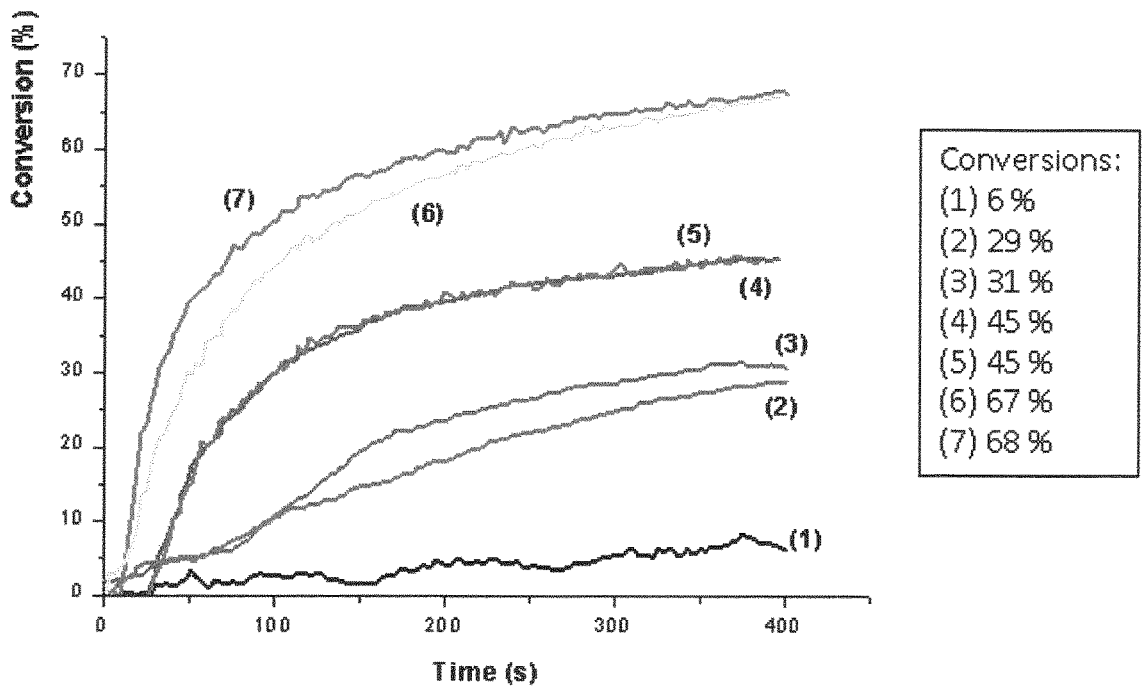
FIG. 3 shows the photopolymerization profiles of bisphenol A-glycidyl methacrylate (Bis-GMA)/triethyleneglycol dimethacrylate (TEGDMA) formulations polymerized in samples of 25 μm thickness in laminate upon the exposure to LED at 405 nm for the following different polymerization initiator systems.

Testing of Photopolymerization with a Three-Component Polymerization Initiator Systems Example 3a: The Acysilane/EDB/DPI Systems Upon a LED at 405 nm, the BDMSi/EDB/DPI was found as a good initiating system for a BisGMA/TEGDMA blend, as can be gathered from FIG. 3. The best behavior was found for the three-component system BDMSi/EDB/DPI. A similar behavior was found for BTMSi/EDB/DPI, as can be gathered from FIG. 4. For all these experiments, a good bleaching was observed and colorless polymers were obtained.

For thick samples (1.4 mm), a similar behavior was also found and the acylsilane/EDB/DPI can efficiently initiate the polymerization of a representative dental resin (cf. FIG. 5; for both BTMSi and BDMSi).

Example 3b: The Acylsilane/Ph$_3$GeH/DPI Systems

Ph$_3$GeH can also be used as coinitiator in the three-component acylsilane/Ph$_3$GeH/DPI systems, as can be gathered from FIG. 6. The performance in presence of Ph$_3$GeH was excellent and the bleaching was particularly remarkable.

Example 3c: Four-Component Polymerization Initiator Systems

To improve the matching of the emission spectrum of dental LED with the absorption of the photo-initiating system, the use of CQ/acylsilane combination can be worthwhile. In FIG. 7, it can be noted that BDMSi will absorb some light from the SmartLite® Focus in the 420-460 nm range. CQ/Ph$_3$GeH/DPI and BDMSi/Ph$_3$GeH/DPI were already efficient systems; the CQ/BDMSi/Ph$_3$GeH/DPI turned out to be better. The same behaviour was found for EDB as coinitiator (CQ/BDMSi/EDB/DPI better than CQ/EDB/DPI). The final conversion reached for CQ/acysilane versus CQ alone for different LEDs can be gathered from Table 1 below. It can be noted that a better performance was always obtained for CQ/acylsilane versus CQ.

The CQ/Acylsilane/EDB/DPI System:

As can be gathered from FIG. 8, in the presence of the acylsilane BDMSi, the polymerization initiating ability was improved, since a higher conversion rate was obtained for CQ/BDMSi/EDB/DPI (cf. curve (2)) compared with CQ/EDB/DPI)(cf. curve (1).

The CQ/Acylsilane/Ph$_3$GeH/DPI system:

As can be gathered from FIG. 9, in presence of the acylsilane BDMSi, the polymerization initiating ability was improved, since a higher conversion rate was obtained for CQ/acylsilane/Ph$_3$GeH/DPI (cf. curve (2)) compared with CQ/Ph$_3$GeH/DPI (cf. curve (1).

in dental materials. From FIGS. 12 and 13 it can be seen that the polymerization process was also good under air for thin samples (20 µm; FIG. 12) as well as for thick samples (1.4 mm; FIG. 13). However, as can gathered from FIG. 12 compared with FIG. 11, for thin samples, conversion rate of DKSi alone dropped down, since with very thin samples of e.g. 20 µm, there are very strong oxygen inhibition conditions, and thus, free radical polymerization will always be inhibited under air with such a thin film due to the trapping of the free radicals. Furthermore, from FIG. 12 it can be seen that in the presence of camphor quinone, the initiating ability of the CQ/DKSi/EDB/DPI system was only moderately improved compared to DKSi/EDB/DPI (cf. curve 4 vs. curve 3) suggesting a good reactivity of DKSi versus camphor quinone.

For the polymerization testing, the following mixtures were prepared:

The compositions according to Examples 4a, 4b and 4c have been prepared as described below, wherein the resulting compositions of the starting materials were polymerized at 37° C. Then, the polymerization enthalpies of these compositions were measured with the differential scanning calorimeter DSC 7 from Perkin Elmer. The results of these measurements are summarized in Table 2 below.

Example 4a 2.0000 g (4.2503 mmol) 11,14-Dioxa-2,9-diazaheptadec-16-enoicacid, 4,4,6,16 (or 4,6,6,16)-tetramethyl-10,15-di-

TABLE 1

Conversions reached after 20 s of irradiation for the polymerization of a blend Bis-GMA/TEGDMA (70%/30% w/w); different LED irradiations (under air).

| Polymerization initiator system | LED at 405 110 mW/cm$^2$ | LED at 420 80 mW/cm$^2$ | LED at 455 60 mW/cm$^2$ | LED at 477 70 mW/cm$^2$ |
|---|---|---|---|---|
| CQ/BDMSi/Ph$_3$GeH/DPI (1%/2%/2%/2% w/w) | 38 | 34 | 35 | 33 |
| CQ/Ph$_3$GeH/DPI (1%/2%/2% w/w) | 32 | 28 | 29 | 23 |

Example 4. Silylglyoxylate in Polymerization Initiator Systems for Dental Materials

Example 4: Photopolymerization Testing of Polymerization Initiator Systems Comprising a Glyoxylate Silyl Compound As an alternative for acylsilanes, silylglyoxylates may be used. As an example of the silylgyoxylate species, tert-Butyl (tert-butyldimethylsilyl)glyoxylate (DKSi) was tested as compound of formula (I).

Testing of the Light Absorption Properties of DKSi

As can be gathered from FIG. 10, the absorption of DKSi was better than the absorption of the acylsilanes BDMSi and BTMSi for the 450 to 500 nm range. Therefore, DKSi is more adapted for blue light irradiation than the acylsilanes.

DKSi was found to be a good initiator for the polymerization of BisGMA/TEGDMA upon blue LED (SmartLite® Focus) in laminate, i.e. when the formulation is covered with means for separating it from the air atmosphere, i.e. a translucent foil (cf. FIG. 11, curve (3)). DKSi can be used as a Type I initiator. In presence of EDB and DPI, the polymerization profiles were improved, as can be gathered from FIG. 11, curve (1) or (2) versus curve (3). Therefore, the two-component DKSi/EDB and the three-component DKSi/EDB/DPI systems are particularly attractive for applications oxo-,2-[(2-methyl-1-oxo-2-propen-1-yl)oxy]ethyl ester (UDMA), 0.0406 (0.1661 mmol) tert-Butyl (tert-butyldimethylsilyl) glyoxylate (DKSi) and 0.0017 g (0.0079 mmol) 2,6-di-tert-butyl-p-cresol were mixed homogeneously.

Example 4b 2.0000 g (4.2503 mmol) 11,14-Dioxa-2,9-diazaheptadec-16-enoicacid, 4,4,6,16 (or 4,6,6,16)-tetramethyl-10,15-di-oxo-,2-[(2-methyl-1-oxo-2-propen-1-yl)oxy]ethyl ester (UDMA), 0.0415 (0.1698 mmol) tert-Butyl (tert-butyldimethylsilyl)glyoxylate (DKSi), 0.0288 g (0.1490 mmol) ethyldimethylaminobenzoate (EDB) and 0.0017 g (0.0079 mmol) 2,6-di-tert-butyl-p-cresol were mixed homogeneously.

Example 4c 2.0000 g (4.2503 mmol) 11,14-Dioxa-2,9-diazaheptadec-16-enoicacid, 4,4,6,16 (or 4,6,6,16)-tetramethyl-10,15-di-oxo-,2-[(2-methyl-1-oxo-2-propen-1-yl)oxy]ethyl ester (UDMA), 0.0425 (0.1739 mmol) tert-Butyl (tert-butyldimethylsilyl)glyoxylate (DKSi), 0.0295 g (0.1527 mmol) ethyldimethylaminobenzoate (EDB), 0.0333 g (0.0782 mmol) diphenyliodonium hexafluoro phosphate (DPI) and 0.0017 g (0.0079 mmol) 2,6-di-tert-butyl-p-cresol were mixed homogeneously.

TABLE 2

| Examples | DKSi [mol-%] | EDB [mol-%] | DPI [mol-%] | Δ$_R$H [kJ/mol] | t$_{hmax}$ [min] |
|---|---|---|---|---|---|
| Example 4a | 3.75 | — | — | −34.4 ± 1.6 | 1.404 |
| Example 4b | 3.71 | 3.26 | — | −48.8 ± 5.4 | 0.625 |
| Example 4c | 3.73 | 3.27 | 1.68 | −47.2 ± 8.9 | 0.630 |

Example 4: Polymerization of Thick Samples (Thickness=6 mm)

As can be gathered from Example 4a above, DKSi alone was already a good polymerization initiator system, albeit the performance can be improved by addition of e.g. EDB or EDB/DPI, as shown e.g. in Examples 4b and 4c. With a sample thicker than that applied in 3a, performance could be further improved. Therefore, DKSi (2% w/w) was tested for the polymerization of UDMA formulations under air for thick samples of 6 mm (compared to 1.4 mm in Example 4a). The use of DKSi alone is for example interesting for amine-free formulations. The photopolymerization kinetic has been recorded by following the decrease of the methacrylate C=C band by near infra-red spectroscopy (at about 6160 cm$^{-1}$). As shown in FIG. 16, an excellent photopolymerization profile was obtained with a very high polymerization rate and final conversion. This clearly shows the high performance of DKSi alone as polymerization initiator system.

Example 4e: Bleaching of DKSi/EDB Versus CQ/EDB for the Polymerization of Thick Samples (Thickness=6 mm)

The excellent bleaching property of DKSi is very useful for the synthesis of colourless or substantially colourless polymer upon blue LED irradiation. In this example, the final colour for the polymer obtained by photopolymerization of UDMA (thickness=6 mm) was compared for the two polymerization initiator systems CQ/EDB (0.5%/0.5% w/w) and DKSi/EDB (0.5%/0.5% w/w). Remarkably, the DKSi based photoinitiating system lead to a colourless polymer, while the CQ based system leads to a slight yellow colour (cf. FIG. 17).

Example 4f: Polymerization of Thick Samples (1.4 mm) Using CQ/DKSi Combination

DKSi and camphorquinone (CQ) exhibit an excellent matching with the emission spectrum of the "SmartLite" LED (cf. FIG. 18). Therefore, DKSi and CQ were used in combination with EDB for the polymerization of thick samples (cf. FIG. 19). Remarkably, for a similar weight content (0.5% w/w), DKSi and CQ exhibited a similar photoinitiating ability: The polymerization profiles for CQ/EDB and DKSi/EDB were similar, as can be seen from curves (1) and (2) of FIG. 19. However, the molecular weight of DKSi is higher than CQ, this means that DKSi exhibits a higher molar efficiency than EDB.

Surprisingly, the combination of CQ/DKSi together with EDB lead to a remarkable polymerization profile (cf. FIG. 19, curve (3)) which was significantly improved compared to CQ/EDB and DKSi/EDB: The final conversion was increased to about 10-15%.

Example 5: Photopolymerization Testing of a Polymerization Initiator System Comprising a Glyoxylate Germanyl Compound Tert-butyl (trimethylgermanyl)glyoxylate (TKGe) was tested as (b1) a compound of formula (I) together with 4,4,6,16 (or 4,6,6,16)-tetramethyl-10,15-dioxo-,2-[(2-methyl-1-oxo-2-propen-1-yl)oxy]ethyl ester (UDMA) as polymerizable compound (a).

FIG. 21 shows that the germanylglyoxylate TKGe exhibits a good photoinitiating ability upon blue LED which is comparable to silylglyoxylates.

Example 6: Comparison of the Bleaching Properties of a Silylglyoxylate Such as DKSi Versus a Bisacylgermane Such as BBG in Methacrylate Resins For example, in EP 1 905 415 A1, bisacylgermanes such as bis-(benzoyl) diethylgermane (BBG) are proposed as excellent photoinitiator upon blue light for dental materials. However, for a photoinitiator for use in the dental field, besides of the photoinitiating performance, the bleaching property is a further important parameter for the photoinitiator's overall performance. From the absorption spectra shown in FIGS. 22 and 23, it can be seen that remarkably, the bleaching of the photoinitiator, i.e. the decrease of the associated absorption peak, is much faster for DKSi (cf. FIG. 23) compared with BBG (cf. FIG. 22). Furthermore, from FIG. 24 it can be seen that the yellow index significantly decreases for DKSi, while for bis-(benzoyl) diethylgermane (BBG), there was only a minimal decrease of the yellow index. In conclusion, Example 6 shows that DKSi provides for excellent bleaching properties, in particular when compared with bisacylgermanes.

Example 7: Molecular Modelling of Compounds of Formula (I) Having 1,2-Diketone Moiety Molecular modelling was carried out with reference software Gaussian 09. For molecular modelling, the density functional theory (DFT) was used, which provides reliable data.

The following parameters were calculated:
a) The light absorption properties absorption wavelength ($\lambda_{max}$) and oscillator strength (indication on the ε),
b) the triplet state energy level (ET), and
c) the bond dissociation energy (BDE) for:
  c1) the cleavage process (C—C or Si—C or Ge—C)
  c2) the hydrogen abstraction reaction (C—H).

The calculations were carried out for DKSi as reference indicated as molecule 1, novel molecules 2 to 8 depicted in FIG. 25 and known molecules 9 to 19.

The results of the calculations are summarized in Tables 3 and 4 below.

TABLE 3

|  | molecule | $\lambda_{max}$ [nm] | Oscillator strength |
|---|---|---|---|
| reference DKSi | 1 | 467 | 0.002 |
| novel molecules | 2 | 462 | 0.003 |
|  | 3 | 475 | 0.002 |
|  | 4 | 474 | 0.002 |
|  | 5 | 436 | 0.004 |
|  | 6 | 432 | 0.005 |
|  | 7 | 567 | 0.001 |
|  | 8 | 570 | 0.001 |
| known molecules | 9 | 478 | 0.001 |
|  | 10 | 478 | 0.003 |
|  | 11 | 475 | 0.001 |
|  | 12 | 481 | 0.001 |
|  | 13 | 482 | 0.001 |
|  | 14 | 472 | 0.001 |
|  | 15 | 484 | 0.003 |
|  | 16 | 472 | 0.004 |

TABLE 3-continued

| molecule | $\lambda_{max}$ [nm] | Oscillator strength |
|---|---|---|
| 17 | 440 | 0.004 |
| 18 | 486 | 0.001 |
| 19 | 712 | 0.001 |

TABLE 4

| | molecule | ET [kcal/mol] | BDE Si—C=O or Ge—C=O [kcal/mol] | BDE O=C—R [kcal/mol] |
|---|---|---|---|---|
| reference DKSi | 1 | 42.03 | 71.57 | 67.15 |
| novel molecules | 2 | 41.38 | 71.07 | 67.88 |
| | 3 | 42.15 | 73.68 | 71.08 |
| | 4 | 42.06 | 72.07 | 68.4 |
| | 5 | 45.19 | 71.48 | 63.92 |
| | 6 | 45.13 | 73.46 | 67.16 |
| | 7 | 34.91 | 70.37 | 63.05 |
| | 8 | 34.87 | 72.51 | 67.01 |
| known molecules | 9 | 42.4 | 72.88 | 68.32 |
| | 10 | 42.35 | 71.27 | 68.47 |
| | 11 | 42.52 | 73.59 | 70.07 |
| | 12 | 41.44 | 73.62 | 70.31 |
| | 13 | 41.28 | 73.45 | 70.1 |
| | 14 | 42.16 | 72.07 | 67.51 |
| | 15 | 41.44 | 71.93 | 69.98 |
| | 16 | 42.48 | 69.75 | 67.43 |
| | 17 | 42.66 | 67.69 | 66.91 |
| | 18 | 41.46 | 70.34 | 66.52 |
| | 19 | 26.26 | 65.5 | 56.03 |

From the above calculation results, the following conclusions can be drawn:

1) For all molecules 1 to 19, a cleavage from the triplet state can be ruled out, since the triplet state energy level is lower than the bond dissociation energy (BDE) leading to an endothermic (defavorable) cleavage reaction;
2) the cleavage occurs from the singlet excited state (Si), in agreement with experimental results;
3) the Si—C cleavage can be ruled out: the C—C bond is weaker, in agreement with experimental results; and
4) from the calculations, it appears that molecules 2, 4, 5, 6, 9, 10, 14, 16, 17 and 18 may have a cleavability which appears to be comparable to or even better compared with reference molecule 1 (DKSi). Furthermore, these molecules show an aborption wavelength $\lambda_{max}$ within the range of 432 to 478 nm, that is they are suitable for the light sources typically applied in dental applications. In particular, molecules 5 and 6 are preferable, since they are characterized by a potentially better cleavage process compared to the reference molecule (1) DKSi. These molecules have an advantageously low bond dissociation energy (BDE) for the O=C—R bond and a high triplet state energy level (ET). Molecules 7 and 19 may be readily cleaved owing to their low bond dissociation energy (BDE) for the O=C—R bond, but their absorption wavelength $\lambda_{max}$ is not within the range typically applied in dental applications, but in the green (molecule 7: $\lambda_{max}$=567 nm) and red part (molecule 19: $\lambda_{max}$=712 nm) of the spectrum.

In conclusion, the above experimental examples support that owing to the present polymerization initiator system, both a high conversion rate of the compounds having a polymerizable double bond of the matrix material and advantageous kinetics in terms of the polymerization time were obtained. For example, DKSi as compound of formula (I) alone, without the optional components (b2) coinitiator and (b3) iodonium salt, provides a high polymerization rate and high final conversions, as can be gathered from Examples 4a and 4d.

Furthermore, the experimental examples show that the present polymerization initiator system is suitable for polymerizing relatively thin films of up to 0.1 mm, such as adhesive films, as well as for relative thick samples having a thickness of about 1 to 2 mm or more, such as fillings and prosthetics. With the present polymerization initiator system, good bleaching is observed and thus, colorless polymers are obtained.

From the above examples, it appears that the advantageous effects of polymerizing relatively thin films of up to 0.1 mm and good bleaching are particularly attained due to synergistic effects between (b1) compound of formula (I), (b2) an optional coinitiator and (b3) an optional iodonium salt of the present polymerisation initiator system.

The invention claimed is:

1. A dental composition comprising
   (a) one or more compounds having at least one polymerizable double bond;
   (b) a polymerization initiator system comprising
      (b1) a compound of the following formula (I):

X—R  (I)

wherein
   X is a group of the following formula (II):

(II)

wherein
      M is Si or Ge;
      $R^1$ represents a substituted or unsubstituted hydrocarbyl or hydrocarbylcarbonyl group;
      $R^2$ represents a substituted or unsubstituted hydrocarbyl or hydrocarbylcarbonyl group;
      $R^3$ represents a substituted or unsubstituted hydrocarbyl group; and
   R (i) has the same meaning as X, whereby the compound of formula (I) may be symmetrical or unsymmetrical; or
   (ii) is a group of the following formula (III):

(III)

wherein
      Y represents a single bond, an oxygen atom or a group NR', wherein R' represents a substituted or unsubstituted hydrocarbyl group;
      $R^4$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
   (iii) when M is Si, R may be a substituted or unsubstituted hydrocarbyl group.

2. The dental composition according to claim 1, which further comprises
(b2) a coinitiator.

3. The dental composition according to claim 2, wherein the coinitiator is an electron donor.

4. The dental composition according to claim 3, wherein the electron donor is an amine compound or a compound having a Si—H or Ge—H bond.

5. The dental composition according to claim 1, further comprising one or more components selected from the group consisting of
(b3) an iodonium salt, a sulfonium salt and a phosphonium salt.

6. The dental composition according to claim 5, wherein the iodonium salt is diphenyliodonium hexafluorophosphate or (4-methylphenyl)[4-(2-methylpropyl)phenyl]iodonium hexafluorophosphate.

7. The dental composition according to claim 1, further comprising
(b4) an aromatic tertiary phosphine compound of the following formula (IV):

Z—R$^5$     (IV)

wherein
Z is a group of the following formula (V)

R$^6$(Ar)P—     (V)

wherein
R$^6$ represents a substituted or unsubstituted hydrocarbyl group;
Ar represents a substituted or unsubstituted aryl or heteroaryl group;
R$^5$ is a substituted or unsubstituted hydrocarbyl group or a group LZ',
wherein
L is a substituted or unsubstituted divalent hydrocarbyl group which may contain a linkage selected from a group consisting of an ether linkage, a thioether linkage, an ester linkage, an amide linkage, and a urethane linkage and
Z' has the same meaning as Z, whereby Z and Z' may be the same or different;
wherein the group R$^6$ and Ar may be substituted by one or more groups selected from a hydroxyl group, an oxo group, a —NR$^7$R$^8$ group (wherein R$^7$ and R$^8$, which may be the same or different, are selected from a hydrogen atom and C$_{1-6}$ alkyl groups), a carboxyl group, and a group having a polymerizable double bond, and R$^5$ and L may be substituted by one or more groups selected from a hydroxyl group, an oxo group, a —NR$^7$R$^8$ group (wherein R$^7$ and R$^8$, which may be the same or different, are selected from a hydrogen atom and C$_{1-6}$ alkyl groups), a carboxyl group, and a group having a polymerizable double bond.

8. The dental composition according to claim 1, wherein the polymerization initiator system comprises component (b1), (b2), (b3) and (b4) in a molar ratio ((b1):(b2):(b3):(b4)) of 1:(0.0 to 3.0):(0.0 to 3.0):(0.0 to 3.0).

9. The dental composition according to claim 1, further comprising a solvent and/or a particulate filler.

10. The dental composition according to claim 1, wherein the dental composition is a dental restorative or dental prosthetic composition.

11. The dental composition according to claim 10, wherein the dental composition is a dental adhesive composition, a dental composite composition, a resin modified dental cement, a pit and fissure sealer, a desensitizer or a varnish.

* * * * *